United States Patent
Smeltzer et al.

(10) Patent No.: US 12,042,248 B2
(45) Date of Patent: Jul. 23, 2024

(54) DEVICE AND METHOD FOR IN VIVO PHOTOACOUSTIC DIAGNOSIS AND PHOTOTHERMAL PURGING OF INFECTED BLOOD

(71) Applicant: BioVentures, LLC, Little Rock, AR (US)

(72) Inventors: Mark S. Smeltzer, Little Rock, AR (US); Vladimir Zharov, Little Rock, AR (US); Ekaterina Galanzha, Little Rock, AR (US)

(73) Assignee: BioVentures, LLC, Little Rock, AR (US)

( * ) Notice: Subject to any disclaimer, the term of this patent is extended or adjusted under 35 U.S.C. 154(b) by 0 days.

(21) Appl. No.: 18/215,635

(22) Filed: Jun. 28, 2023

(65) Prior Publication Data

US 2023/0355101 A1 Nov. 9, 2023

Related U.S. Application Data

(63) Continuation of application No. 17/668,909, filed on Feb. 10, 2022, now Pat. No. 11,723,540, which is a
(Continued)

(51) Int. Cl.
*A61B 5/00* (2006.01)
*A61B 5/145* (2006.01)
(Continued)

(52) U.S. Cl.
CPC ........ *A61B 5/0095* (2013.01); *A61B 5/14525* (2013.01); *A61B 5/4839* (2013.01); *A61K 41/00* (2013.01); *A61K 49/221* (2013.01);

*A61M 5/007* (2013.01); *G01N 33/48728* (2013.01); *G01N 33/569* (2013.01)

(58) Field of Classification Search
CPC .................................................... A61B 5/0036
See application file for complete search history.

(56) References Cited

U.S. PATENT DOCUMENTS

| | | |
|---|---|---|
| 4,333,474 A | 6/1982 | Nigam |
| 5,972,721 A | 10/1999 | Bruno et al. |

(Continued)

FOREIGN PATENT DOCUMENTS

| | | |
|---|---|---|
| DE | 10343442 A1 | 4/2005 |
| WO | 2006049570 A2 | 5/2006 |

(Continued)

OTHER PUBLICATIONS

Heitsch et al., "Multifunctional particles: Magnetic nanocrystals and gold nanorods coated with fluorescent dye-doped silica shells," Journal of Solid State Chemistry, 2008, pages.
(Continued)

*Primary Examiner* — Joseph M Santos Rodriguez
(74) *Attorney, Agent, or Firm* — POLSINELLI PC

(57) ABSTRACT

A method of non-invasively detecting and purging bacterial cells using a modified photoacoustic in vivo flow cytometer device is described herein. In particular, a method of detecting bacterial cells by analyzing photoacoustic pulses emitted in response to laser pulses from a pulsed laser source and/or selectively destroying the detected bacterial cells using a non-linear photothermal response induced by a high-energy laser pulse is described herein.

22 Claims, 36 Drawing Sheets

Related U.S. Application Data continuation of application No. 16/272,798, filed on Feb. 11, 2019, now Pat. No. 11,259,705, which is a continuation of application No. 14/668,418, filed on Mar. 25, 2015, now abandoned, which is a continuation-in-part of application No. PCT/US2013/061673, filed on Sep. 25, 2013.

(60) Provisional application No. 61/705,491, filed on Sep. 25, 2012.

(51) Int. Cl.
| | | |
|---|---|---|
| *A61K 41/00* | (2020.01) | |
| *A61K 49/22* | (2006.01) | |
| *A61M 5/00* | (2006.01) | |
| *G01N 33/487* | (2006.01) | |
| *G01N 33/569* | (2006.01) | |

(56) References Cited

U.S. PATENT DOCUMENTS

| | | |
|---|---|---|
| 6,368,318 B1 | 4/2002 | Visuri et al. |
| 6,428,531 B1 | 8/2002 | Visuri et al. |
| 6,466,806 B1 | 10/2002 | Geva et al. |
| 6,514,203 B2 | 2/2003 | Bukshpan |
| 6,530,944 B2 | 3/2003 | West et al. |
| 6,710,871 B1 | 3/2004 | Goix |
| 6,833,540 B2 | 12/2004 | MacKenzie et al. |
| 6,846,288 B2 | 1/2005 | Nagar et al. |
| 7,220,385 B2 | 5/2007 | Blecka et al. |
| 7,500,953 B2 | 3/2009 | Oraevsky et al. |
| 9,144,383 B2 | 9/2015 | Zharov |
| 9,217,703 B2 | 12/2015 | Zharov |
| 9,451,884 B2 | 9/2016 | Zharov et al. |
| 11,154,360 B2 | 10/2021 | Zharov et al. |
| 11,259,704 B2 | 3/2022 | Zharov |
| 2002/0099283 A1 | 7/2002 | Christ et al. |
| 2003/0216663 A1 | 11/2003 | Kerseu-Willuhn et al. |
| 2004/0039379 A1 | 2/2004 | Viator et al. |
| 2004/0188602 A1 | 9/2004 | Chinn et al. |
| 2005/0004458 A1 | 1/2005 | Kanayama et al. |
| 2005/0106739 A1 | 5/2005 | Cabuz et al. |
| 2005/0124869 A1 | 6/2005 | Hefti et al. |
| 2005/0175540 A1 | 8/2005 | Oraevsky et al. |
| 2006/0078949 A1 | 4/2006 | Offer et al. |
| 2006/0122583 A1 | 6/2006 | Pesach et al. |
| 2006/0184042 A1 | 8/2006 | Wang et al. |
| 2007/0015978 A1 | 1/2007 | Kanayama et al. |
| 2007/0015992 A1 | 1/2007 | Filkins et al. |
| 2007/0121697 A1 | 5/2007 | Burgholzer et al. |
| 2007/0213613 A1 | 9/2007 | Isida et al. |
| 2007/0232940 A1 | 10/2007 | Fine et al. |
| 2007/0269345 A1 | 11/2007 | Schilffarth et al. |
| 2007/0292495 A1 | 12/2007 | Ludwig et al. |
| 2008/0149566 A1 | 6/2008 | Messersmith et al. |
| 2008/0160090 A1 | 7/2008 | Oraevsky et al. |
| 2008/0269847 A1 | 10/2008 | Nemenov |
| 2008/0269849 A1 | 10/2008 | Lewis |
| 2009/0093713 A1 | 4/2009 | Hyde et al. |
| 2009/0156932 A1 | 6/2009 | Zharov |
| 2009/0227997 A1 | 9/2009 | Wang et al. |
| 2009/0292195 A1 | 11/2009 | Boyden et al. |
| 2009/0326614 A1 | 12/2009 | El-Sayed et al. |
| 2010/0278923 A1 | 11/2010 | Chen et al. |
| 2011/0105867 A1 | 5/2011 | Schultz et al. |
| 2011/0117028 A1 | 5/2011 | Zharov |
| 2011/0134426 A1 | 6/2011 | Kaduchak et al. |
| 2011/0218140 A1 | 9/2011 | Gonsalves et al. |
| 2011/0306865 A1 | 12/2011 | Thornton et al. |
| 2012/0022360 A1 | 1/2012 | Kemp |
| 2012/0065490 A1 | 3/2012 | Zharov et al. |
| 2012/0179227 A1 | 7/2012 | Schomacker et al. |
| 2012/0202278 A1 | 8/2012 | Wagner et al. |
| 2012/0237605 A1 | 9/2012 | Messersmith et al. |
| 2013/0030307 A1 | 1/2013 | Rajan et al. |
| 2013/0060122 A1 | 3/2013 | Zharov |
| 2013/0123604 A1 | 5/2013 | Oyama |
| 2015/0065685 A1 | 3/2015 | College |
| 2015/0150463 A1 | 6/2015 | Smeltzer et al. |
| 2015/0282716 A1 | 10/2015 | Smeltzer et al. |
| 2015/0335741 A1 | 11/2015 | Smeltzer et al. |
| 2015/0351640 A1 | 12/2015 | Zharov |
| 2016/0058297 A1 | 3/2016 | Zharov |
| 2016/0354150 A1 | 12/2016 | Zharov |
| 2018/0000351 A1 | 1/2018 | Zharov |
| 2018/0160090 A1 | 6/2018 | Tsukagoshi |

FOREIGN PATENT DOCUMENTS

| | | |
|---|---|---|
| WO | 2013067419 A1 | 5/2013 |
| WO | 2014052449 A1 | 4/2014 |
| WO | 2016109831 A | 7/2016 |
| WO | 2016196791 A1 | 12/2016 |

OTHER PUBLICATIONS

Ulmer, A., et al., "Detecting Circulating Melanoma Cells," J. Invest. Dermatol., 2011, pp. 1774-1775, vol. 131.

Van Dijk, M., et al., "Absorption and scattering microscopy of single metal nanoparticles," Phys. Chem. Chem. Phys., 2006, pp. 3486-3495, vol. 8.

Wang, L., "Multiscale photoacoustic microscopy and computed tomography," NIH Public Access Author Manuscript, available in PMC Aug. 29, 2010, pp. 1-16, published in final edited form as: Nat. Photonics, Aug. 29, 2009, pp. 503-509, vol. 3, No. 9.

Wang, L., et al., "Fiber-laser-based photoacoustic microscopy and melanoma cell detection," J. Biomed. Opt., Jan. 2011, pp. 011014-1 to 011014-4, vol. 16, No. 1.

Wang, L., et al., "Photoacoustic Tomography: In Vivo Imaging from Organelles to Organs," Sci., Mar. 23, 2012, pp. 1458-1462, vol. 335.

Wang, Z., et al., "CD146, a multi-functional molecule beyond adhesion," Cancer Lett., 2013, pp. 150-162, vol. 330.

Wei, X., et al., "Selective Uptake of Indocyanine Green by Reticulocytes in Circulation," Invest. Opthalmol. Vis. Sci., Oct. 2003, pp. 4489-4496, vol. 44, No. 10.

Weight, R., et al., "Photoacoustic detection of metastatic melanoma cells in the human circulatory system," Opt. Lett., Oct. 15, 2006, pp. 2998-3000, vol. 31, No. 20, Optical Society of America.

Wicha, M, et al., "Circulating Tumor Cells: Not All Detected Cells Are Bad and Not All Bad Cells Are Detected," J. Clin. Oncol., 2011, pp. 1508-1511, vol. 29.

Williams, S., "Circulating Tumor Cells," PNAS, Mar. 26, 2013, p. 4861, vol. 110, No. 13.

Witzig, T., et al., "Detection of Circulating Cytokeratin-positive Cells in the Blood of Breast Cancer Patients Using Immunomagnetic Enrichment and Digital Microscopy," Clin. Cancer Res., May 2002, pp. 1085-1091, vol. 8.

Xu, M., et al., "Photoacoustic imaging in biomedicine," Rev. Sci. Instrum., 2006, pp. 041101-1 to 041101-22, vol. 77.

Xu, M., et al., "Circulating Tumor Cells and Melanoma Progression," J. Invest. Dermatol., 2010, pp. 2349-2351, vol. 130.

Yang, J., et al., "Melanoma Proteoglycan Modifies Gene Expression to Stimulate Tumor Cell Motility, Growth, and Epithelial-to-Mesenchymal Transition," Cancer Res., 2009, pp. 7538-7547, vol. 69, No. 19.

Yu, M., et al., "Circulating tumor cells: approaches to isolation and characterization," j Cell Biol., 2011, pp. 373-382, vol. 192, No. 3.

Yu, M., et al., "Circulating Breast Tumor Cells Exhibit Dynamic Changes in Epithelial and Mesenchymal Composition," Sci., Feb. 1, 2013, pp. 580-584, vol. 339.

Zharov, V., et al., "Photothermal detection of local thermal effects during selective nanophotothermolysis," Appl. Phys. Lett., Dec. 15, 2003, pp. 1-3, vol. 83, No. 24.

Zharov, V., et al., "Infrared imaging of subcutaneous veins," Lasers Surg. Med., Jan. 2004, pp. 56-61, vol. 34, No. 1, Wiley-Liss, Inc.

(56) References Cited

OTHER PUBLICATIONS

Zharov, V., et al., "Photothermal Imaging of Nanoparticles and Cells," IEEE Journal of Selected Topics in Quantum Electronics, Jul./Aug. 2005, pp. 733-751, vol. 11, No. 4.

Zharov, V., et al., "Microbubbles-overlapping mode for laser killing of cancer cells with absorbing nanoparticle clusters," J. Physics D: Appl. Phys., 2005, pp. 2571-2581, vol. 38.

Zharov, V., et al., "Photoacoustic tweezers with a pulsed laser source: theory and experiments," J. Physics D: Appl. Phys., 2005, pp. 1-13, vol. 38, IOP Publishing Ltd, United Kingdom.

Zharov, V., et al., "Photothermal image flow cytometry in vivo," Opt. Lett., Mar. 15, 2005, pp. 628-630, vol. 30, No. 6.

Zharov, V., et al., "In Vivo Photothermal Flow Cytometry: Imaging and Detection of Individual Cells in Blood and Lymph Flow," J. Cellular Biochem., 2006, pp. 916-932, vol. 97, No. 5.

Zharov, V., et al., "In vivo photoacoustic flow cytometry for monitoring of circulating single cancer cells and contrast agents," Opt. Lett., Dec. 15, 2006, pp. 3623-3625, vol. 31, No. 24.

Zharov, V., et al., "Photothermal Flow Cytometry in Vitro for Detection and Imaging of Individual Moving Cells," Cytometry Part A, 2007, pp. 191-206, vol. 71A.

Zharov, V., et al., "Confocal photothermal flow cytometry in vivo," Proc. SPIE, Apr. 2005, pp. 15-26, vol. 5697.

Zharov, V., et al., "Integrated photohermal flow cytometry in vivo," J. Biomed. Opt., Sep./Oct. 2005, pp. 51502-1-051502-13, vol. 10, No. 5.

Zharov, V., et al., "Nanocluster model of photothermal assay: application for high-sensitive monitoring of nicotine-induced changes in metabolism, apoptosis, and necrosis at a cellular level," J. Biomed. Opt., Jul./Aug. 2005, pp. 044011-1-044011-15, vol. 10, No. 4.

Zharov, V., et al., "Self-assembling nanoclusters in living systems: application for integrated photothermal nanodiagnostics and nanotherapy," J. Nanomed., Dec. 2005, pp. 326-345, vol. 1, No. 4.

Zharov, V., et al., "Synergistic enhancement of selective nanophotothermolysis with gold nanoclusters: Potential for cancer therapy," Laser Surg. Med., 2005, pp. 219-226, vol. 37, No. 3.

Zharov, V., et al., "In vivo high-speed imaging of individual cells in fast blood flow," J. Biomed. Opt., Sep./Oct. 2006, pp. 054034-1-054034-4, vol. 11, No. 5.

Zharov, V., et al., "Photothermal Nanotherapeutics and Nanodiagnostics for Selective Killing of Bacteria Targeted with Gold Nanoparticles," Biophys. J., Jan. 2006, pp. 619-627, vol. 90, Biophysical Society.

Zharov, V., et al., "Photoacoustic flow cytometry: principle and application for real-time detection of circulating nanoparticles, pathogens, and contrast dyes in vivo," J. Biomed. Opt., Sep. 1, 2007, pp. 051503-1-051503-14, vol. 12, No. 5.

Zharov, V., et al., "Ultrasharp nonlinear photothermal and photoacoustic resonances and holes beyond the spectral limit," HHS Public Access Author Manuscript, available in PMC Jan. 2, 2015, pp. 1-16, Published in final edited form as: Nat. Photonics, Feb. 2011, pp. 110-116, vol. 5, No. 2.

Zhe, X., et al., "Circulating tumor cells: finding the needle in the haystack," Am. J. Cancer Res., 2011, pp. 740-751, vol. 1, No. 6.

Zheng, H., et al., "Detection of the Cancer Marker CD146 Expression in Melanoma Cells with Semiconductor Quantum Dot Label," J. Biomed. Nanotechnol., Aug. 2010, pp. 303-311, vol. 6, No. 4.

Haruna, M., et al., "Blood Volume Measurement at the Bedside Using ICG Pulse Spectrophotometry," Anesthesiology, 1998, pp. 1322-1328, vol. 89.

Iida, J., et al., "Cell surface chondroitin sulfate glycosaminoglycan in melanoma: role in the activation of pro-MMP-2 (progelatinase A)," Biochem. J., May 1, 2007, pp. 553-563, vol. 403, No. 3, Biochemical Society, Great Britain.

International Search Report and Written Opinion for PCT application No. PCT/US2013/061673, mailed Dec. 16, 2013, 8 pages.

International Search Report and Written Opinion for PCT application No. PCT/US2015/068341, mailed Mar. 17, 2016, 8 pages.

International Search Report and Written Opinion for PCT application No. PCT/US2016/035512, mailed Oct. 6, 2016, 12 pages.

Ion, R-M, et al., "The incorporation of various porphyrins into blood cells measured via flow cytometry, absorption and emission spectroscopy," Acta Biochim. Pol., 1998, pp. 833-845, vol. 45, No. 3.

Joosse, S., et al., "Biologic Challenges in the Detection of Circulating Tumor Cells," Cancer Res., Jan. 1, 2013, pp. 8-11, vol. 73, No. 1.

Kaiser, J., "Cancer's Circulation Problem," Sci., Feb. 26, 2010, pp. 1072-1074, vol. 327.

Khlebtsov, B., et al., "Optical amplification of photothermal therapy with gold nanoparticles and nanoclusters," Nanotechnol., 2006, pp. 5167-5179, vol. 17, Institute of Physics Publishing.

Khoja, L., et al., "Biomarker utility of circulating tumor cells in metastatic cutaneous melanoma," J. Invest. Dermatol., Jun. 2013, pp. 1582-1590, vol. 133, No. 6.

Kim, Y., et al., "Subtyping Lymphocytes in Peripheral Blood by Immunoperoxidase Labeling and Light Scatter/Absorption Flow Cytometry," Clin. Chem., 1985, pp. 1481-1486, vol. 31, No. 9.

Kim, J-W, et al., "In situ fluorescence microscopy visualization and characterization of nanometer-scale carbon nanotubes labeled with 1-pyrenebutanoic acid, succinimdyl ester," Appl. Phys. Lett., 2006, pp. 213110-1 to 213110-3, vol. 88.

Kim, M., et al., "Tumor Self-Seeding by Circulating Cancer Cells," Dec. 24, 2009, pp. 1315-1326, vol. 139, Elsevier Inc.

Kim, J-W, et al., "Golden carbon nanotubes as multimodal photoacoustic and photothermal high-contrast molecular agents," NIH Public Access Author Manuscript, available in PMC May 24, 2013, pp. 1-15, Published in final edited form as: Nat. Nanotechnol., Oct. 2009, pp. 688-694, vol. 4, No. 10.

Kim, J-W, et al., "Nanotheranostics of Circulating Tumor Cells, Infections and Other Pathological Factors in Vivo," NIH Public Access Author Manuscript, available in PMC Mar. 4, 2014, pp. 1-37, Published in final edited form as: Mol. Pharm., Mar. 4, 2013, pp. 813-830, vol. 10, No. 3.

Krishnamurthy, S., "The Emerging Role of Circulating Tumor Cells in Breast Cancer," Cancer Cytopathol., Jun. 25, 2012, pp. 161-166, vol. 120.

Lai, C., et al.,"CD133+ Melanoma Subpopulations Contribute to Perivascular Niche Morphogenesis and Tumorigenicity Through Vasculogenic Mimicry," Cancer Res., 2012, pp. 5111-5118, vol. 72, No. 19.

Langley, R., et al., "Tumor Cell-Organ Microenvironment Interactions in the Pathogenesis of Cancer Metastasis," Endocr. Rev., 2007, pp. 297-321, vol. 28, No. 3.

Lapotko, D., et al., "Photothermal image cytometry of human neutrophils," Cytometry, 1996, pp. 198-203, vol. 24, Wiley-Liss, Inc.

Lapotko, D., et al., "Spectral Evaluation of Laser-Induced Cell Damage with Photothermal Microscopy," Lasers in Surgery and Medicine, 2005, pp. 22-30, vol. 36, No. 1, Wiley-Liss, Inc.

Lasne, D., et al., "Label-free optical imaging of mitochondria in live cells," Opt. Exp., Oct. 17, 2007, pp. 14184-14193, vol. 15, No. 21.

Letfullin, R., et al., "Laser-induced explosion of gold nanoparticles: potential role for nanophotothermolysis of cancer," Nanomed., 2006, pp. 473-480, vol. 1, No. 4, Future Medicine Ltd.

Leung, C., et al., "Tumor Self-Seeding: Bidirectional Flow of Tumor Cells," Cell, Dec. 24, 2009, pp. 1226-1228, vol. 139, Elsevier Inc.

Li, C., et al., "Preparation and characterization of flexible nanoliposomes loaded with daptomycin, a novel antibiotic, for topical skin therapy," International Journal of Nanomedicine, Mar. 24, 2013, pp. 1285-1292, vol. 8.

Lianidou, E., et al., "Circulating Tumor Cells—New Challenges Ahead," Clin. Chem., 2012, pp. 805-807, vol. 58, No. 5.

Liao, H., et al., "Gold Nanorod Bioconjugates," Chem. Mater., 2005, pp. 4636-4641, vol. 17, No. 18, American Chemical Society.

Liu, Z., et al., "Negative enrichment by immunomagnetic nanobeads for unbiased characterization of circulating tumor cells from peripheral blood of cancer patients," J. Transl. Med., 2011, pp. 1-8, vol. 9, No. 70.

Ma, J., et al., "Isolation of tumorigenic circulating melanoma cells," Biochem. Biophys. Res. Commun., 2010, pp. 711-717, vol. 402, No. 4, Elsevier Inc.

(56) References Cited

OTHER PUBLICATIONS

Maheswaran, S., et al., "Circulating Tumor Cells: a window into cancer biology and metastasis," HHMI Author Manuscript, pp. 1-16, Published as: Curr. Opin. Genet. Dev., Feb. 2010, pp. 96-99, vol. 20, No. 1.

Menyaev, Y., et al., "Resolution of photoacoustic flow cytometry," Optical Society of America, 2013, 16 pages.

Molino, A., et al., "A Comparative Analysis of Three Different Techniques for the Detection of Cancer Cells in Bone Marrow," Cancer, Feb. 15, 1991, pp. 1033-1036, vol. 67.

Nagrath, S., et al., "Isolation of rare circulating tumour cells in cancer patients by microchip technology," NIH Public Access Author Manuscript, available in PMC May 10, 2011, pp. 1-11, Published in final edited form as: Nat., Dec. 20, 2007, pp. 1235-1239, vol. 450, No. 7173.

Nedosekin, D., et al., "Photothermal Multispectra Image Cytometry for Quantitative Histology of Nanoparticles and Micrometastasis in Intact, Stained and Selectively Burned Tissue," Cytometry Part A, 2010, pp. 1049-1058, vol. 77A.

Nedosekin, D., et al., "Ultra-fast photoacoustic flow cytometry with a 0.5 MHz pulse repetition rate nanosecond laser," Opt. Exp., 2010, pp. 8605-8620, vol. 18.

Nedosekin, D., et al., "In Vivo Ultra-Fast Photoacoustic Flow Cytometry of Circulating Human Melanoma Cells Using Near-Infrared High-Pulse Rate Lasers," Cytometry Part A, 2011, pp. 825-833, vol. 79A.

Nedosekin, D., et al., "In Vivo Plant Flow Cytometry: A First Proof-of-Concept," Cytometry Part A, 2011, pp. 855-865, vol. 79A.

Nedosekin, D., et al., Photothermal Confocal Spectromicroscopy of Multiple Cellular Chromophores and Flurophores, Biophys. J., Feb. 2012, pp. 672-681, vol. 102.

Nedosekin, D., et al., "Synergy of photoacoustic and fluorescence flow cytometry of circulating cells with negative and positive contrasts," J. Biophotonics, 2013, pp. 425-434, vol. 6, No. 5, Wiley-VCH Verlag GmbH & Co. KGaA, Weinheim, Germany.

Nedosekin, D., et al., "Photoacoustic and photothermal detection of circulating tumor cells, bacteria and nanoparticles in cerebrospinal fluid in vivo and ex vivo," J. Biophotonics, 2013, pp. 523-533, vol. 6, No. 6-7, Wiley- VCH Verlag GmbH & Co. KGaA, Weinheim, Germany.

Nedosekin, D., et al., "Photoacoustic-flurorescence in vitro flow cytometry for quantification of absorption, scattering and fluorescence properties of the cells," Proc. SPIE, 2013, pp. 858141-1 to 858141-6, vol. 8581.

Neeves, K., et al., "Catch Me If You Can: Isolating Circulating Tumor Cells from Flowing Blood," Clin. Chem., 2012, pp. 803-804, vol. 58, No. 5.

Nguyen, D., et al., "Metastasis: from dissemination to organ-specific colonization," Nat. Rev. Cancer, Apr. 2009, pp. 274-284, vol. 9, Macmillan Publishers Limited.

Novak, J., et al., "In vivo flow cytometer for real-time detection and quantification of circulating cells," NIH Public Access Author Manuscript, availabe in PMC Jan. 4, 2010, pp. 1-8, Published in final edited form as: Opt. Lett., Jan. 1, 2004, pp. 77-79, vol. 29, No. 1.

Notice of Allowance dated May 19, 2015 from related U.S. Appl. No. 12/945,576, 11 pages.

Notice of Allowance dated Jun. 28, 2016 from related U.S. Appl. No. 13/253,767, 9 pages.

Notice of Allowance dated Aug. 14, 2015 from related U.S. Appl. No. 13/661,551, 9 pages.

Notice of Allowance dated Feb. 26, 2019 from related U.S. Appl. No. 14/754,034, 7 pages.

O'Brien, C., et al., "Detection and Isolation of Circulating Melanoma Cells using Photoacoustic Flowmetry," J. Vis. Exp., Nov. 2011, pp. 1-5, vol. 57, e3559.

O'Brien, C., et al., "Capture of circulating tumor cells using photoacoustic flowmetry and two phase flow," JH. Biomed. Opt., Jun. 2012, pp. 061221-1 to 061221-9, vol. 17, No. 9.

Office Action dated Nov. 30, 2011 from related U.S. Appl. No. 12/334,217, 12 pages.

Office Action dated Apr. 26, 2012 from related U.S. Appl. No. 12/334,217, 10 pages.

Office Action dated Oct. 6, 2014 from related U.S. Appl. No. 13/253,767, 18 pages.

Office Action dated Apr. 16, 2015 from related U.S. Appl. No. 13/253,767, 17 pages.

Office Action dated Jul. 30, 2015 from related U.S. Appl. No. 13/253,767, 16 pages.

Office Action dated Feb. 22, 2016 from related U.S. Appl. No. 13/253,767, 7 pages.

Office Action dated Feb. 13, 2014 from related U.S. Appl. No. 13/661,551, 11 pages.

Office Action dated Oct. 7, 2014 from related U.S. Appl. No. 13/661,551, 10 pages.

Office Action dated Apr. 3, 2015 from related U.S. Appl. No. 13/661,551, 11 pages.

Office Action dated Jan. 30, 2017 from related U.S. Appl. No. 14/552,143, 14 pages.

Office Action dated Oct. 26, 2016 from related U.S. Appl. No. 14/668,418, 11 pages.

Office Action dated Nov. 24, 2017 from related U.S. Appl. No. 14/668,418, 12 pages.

Office Action dated Nov. 27, 2017 from related U.S. Appl. No. 14/728,849, 9 pages.

Office Action dated Dec. 8, 2017 from related U.S. Appl. No. 14/688,418, 29 pages.

Biris, A., et al., "In vivo Raman flow cytometry for real-time detection of carbon nanotube kinetics in lymp, blood, and tissues," J. Biomed. Opt., Mar./Apr. 2009, pp. 021006-1-021006-10, vol. 14, No. 2.

Blab, G., et al., "Optical readout of gold nanoparticle-based DNA microarrays without silver enhancement," Biophys. J. Biophys. Lett., 2006, pp. L13-L15, vol. 90, No. 1.

Bland, J., et al., "Statistical methods for assessing agreement between two methods of clinical measurement," Lancet, Feb. 8, 1986, pp. 307-310, vol. 1.

Boutrus, S., et al., "Portable two-color in vivo flow cytometer for real-time detection of fluorescently-labled circulating cells," NIH Public Access, Author Manuscript, available in PMC, Dec. 28, 2009, pp. 1-8, published in final edited form as: J. Biomed. Opt., 2007, pp. 020507, vol. 12, No. 2.

Brusnichkin, A., et al., "Ultrasensitive label-free photothermal imaging, spectral identification, and quantification of cytochrome c in mitochondria, live cells, and solutions," NIH Public Access Author Manuscript, available in PMC, May 11, 2012, pp. 1-28, Published in final edited form as: J. Biophotonics, Dec. 2010, pp. 791-806, vol. 3, No. 12.

Budd, G., et al., "Circulating Tumor Cells versus Imaging-Predicting Overall Survival in Metastatic Breast Cancer," Clin. Cancer Res., Nov. 1, 2006, pp. 6403-6409, vol. 12, No. 21.

Chaffer, C., et al., "A Perspective on Cancer Cell Metastasis," Sci., Mar. 25, 2011, pp. 1559-1564, vol. 25, No. 331.

Chen, Y., et al., "Platelet CD62P Expression and Microparticle in Murine Acquired Immune Deficiency Syndrome and Chronic Ethanol Comsumpton," Alcohol Alcoholism, Jan. 1, 2003, pp. 25-30, vol. 38, No. 1.

Chu, J., et al., "The Role of Cancer Stem Cells in the Organ Tropism of Breast Cancer Metastasis: A Mechanistic Balance between the "Seed" and the "Soil"?" Int. J. Breast Cancer, 2012, pp. 1-12, Article ID 209748, Hindawi Publishing Corporation.

Cristofanilli, M., et al., "Circulating tumor cells, disease progression, and survival in metastatic breast cancer," N. Engl. J. Med., 2004, pp. 781-791, vol. 351.

Cristofanilli, M., et al., "Circulating Tumor Cells: A Novel Prognostic Factor for Newly Diagnosed Metastatic Breast Cancer," J. Clin. Oncol., Mar. 1, 2005, pp. 1420-1430, vol. 23, No. 7.

De Bruyn, M., et al., "Melanoma-associated Chondroitin Sulfate Proteoglycan (MCSP)-targeted delivery of soluble TRAIL potently inhibits melanoma outgrowth in vitro and in vivo," Mol. Cancer, 2010, pp. 1-14, vol. 9, No. 301.

(56) References Cited

OTHER PUBLICATIONS

De Giorgi, V., et al., "Application of a Filtration- and Isolation-by-Size Technique for the Detection of Circulating mor Cells in Cutaneous Melanoma," J. Invest. Dermatol., 2010, pp. 2440-2447, vol. 130.
De La Zerda, A., et al., "Advanced contrast nanoagents for photoacoustic molecular imaging, cytometry, blood test and photothermal theranostics," Contrast Media Mol. Imaging, 2011, pp. 346-369, vol. 6, John Wiley & Sons, Ltd.
Dick, J., "Breast Cancer Stem Cells Revealed," PNAS, Apr. 1, 2003, pp. 3547-3549, vol. 100, No. 7.
European Extended Search Report dated Aug. 10, 2018 from related European Patent Application No. 15876378.9; 13 pages.
Freeman, J., et al., "Evaluation of a multi-marker immunomagnetic enrichment assay for the quantification of circulating melanoma cells," J. Transl. Med., 2012, pp. 1-9, vol. 10, No. 192.
Fukunaga-Kalabis, M., et al., "Beyond ABC: Another Mechanism of Drug Resistance in Melanoma Side Population," J. Invest. Dermatol., 2012, pp. 2317-2319, vol. 132.
Gaiduk, A., et al., "Room-Temperature Detection of a Single Molecule's Absorption by Photothermal Contrast," Sci., Oct. 15, 2010, pp. 353-356, vol. 330.
Galanzha, E., et al., "In vivo integrated flow image cytometry and lymph/blood vessels dynamic microscopy," J. Biomed. Opt., Sep./Oct. 2005, pp. 054018-1-054018-8, vol. 10, No. 5.
Glanzha, E., et al., "Advances in small animal mesentery models for in vivo flow cytometry, dynamic microscopy, and drug screening," World J. Gastroenterol., Jan. 14, 2007, pp. 192-218, vol. 13, No. 2, The WJG Press.
Galanzha, E., et al., "In vivo multispectral, multiparameter, photoacoustic lymph flow cytometry with natural cell focusing, label-free detection and multicolor nanoparticle probes," Cytometry A, 2008, pp. 884-894, vol. 73A, No. 10, with NIH Public Access Author Manuscript, available in PMC, Oct. 1, 2009, pp. 1-19.
Galanzha, E., et al., "In vivo, Noninvasive, Label-Free Detection and Eradication of Circulating Metastatic Melanoma Cells Using Two-Color Photoacoustic Flow Cytometry with a Diode Laser," Cancer Res., 2009, pp. 7926-7934, vol. 69, No. 20.
Galanzha, E., et al., "In vivo fiber-based multicolor photoacoustic detection and photothermal purging of metastasis in sentinel lymph nodes targeted by nanoparticles," NIH Public Access Author Manuscript, available in PMC, May 24, 2013, pp. 1-17, Published in final edited form as: J. Biophoton., Sep. 2009, pp. 528-539, vol. 2.
Galanzha, E., et al., "Nanotechnology-based molecular photoacoustic and photothermal flow cytometry platform for in-vivo detection and killing of circulating cancer stem cells," J. Biophoton., 2009, pp. 725-735, vol. 2, No. 12.
Galanzha, E., et al., "In vivo magnetic enrichment and multiplex photoacoustic detection of circulating tumour cells," NIH Public Access Author Manuscript, available in PMC, May 24, 2013, pp. 1-13, Published in final edited form as: Nat. Nanotechnol., Dec. 2009, pp. 855-860, vol. 4, No. 12.
Galanzha, E., et al., "In Vivo Photoacoustic and Photothermal Cytometry for Monitoring Multiple Blood Rheology Parameters," Cytometry Part A, Oct. 2011, pp. 746-757, vol. 79, No. 10.
Galanzha, E., et al., "In Vivo Flow Cytometry of Circulating Clots Using Negative Photothermal and Photoacoustic Contrasts," Cytometry Part A, Oct. 2011, pp. 814-824, vol. 79A, No. 10, with Corrigendum, Cytometry Part A, 2011, pp. 1024, vol. 79A, No. 12.
Galanzha, E., et al., "Photoacoustic flow cytometry," Methods, Jul. 2012, pp. 280-296, vol. 57, No. 3, with HHS Public Access Author Manuscript, Mar. 19, 2016, pp. 1-44, Academic Press.
Galanzha, E., et al., "In vivo Magnetic Enrichment, Photoacoustic diagnosis, and Photothermal Purging of Infected Blood Using Multifunctional Gold and Magnetic Nanoparticles," PLoS One, Sep. 2012, pp. 1-14, vol. 7, No. 9, e45557.
Galanzha, E., et al., "Circulating tumor cell detection and capturing using photoacoustic flow cytometry in vivo and ex vivo," Cancers, manuscript, 2013, pp. 1-45, vol. 5.
Galanzha, E., et al., "Photoacoustic and photothermal cytometry using photoswitchable proteins and nanoparticles with ultrasharp resonances," J. Biophoton., Jan. 2015, pp. 81-93, vol. 8, No. 1-2, Wiley-VCH Verlag GmbH & Co. KGaA, Weinheim.
Garrett, T., et al., "Bacterial adhesion and biofilms on surfaces," Progress in Natural Science, 2008, pp. 1049-1056, vol. 18, Elsevier.
Givan, A., "Flow Cytometry, An Introduction," Methods in Molecular Biology, Flow Cytometry Protoco9ls, Second Edition, 2004, pp. 1-31, vol. 263, Humana Press.
Goddard, G., et al., "Ultrasonic Particle-Concentration for Sheathless Focusing of Particles for Analysis in a Flow Cytometer," Cytometry Part A, 2006, pp. 66-74, vol. 69A.
Gutierrez-Juarez, G., et al., "Optical Photoacoustic Detection of Circulating Melanoma Cells in Vitro," Int. J. Thermophys., 2010, pp. 784-792, vol. 31, Springer Science+Business Media, LLC.
Gutierrez-Juarez, G., et al., "Detection of Melanoma Cells in Vitro Using an Optical Detector of Photoacoustic Waves," Laser Surg. Med., 2010, pp. 274-281, vol. 42.
Non-Final Office Action for U.S. Appl. No. 18/105,636, issued Dec. 26, 2023 (81 Pages).
Final Office Action for U.S. Appl. No. 14/668,418, issued May 24, 2017 (24 Pages).
Non-Final Office Action for U.S. Appl. No. 15/240,712, issued Feb. 8, 2019 (97 Pages).
Final Office Action for U.S. Appl. No. 15/240,712, issued Aug. 22, 2019 (23 Pages).
Non-Final Office Action for U.S. Appl. No. 14/939,039, issued Oct. 11, 2019 (22 Pages).
Non-Final Office Action for U.S. Appl. No. 15/240,712, issued Jun. 25, 2020 (40 Pages).
Non-Final Office Action for U.S. Appl. No. 14/939,039, issued Dec. 16, 2020 (21 Pages).
Final Office Action for U.S. Appl. No. 15/240,712, issued Jan. 21, 2021 (44 Pages).
Birtill, D., et al., "Photoacoustic Spectroscopy," Central Laser Facility Annual Report, 2010-2011, Laser for Science Facility-Biology, 25 pages.
Chitnis, P. et al., "Feasibility of optoacoustic visualization of high-intensity focused ultrsound-induced thermal lesions in live tissue," J. Biomed. Opt., Mar./Apr. 2010, pp. 021313-1 to 021313-5, vol. 15, No. 2.
Karpiouk, A, et al., "Combined Ultrasound and Photoacoustic Imaging to Age Deep Vein Thrombosis: Preliminary Studies," IEEE Ultrasonics Symposium, 2005, pp. 399-402, vol. 1.
Karpiouk, A, et al., "Combined ultrasound and photoacoustic imaging to detect and stage deep vein thrombosis: phantom and ex vivo studies," J. Biomed. Opt., Sep./Oct. 2008, pp. 054061-1 to 054061-8, vol. 13, No. 5.
Kim, C., et al., "Deeply penetrating in vivo photoacoustic imaging using a clinical ultrasound array system," Biomed. Opt. Express, Aug. 2010, pp. 278-284, vol. 1., No. 1.
Mallidi, S., et al., "Photoacoustic imaging in cancer detection, diagnosis, and treatment guidance," Trends Biotechnol., May 2011, pp. 213-221, vol. 29, No. 5.
Menyaev, Y., et al., "Preclincial photoacoustic models: application for ultrasensitive single cell malaria diagnosis in large vein and artery," Biomed. Opt. Express, Sep. 1, 2016, pp. 3643-3658, vol. 7, No. 9.
Notice of Allowance for U.S. Appl. No. 17/668,909, issued Mar. 29, 2023 (45 pages).
Office Action dated Dec. 14, 2017 from related U.S. Appl. No. 14/552,143, 9 pages.
Office Action dated Jul. 13, 2018 from related U.S. Appl. No. 14/728,849, 12 pages.
Office Action dated Jul. 13, 2018 from related U.S. Appl. No. 14/552,143, 9 pages.
Office Action dated Aug. 10, 2018 from related U.S. Appl. No. 14/668,418, 16 pages.
Office Action dated Sep. 26, 2018 from related U.S. Appl. No. 14/754,034, 7 pages.
Office Action dated Jan. 11, 2019 from related U.S. Appl. No. 14/728,849, 12 pages.

(56) References Cited

OTHER PUBLICATIONS

Ozkumur, E., et al., "Inertial Focusing for Tumor Antigen-Dependent and -Independent Sorting of Rare Circulating Tumor Cells," NIH Public Access Author Manuscript, available in PMC, Oct. 3, 2013, pp. 1-20, Published in final edited form as: Sci. Tranl. Med., Apr. 3, 2013, pp. 179ra47, vol. 5, No. 179.

Pantel, K., et al., "Detection, clinical relevance and specific biological properties of dissmeninating tumour cells," Nat. Rev. Cancer, May 2008, pp. 329-340, vol. 8, Nature Publishing Group.

Pelan-Mattocks, L., et al., "Flow cytometric analysis of intracellular complexity and CD45 expression for use in rapid differentiation of leukocytes in bovine blood samples," Am. J. Vet Res., Nov. 2001, pp. 1740-1744, vol. 62, No. 11.

Perez-Gutierrez, F., et al., "Plasma Membrane Integrity and Survival of Melanoma Cells After Nanosecond Laser Pulses," Ann. Biomed. Eng., Nov. 2010, pp. 3521-3531, vol. 38, No. 11.

Piyasena, M., et al., "Multinode acoustic focusing for parallel flow cytometry," NIH Public Access Author Manuscript, available in PMC, Feb. 21, 2013, pp. 1-18, Published in final edited form as Anal. Chem., Feb. 21, 2012, pp. 1831-1839, vol. 84, No. 4.

Prahl, S., "Optical Absorption of Hemoglobin," available at http://omlc.ogi.edu/spectra/hemoglobin, Dec. 15, 1999, 4 pages.

Proskurnin, M., et al., "In Vivo Multispectral Photoacoustic and Photothermal Flow Cytometry with Multicolor Dyes: A Potential for Real-Time Assessment of Circulation, Dye-Cell Interaction, and Blood Volume," Cytometry Part A, 2011, pp. 834-847, vol. 79A.

Rai, R., et al., "Nanoparticles and their potential application as antimicrobials," Formatex Microbiology Series No. 3, Dec. 31, 2011, pp. 197-209, vol. 1.

Rao, C., et al., "Circulating melanoma cells and survival in metastatic melanoma," Int. J. Oncol., 2011, pp. 755-760, vol. 38.

Reggiori, G., et al., "Early alteratons of red blood cell rheology in critically ill patients," Crit. Care med., 2009, pp. 3041-3046, vol. 37, No. 12.

Riethdorf, S., et al., "Detection of Ciculating Tumor Cells in Peripheral blood of Patients with Metastatic Breast Cancer: A Validation Study of the CellSearch System," Clin. Cancer Res., Feb. 1, 2007, pp. 920-928, vol. 13, No. 3.

Sarimollaoglu, M., et al., "In vivo photoacoustic time-of-flight velocity measurement of single cells and nanoparticles," NIH Public Access Author Manuscript, available in PMC, Oct. 15, 2012, pp. 1-8, Published in final edited form as: Opt. Lett., Oct. 15, 2011, pp. 4086-4088, vol. 36, No. 20.

Sarimollaoglu, M., et al., "Nonlinear photoacoustic signal amplification from single targets in absorption background," Photoacoustics, Article in Press, 2013, pp. 1-11, vol. 12, Elsevier.

Schmid, T., et al., "Process analysis of biofilms by photoacoustic spectroscopy, Anal. Bioanal. Chem., 2003, pp. 1124-1129, vol. 375.

Schmid, T., et al., "Phtotacoustic absorption spectra of biofilms," Reivew of Scientific Instruments, Jan. 2003, pp. 755-757, vol. 74, No. 1.

Schmidt-Kittler, O., et al., "From latent disseminated ells to overt metastasis: Genetic analysis of systemic cancer progression," PNAS, Jun. 24, 2003, pp. 7737-7742, vol. 100, No. 13.

Setia, N., et al., "Profiling of ABC transporters ABCB5, ABCF2, and nestin-positive stem cells in nevi, in situ and invasive melanoma," Mod. Pathol., 2012, pp. 1169-1175, vol. 25.

Shao, J., et al., "Photothermal nanodrugs: potential of TNF-gold nanospheres for cancer theranostics," Nature Scientific Reports, 2013, pp. 1-9, vol. 3, No. 1293, Nature Publishing Group.

Shashkov, E., et al., "Quantum dots as multimodal photoacoustic and photothermal contrast agents," NIH Public Access Author Manuscript, available in PMC, Nov. 1, 2009, pp. 1-13, Published in final edition form as: Nano Lett., Nov. 2008, pp. 3953-3958, vol. 8, No. 11.

Shashkov, E., et al., "Photothermal and photoacoustic Raman cytometry in vitro and in vivo," Opt. Exp., Mar. 29, 2010, pp. 6929-6944, vol. 18. No. 7.

Shibue, T., et al., "Metastatic colonization: Settlement, adaptation and propagaton of tumor cells in a foreign tissue environment," Semin. Cancer Biol., 2011, pp. 99-106, vol. 21, Elsevier Ltd.

Sieuwerts, A., et al., "Anti-epithelial Cell Adhesion Molecule Antibodies and the Detection of Circulating Normal-Like Breast Tumor Cells," J. Natl. Cancer Inst., Jan. 7, 2009, pp. 61-66, vol. 101. No. 1.

Sleeman, J., et al., "Do all roads lead to Rome? Routes to metastasis development," Int. J. Cancer, 2011, pp. 2511-2526, vol. 128.

Stott, S., et al., "Isolation of circulating tumor cells using a microvertex-generating herringbone-chip," PNAS, Oct. 26, 2010, pp. 18392-18397, vol. 107, No. 43.

Tamaki, E., et al., "Single-Cell Analysis by a Scanning Thermal Lens Microscope with a Microchip: Direct Monitoring of Cytochrome c Distribution during Apoptosis Process," Anal. Chem., Apr. 1, 2002, pp. 1560-1564, vol. 74, No. 7.

Tanev, S., et al., "Flow Cytometry with Gold Nanoparticles and their Clusters as scattering Contrast Agents: FDTD Simulation of Light-Cell Interaction," NIH Public Access Author Manuscript, available in PMC, Sep. 1, 2010, pp. 1-24, Published in final edited form as: J. Biophotonics, Sep. 2009, pp. 505-520, vol. 2, Nos. 8-9.

Tibbe, A., et al., "Statistical Considerations for Enumeration of Circulating Tumor Cells," Cytometry Part A Office Action dated Nov. 30, 2011 from related U.S. Appl. No. 12/334,217, 12 pages.p. 154-162, vol. 71A.

Tokeshi, M., et al., "Determination of subyoctomole Amounts of Nonfluorescent Molecules Using a Thermal Lens Microscope: Subsingle-Molecule Determination," Anal. Chem., May 1, 2001, pp. 2112-2116, vol. 73, No. 9.

Tuchin, V., et al., "Towards in vivo flow cytometry," HHS Public Access Author Manuscript, available in PMC, Mar. 2, 2016, pp. 1-4, Published in final edited form as: J. Biophotonics, Sep. 2009, pp. 457-458, vol. 2, No. 0.

Tuchin, V., et al., "In Vivo Flow Cytometry: A Horizon of Opportunities," Cytometry Part A, 2011, pp. 737-745, vol. 79A.

Aguirre-Ghiso, J., "On the theory of self-seeding: implications for metastasis progression in humans," Breast Cancer Res., 2010, pp. 1-2, vol. 12, No. 304.

Al-Hajj, M., et al., "Prospective identification of tumorigenic breast cancer cells," PNAS, Apr. 1, 2003, pp. 3983-3988, vol. 100, No. 7, with Correction, PNAS, May 27, 2003, pp. 6890-6891, vol. 100, No. 11.

Alexander, J., "The Normal Blood Clotting Time in the Light of Experience with the 'Two-syringe' Technique," J. Clin. Pathol., 1955, pp. 227-228, vol. 8.

Alix-Panabieres, C., et al., "Circulating Tumor Cells and Circulating Tumor DNA," Annu. Rev. Med., 2012, pp. 199-215, vol. 63.

Alix-Panabieres, C., et al., "Circulating Tumor Cells: Liquid Biopsy of Cancer," Clin. Chem., 2013, pp. 110-118, vol. 59, No. 1.

Allan, A., et al., "Detection and Quantification of Circulating Tumor Cells in Mouse Models of Human Breast Cancer Using Immunomagnetic Enrichment and Multiparameter Flow Cytometry," Cytometry Part A, May 2005, pp. 4-14, vol. 65A., No. 1, Wiley-Liss, Inc.

Alunni-Fabbroni, M., et al., "Circulating tumor cells in clinical practice: Methods of detection and possible characterization," Methods, 2010, pp. 289-297, vol. 50, Elsevier Inc.

Ara, G., et al., "Irradiation of Pigmented Melanoma Cells with High Intensity Pulsed Radiation Generates Acoustic Waves and Kills Cell," Lasers in Surgery and Medicine, 1990, pp. 52-59, vol. 10, No. 1.

Autebert, J., et al., "Microfluidic: an innovative tool for efficient cell sorting," Methods, 2012, pp. 297-307, vol. 57, No. 3, Elsevier.

Baeuerle, P., et al., "EpCAM (CD326) finding its own role in cancer," Br. J. Cancer, Feb. 12, 2007, pp. 417-423, vol. 96.

Berciaud, S., et al., "Photothermal Heterodyne Imaging of Individual Nonfluorescent Nanoclusters and Nanocrystals," Phys. Rev. Lett., Dec. 17, 2004, pp. 257402-1 to 257402-4, vol. 93.

Bhattacharyya, B., et al., "Gold nanoparticle-mediated detection of circulating cancer cells," NIH Public Access Author Manuscript, available in PMC, Mar. 1, 2013, pp. 1-18, Published in final form as: Clin. Lab. Med., Mar. 2012, pp. 89-101, vol. 32, No. 1.

(56) References Cited

OTHER PUBLICATIONS

Bhattacharyya, K., et al., "Detection, isolation, and capture of circulating brewast cancer cells with photoacoustic flow cytometry," Proc. SPIE, 2013, 9 pages, vol. 8570A.

Office Action dated Nov. 16, 2023 from related U.S. Appl. No. 17/668,971, 8 pages.

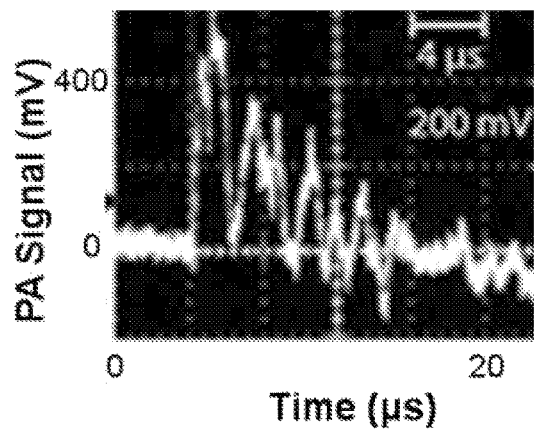
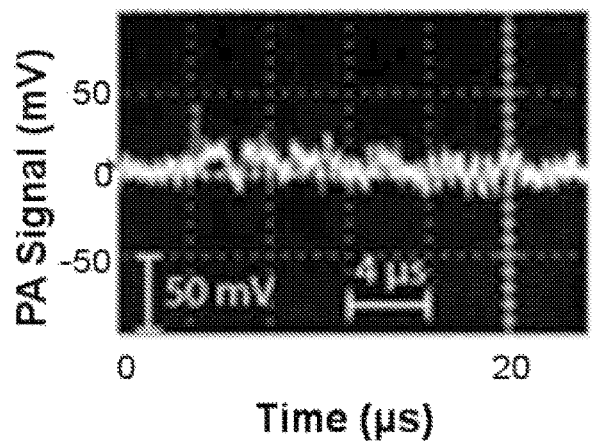
FIG. 49A  FIG. 49B
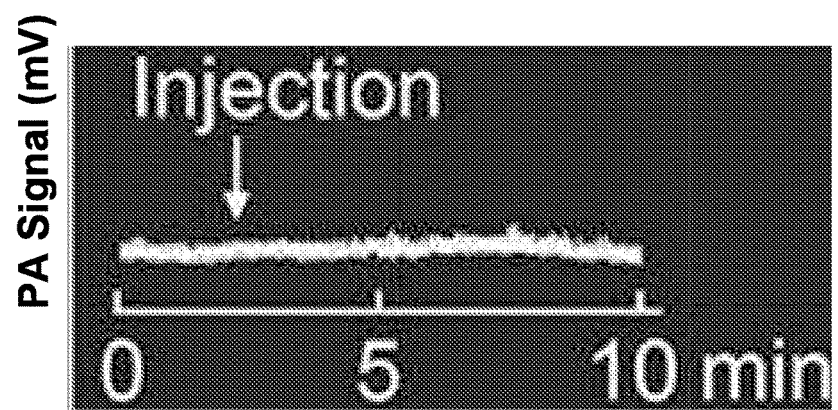
FIG. 50

DEVICE AND METHOD FOR IN VIVO PHOTOACOUSTIC DIAGNOSIS AND PHOTOTHERMAL PURGING OF INFECTED BLOOD

CROSS REFERENCE TO RELATED APPLICATION

This application is a continuation of U.S. application Ser. No. 17/668,909, filed Feb. 10, 2022, which is a continuation of U.S. application Ser. No. 16/272,798, filed Feb. 11, 2019, which is a continuation of U.S. application Ser. No. 14/668,418, filed Mar. 25, 2015, claims priority from PCT Application No. PCT/US2013/061673 filed on Sep. 25, 2013, which claims priority to U.S. provisional patent Application No. 61/705,491, entitled "A Device and Method for In vivo Photoacoustic Diagnosis and Photothermal Purging of Infected Blood" filed on Sep. 25, 2012.

GOVERNMENTAL RIGHTS

This invention was made with government support under AI093126 awarded by the National Institutes of Health. The government has certain rights in the invention.

FIELD OF THE INVENTION

This application relates to methods of non-invasively detecting and purging bacterial cells using a modified photoacoustic in vivo flow cytometer device. In particular, this application relates to methods of detecting bacterial cells by analyzing photoacoustic pulses emitted in response to laser pulses from a pulsed laser source and/or selectively destroying the detected bacterial cells using a non-linear photothermal response induced by a high-energy laser pulse.

BACKGROUND

The risk posed by the growing prevalence of antibiotic resistance is a pressing threat to public health, making bacterial infections a major problem worldwide. One of the most devastating types of infection is bacteremia, which has the potential to cause life-threatening septic shock and lead to metastatic foci of infection. The pathogen most likely to be associated with a fatal outcome is *Staphylococcus aureus*. Particularly problematic are methicillin-resistant *S. aureus* (MRSA) strains, which have a mortality rate in bacteremic patients as high as 30%.

One approach to addressing this problem is the development of new antimicrobial agents, but this is a time-consuming, costly process that has been de-prioritized by pharmaceutical companies and is currently at a historic low. An attractive alternative would be to develop therapeutic strategies for the physical destruction of bacterial pathogens irrespective of their antibiotic resistance status. Advanced treatment methods such as photodynamic therapy, photo-ultrasound treatment, and nanotechnology-based methods have been investigated primarily in the context of solid tumors. To date, little research has been directed to the use of these advanced methods for the treatment of bacteremia.

Various in vivo flow cytometry techniques take advantage of the single file movement of blood cells through the majority of blood vessels during normal circulation to detect various circulating cells and other target objects moving through vessels non-invasively. To date, these in vivo flow cytometry techniques have been used to detect circulating tumor cells and clots. However, to date, this promising technique has not yet been applied to the treatment of bacteremia.

A need exists for a non-invasive and in vivo technique for detecting and destroying circulating bacterial cells in superficial or deep vessels with sufficient sensitivity to detect individual bacterial cells. Such a technique will make possible the non-invasive selection and killing of bacterial cells in blood vessels regardless of their antibiotic resistance status.

SUMMARY

In an aspect, a method for detecting a circulating bacterial cell within a vessel of a living organism in vivo is provided that includes injecting or transfusing at least one contrast agent into the vessel. The at least one contrast agent is functionalized with at least one targeting agent. The method also includes contacting the circulating bacterial cell with the functionalized contrast agent, pulsing an area of interest with at least one pulse of NIR laser energy, and detecting at least one photoacoustic pulse emitted by the bacterial cell. The method further includes analyzing the at least one detected photoacoustic pulse to indicate the presence of the bacterial cell in circulation.

In an aspect, circulating bacterial cells are detected at a resolution of at least 1 bacterial cell per $10^8$ cells in circulation. The at least one contrast agent may be gold nanospheres, gold nanoshells, gold nanorods, gold cages, carbon nanoparticles, perfluorocarbon nanoparticles, carbon nanotubes, spectrally tunable golden carbon nanotubes, carbon nanohorns, magnetic nanoparticles, silica-coated magnetic nanoparticles, quantum dots, binary gold-carbon nanotube nanoparticles, multilayer nanoparticles, clustered nanoparticles, liposomes, micelles, or microbubbles. The at least one targeting agent is an antibody, a protein, a ligand for one or more specific cell receptors, a receptor, a peptide, or a wheat germ agglutinin. In particular, the at least one targeting agent may be selected from antibodies to protein A receptors of *Staphylococcus aureus*, antibodies to a lipoprotein, ligands to polysaccharide and siderophore receptors of bacteria, or an antibody specific for a protein highly expressed in bacteria but absent in mammalian cells. In an aspect, more than one targeting agent functionalizes one contrast agent. In another aspect, one targeting agent functionalizes more than one contrast agent. In yet another aspect, more than one targeting agent functionalizes more than one contrast agent in various combinations. The method may further include continuously withdrawing a portion of blood from the vessel of the living organism to an extracorporeal shunt comprising a circulatory bypass tube, directing the portion of blood through the circulatory bypass tube, and returning the portion of blood back into the vessel of the living organism. The area of interest includes a cross-section situated within the circulatory bypass tube.

In another aspect, a method for selectively destroying a plurality of circulating bacterial cells in a vessel of a living organism in vivo is provided. The method includes injecting or transfusing at least one contrast agent into the vessel. The at least one contrast agent is functionalized with at least one targeting agent. The method also includes contacting the plurality of circulating bacterial cells with the functionalized contrast agent, detecting one or more of the plurality of circulating bacterial cells, and triggering a pulse of laser energy delivered at a wavelength and energy level sufficient to cause the destruction of the one or more detected bacterial cells. The method further includes monitoring a frequency of detection of a remaining portion of circulating bacterial cells through the vessel and terminating when the frequency of detection of the remaining portion of circulating bacterial cells falls below a threshold level.

In this aspect, the one or more of the plurality of circulating bacterial cells are detected using an in vivo flow cytometry device using laser-excited photoacoustic waves emitted by the one or more of the plurality of circulating bacterial cells. The threshold level of the frequency of detection ranges between about $10^{-3}$ target objects/min and about $10^2$ target objects/min. The at least one contrast agent is selected from gold nanospheres, gold nanoshells, gold nanorods, gold cages, carbon nanoparticles, perfluorocarbon nanoparticles, carbon nanotubes, spectrally tunable golden carbon nanotubes, carbon nanohorns, magnetic nanoparticles, silica-coated magnetic nanoparticles, quantum dots, binary gold-carbon nanotube nanoparticles, multilayer nanoparticles, clustered nanoparticles, liposomes, micelles, or microbubbles. The at least one targeting agent is an antibody, a protein, a ligand for one or more specific cell receptors, a receptor, a peptide, or a wheat germ agglutinin. In particular, the at least one targeting agent may be selected from the group consisting of antibodies to protein A receptors of *Staphylococcus aureus*, antibodies to a lipoprotein, ligands to polysaccharide and siderophore receptors of bacteria, or an antibody specific for a protein highly expressed in bacteria but absent in mammalian cells. In an aspect, more than one targeting agent functionalizes one contrast agent. In another aspect, one targeting agent functionalizes more than one contrast agent. In yet another aspect, more than one targeting agent functionalizes more than one contrast agent in various combinations. A first wavelength may be used with a first contrast agent to detect the one or more of the plurality of circulating bacterial cells and a second wavelength may be used with a second contrast agent to destroy the one or more detected bacterial cells. The method may further include continuously withdrawing a portion of blood from the vessel out of the living organism to an extracorporeal shunt comprising a circulatory bypass tube, directing the portion of blood through the circulatory bypass tube, and returning the portion of blood back into the vessel of the living organism. The area of interest includes a cross-section situated within the circulatory bypass tube.

In yet another aspect, a method for selectively destroying a plurality of circulating bacterial cells in a vessel of a living organism in vivo is provided. The method includes injecting or transfusing at least one contrast agent into the vessel. The at least one contrast agent is functionalized with at least one targeting agent. The method also includes triggering a pulse of laser energy delivered at a wavelength and energy level sufficient to cause the destruction of one or more of the plurality of circulating bacterial cells. The method further includes monitoring a frequency of destruction of the plurality of circulating bacterial cells and terminating when the frequency of destruction of circulating bacterial cells falls below a threshold level.

In this aspect, the threshold level of the frequency of destruction ranges between about $10^{-3}$ target objects/min and about $10^2$ target objects/min. The at least one contrast agent is selected from gold nanospheres, gold nanoshells, gold nanorods, gold cages, carbon nanoparticles, perfluorocarbon nanoparticles, carbon nanotubes, spectrally tunable golden carbon nanotubes, carbon nanohorns, magnetic nanoparticles, silica-coated magnetic nanoparticles, quantum dots, binary gold-carbon nanotube nanoparticles, multilayer nanoparticles, clustered nanoparticles, liposomes, micelles, or microbubbles. The at least one targeting agent is an antibody, a protein, a ligand for one or more specific cell receptors, a receptor, a peptide, or a wheat germ agglutinin. In particular, the at least one targeting agent may be selected from antibodies to protein A receptors of *Staphylococcus aureus*, antibodies to a lipoprotein, ligands to polysaccharide and siderophore receptors of bacteria, or an antibody specific for a protein highly expressed in bacteria but absent in mammalian cells. In an aspect, more than one targeting agent functionalizes one contrast agent. In another aspect, one targeting agent functionalizes more than one contrast agent. In yet another aspect, more than one targeting agent functionalizes more than one contrast agent in various combinations. The method may further include continuously withdrawing a portion of blood from the vessel out of the living organism to an extracorporeal shunt comprising a circulatory bypass tube, directing the portion of blood through the circulatory bypass tube, and returning the portion of blood back into the vessel of the living organism. The area of interest includes a cross-section situated within the circulatory bypass tube.

While multiple embodiments are disclosed, still other embodiments of the present disclosure will become apparent to those skilled in the art from the following detailed description, which shows and describes illustrative embodiments of the disclosure. As will be realized, the invention is capable of modifications in various aspects, all without departing from the spirit and scope of the present disclosure. Accordingly, the drawings and detailed description are to be regarded as illustrative in nature and not restrictive.

BRIEF DESCRIPTION OF THE DRAWINGS

(FIG. 3A) from blood flow in a rat ear vessel with diameter of 50 µm, (FIG. 3B) from skin surrounding a rat ear vessel before dye injection, (FIG. 3C) from blood flow in a rat ear vessel 5 min after the injection of Lymphazurin, and (FIG. 3D) from the skin surrounding a rat ear vessel measured 20 min after dye injection.

FIG. 13A-FIG. 13C shows oscilloscope traces of the two-wavelength, time-resolved detection of PA signals from: (FIG. 13A) necrotic lymphocytes labeled with gold nanorods absorbing 639 nm laser pulses, (FIG. 13B) apoptotic lymphocytes labeled with gold nanoshells absorbing 865 nm laser pulses, and (FIG. 13C) live neutrophils labeled with carbon nanotubes absorbing both the 639 nm and the 865 nm laser pulses.

FIG. 14A-FIG. 14B shows oscilloscope traces of the two-wavelength, time-resolved detection of PA signals from: (FIG. 14A) melanoma cells absorbing 865 nm and 639 nm laser pulses, and (FIG. 14B) red blood cells absorbing 865 nm and 639 nm laser pulses.

FIG. 23A is a fluorescent microscopic image of the suspension with no external magnetic field applied. FIG. 23B is a fluorescent microscopic image of the same suspension after the end of a magnet is attached to the top of the slide cover.

FIG. 24A is a non-linear photothermal (PT) signal obtained from the suspension with no external magnetic field applied. FIG. 24B is a non-linear photothermal (PT) signal obtained from the same suspension after the end of a magnet is attached to the top of the slide cover.

FIG. 25A is a fluorescent microscopic image of the labeled cancer cell with no external magnetic field applied. FIG. 25B is a fluorescent microscopic image of the same labeled cancer cell after the end of a magnet is attached to the top of the slide cover.

FIG. 26A is a non-linear photothermal (PT) signal obtained from the labeled cancer cell with no external magnetic field applied. FIG. 26B is a non-linear photothermal (PT) signal obtained from the same labeled cancer cell after the end of a magnet is attached to the top of the slide cover.

FIG. 49A is an oscilloscope trace of a PA signal produced by an unlabeled bacteria cell, and FIG. 49B is an oscilloscope trace of the background PA signals.

FIG. 50 is an oscilloscope trace of PA signals produced by unlabeled bacteria cells measured in the mouse abdominal vessel model.

Corresponding reference characters indicate corresponding elements among the views of the drawings. The headings used in the figures should not be interpreted to limit the scope of the claims.

DETAILED DESCRIPTION

The present disclosure provides a theranostic device and a method of using the theranostic device to detect and destroy bacterial cells in vivo. In an aspect, the theranostic device may include an in vivo flow cytometer that may be any known in vivo flow cytometer, including, but not limited to, the photoacoustic flow cytometry (PAFC) device described in U.S. patent application Ser. No. 12/334,217, the contents of which are incorporated herein in their entirety. Although any in vivo flow cytometer may be included in the theranostic device, the device will be described herein assuming the inclusion of a PAFC.

Figure 1:
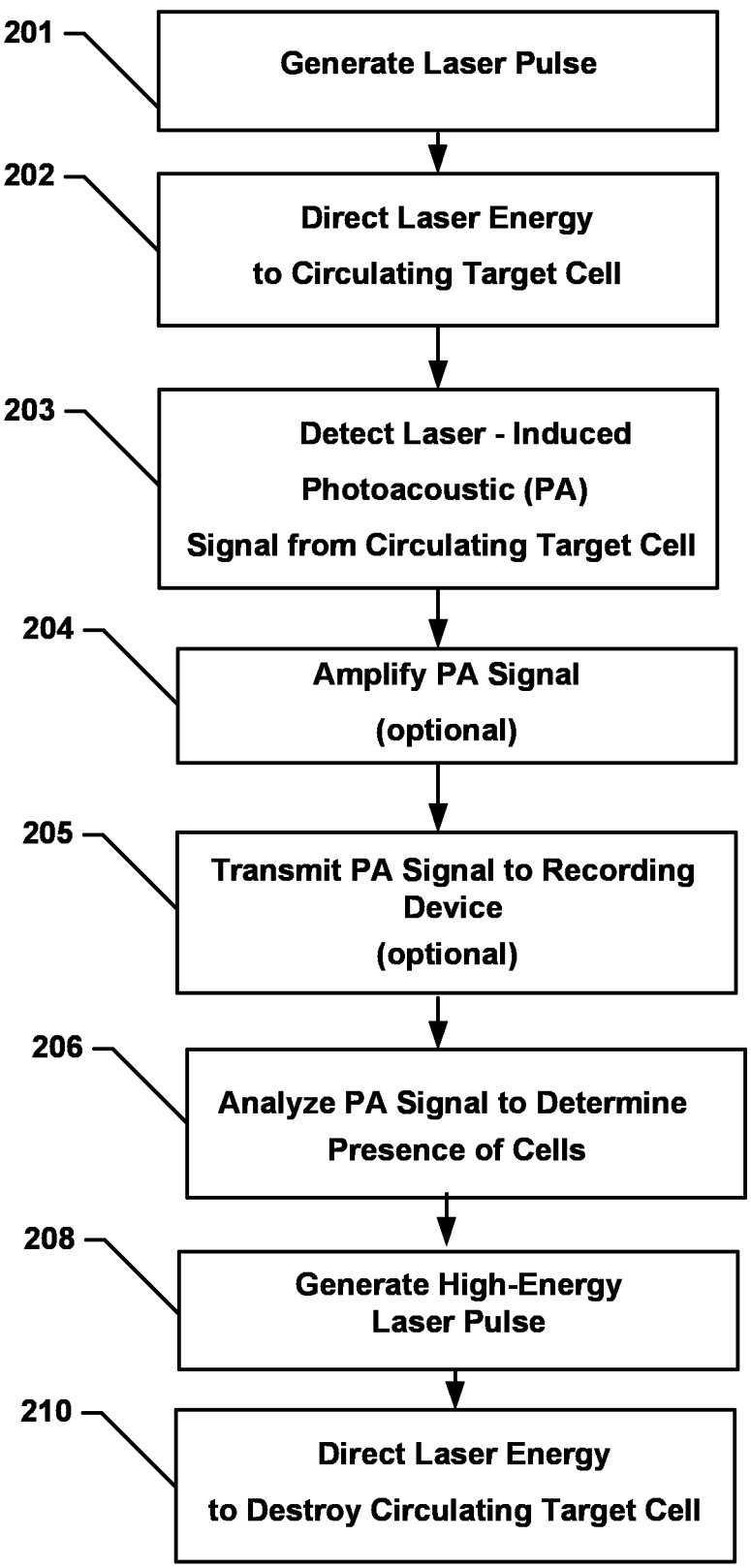
FIG. 1 is a flow chart of the photoacoustic in vivo flow cytometry method.

Referring to FIG. 1, the theranostic device detects target objects in a moving biofluid by generating a laser pulse at step 201 and directing the laser energy resulting from the laser pulse to the area of interest containing the circulating target cell at step 202. The target cell, in this aspect a bacterial cell which may either possess intrinsic photoacoustic (PA) properties or may be labeled with a PA contrast agent, emits a PA signal that is detected at step 203. The detected PA signal may be amplified at step 204, recorded at step 205, and analyzed at step 206 to determine the presence of the target cell in the area of interest. A high-energy laser pulse may be generated at step 208 and directed to the target cell in order to destroy the target cell at step 210.

Figure 2:
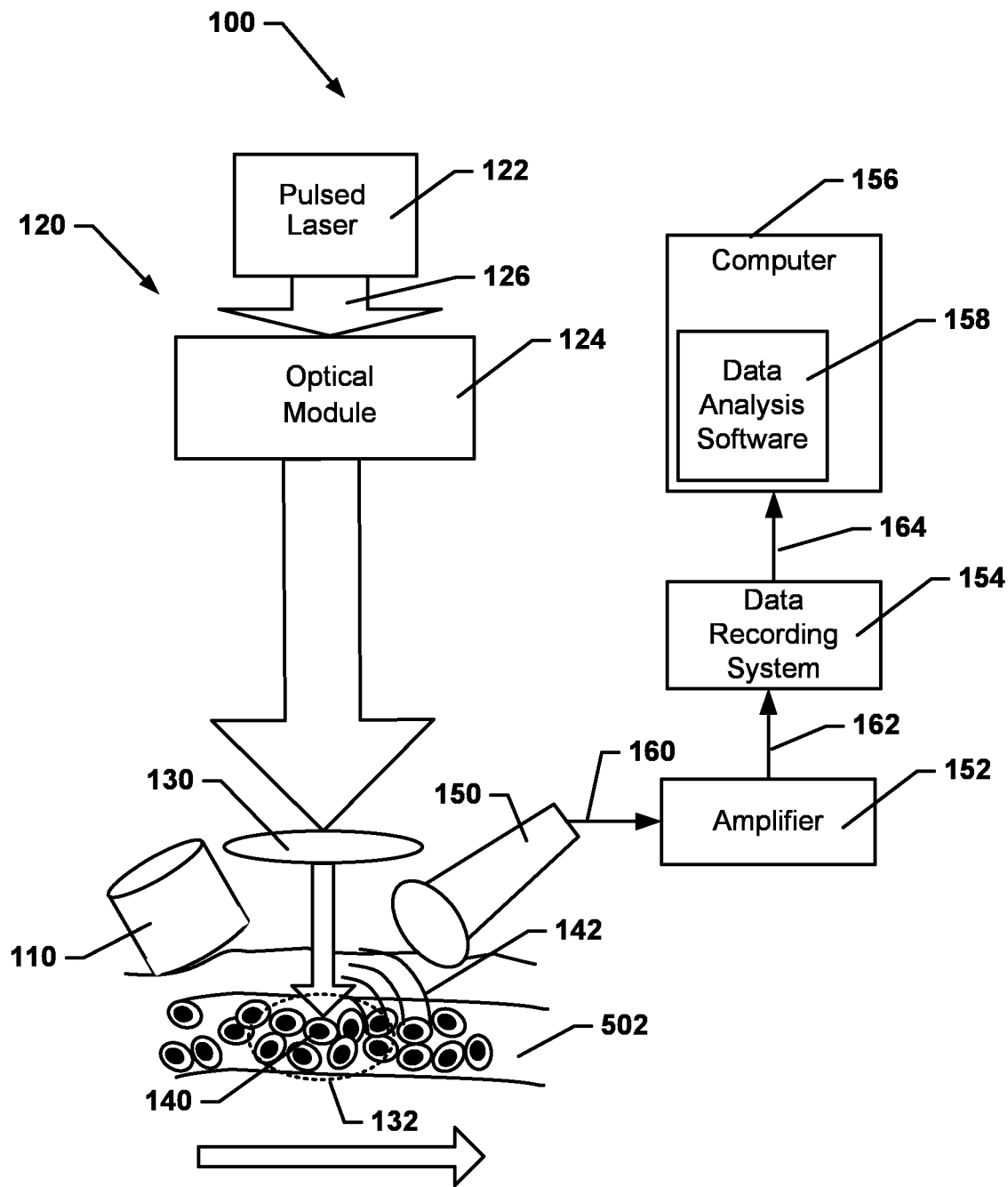
FIG. 2 is a diagram illustrating the in vivo flow cytometry device in an aspect.
Figure 3A:
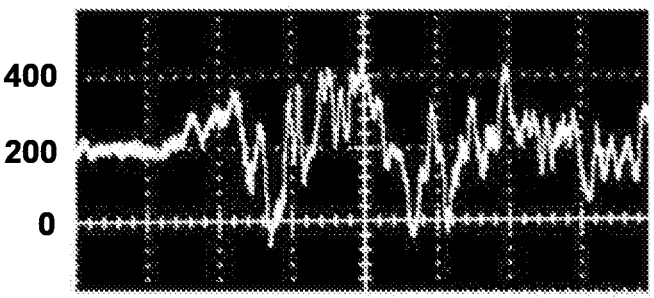
FIG. 3A-FIG. 3D shows the oscilloscope trace recordings of PA signals.
Figure 3B:
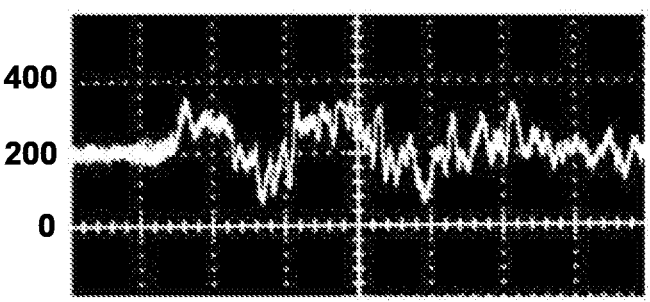
Figure 3C:
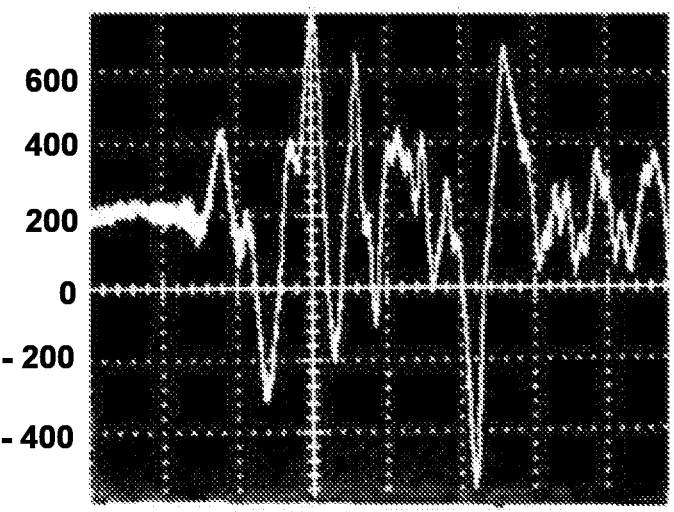
Figure 3D:
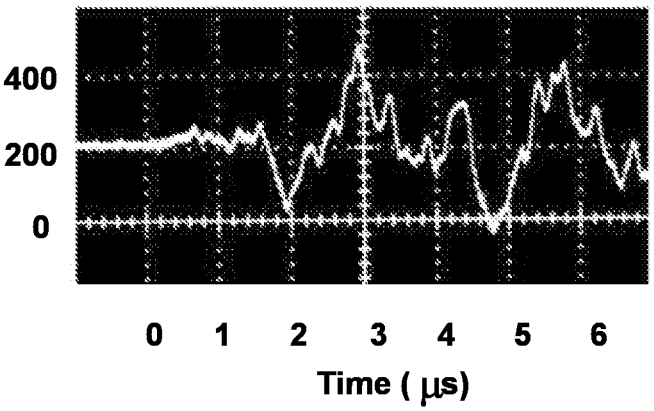

Referring to FIG. 2, in one aspect the theranostic device 100 includes an in vivo flow cytometer 120 used to detect the presence of target objects 140 within the area of interest 132 of a moving biofluid 502. In this aspect, the in vivo flow cytometer 120 may be a PAFC that includes a pulsed laser 122 capable of emitting laser energy 126 ranging between wavelengths of about 400 nm and about 2500 nm, and may further include an optical module 124 to convert the wavelength, pulse duration, or both wavelength and pulse duration emitted by the pulsed laser 122 to desired values. In this aspect, the pulsed laser 122 may produce a low energy pulse for the detection of a target object 140 and/or a high-energy laser pulse to destroy the target object 140. For example, a Raman shifter may be used to deliver a probe pulse having a wavelength and pulse duration that are different from the pump pulse received from the pulsed laser 122. In addition, the in vivo flow cytometer 120 may further include optical elements 130 such as lenses or optic fibers to direct the laser energy 126 to the target objects 140. The in vivo flow cytometer 120 may also include at least one ultrasound transducer 150 to detect photoacoustic waves 142 emitted by the target objects 140. The device 100 may optionally include an amplifier 152, a data recording system 154, and a computer 156 with stored data analysis software 158.

The device 100 may further include a magnet 110 situated in close proximity to the area of interest 132 such that the magnetic field induced by the magnet 110 alters the movement of the target objects flowing past the area of interest 132, as shown in FIG. 2. The target objects 140 may be intrinsically magnetic or may be labeled with attached magnetic particles, rendering them susceptible to the forces induced by a magnetic field produced by the magnet 110. The magnetic field may manipulate the target objects 140 within the area of interest 132. Non-limiting examples of manipulations of the target objects 140 include: immobilization, enrichment, sorting, separating, concentration within a selected region of the biofluid, and combinations thereof within the area of interest 132.

The device 100 is operated by illuminating a circulating target object 140 with laser energy pulses 132, thereby inducing the target objects 140, for example bacteria cells, to emit a photoacoustic (PA) signal 142. The PA signal 142 is typically in the ultrasound spectrum, with a range of frequencies between about 20 kHz and about 200 MHz. The PA signal 142 emitted by the target objects 140 may result from the absorption of laser pulse 132 energy by a variety of mechanisms including, but not limited to single photon absorption, two photon absorption, multi-photon absorption, Coherent Anti-Stokes Raman Scattering (CARS), and combinations thereof.

The ultrasound transducer 150 detects the PA signal 142 emitted by the target object 140, and the output 160 from the ultrasound transducer 150 is analyzed using data processing software 158 to identify the presence of the target objects 140. In an aspect, an amplifier 152 may amplify the output 160 of the ultrasound transducer 150. In an aspect, the amplified signal 164 may be stored in a data recording system 154. In an aspect, the computer 156 may access the stored signal data 164 for analysis using the data analysis software 158.

Because the ultrasound waves of the PA signals travel freely through most biological tissues, the PAFC device 100 may be used to detect circulating target objects 140 in circulatory and lymphatic vessels as deep as 15 cm below the external surface of the organism. Further, because the laser power used by the PAFC device 100 is relatively low due to the efficient absorption of laser light by target objects 140, in vivo PAFC may be conducted for extended time periods with minimal damage to any circulating cells. The PAFC may be used for the continuous monitoring of circulating cells for the early diagnosis and treatment of metastasis, inflammations, sepsis, immunodeficiency disorders, strokes, or heart attacks.

In other aspects, the in vivo flow cytometer 120 may utilize one or more known detection methods to detect the target objects 140. Non-limiting cell detection methods suitable for use by an in vivo flow cytometer 120 include photoacoustic methods, photothermal methods, fluorescent methods, Raman and other scattering methods, and any combination thereof.

As shown in FIG. 48, the in vivo flow cytometer 120 may detect target objects 140 in a moving biofluid 502 flowing through an extracorporeal shunt 500. The extracorporeal shunt 500 directs the moving biofluid 502 from an afferent circulatory vessel 504 such as an artery within the integument 506 of an organism to a circulatory bypass tube 508 outside of the organism. The target objects 140 may be detected as they move through an area of interest 132 by the in vivo flow cytometer 120. The moving biofluid 502 is returned back into an efferent circulatory vessel 510 such as a vein within the integument 506 of an organism. A pump 516 such as a peristaltic pump may be further included to move the biofluid 502 through the circulatory bypass tube 508. A high speed high resolution imaging mode optical system 518 may be used to provide visualization of individual moving cells at single cell level, as well as to guide the placement of the elements of the in vivo flow cytometer 120. Other aspects of the extracorporeal shunt 500, such as the manipulation of the movement of the target objects 140 using magnets 110G and 110H, are discussed in further detail below.

If the target objects 140 are immobilized within the area of interest 132, either within the organism or within an extracorporeal shunt 500, other methods and devices in addition to an in vivo flow cytometer 120 may be used to detect and characterize the target objects 140. Non-limiting examples of suitable devices for the detection and characterization of immobilized target objects 140 include MRI, CT, PET, ultrasound, and conventional or fluorescent microscopy devices.

Figure 46:
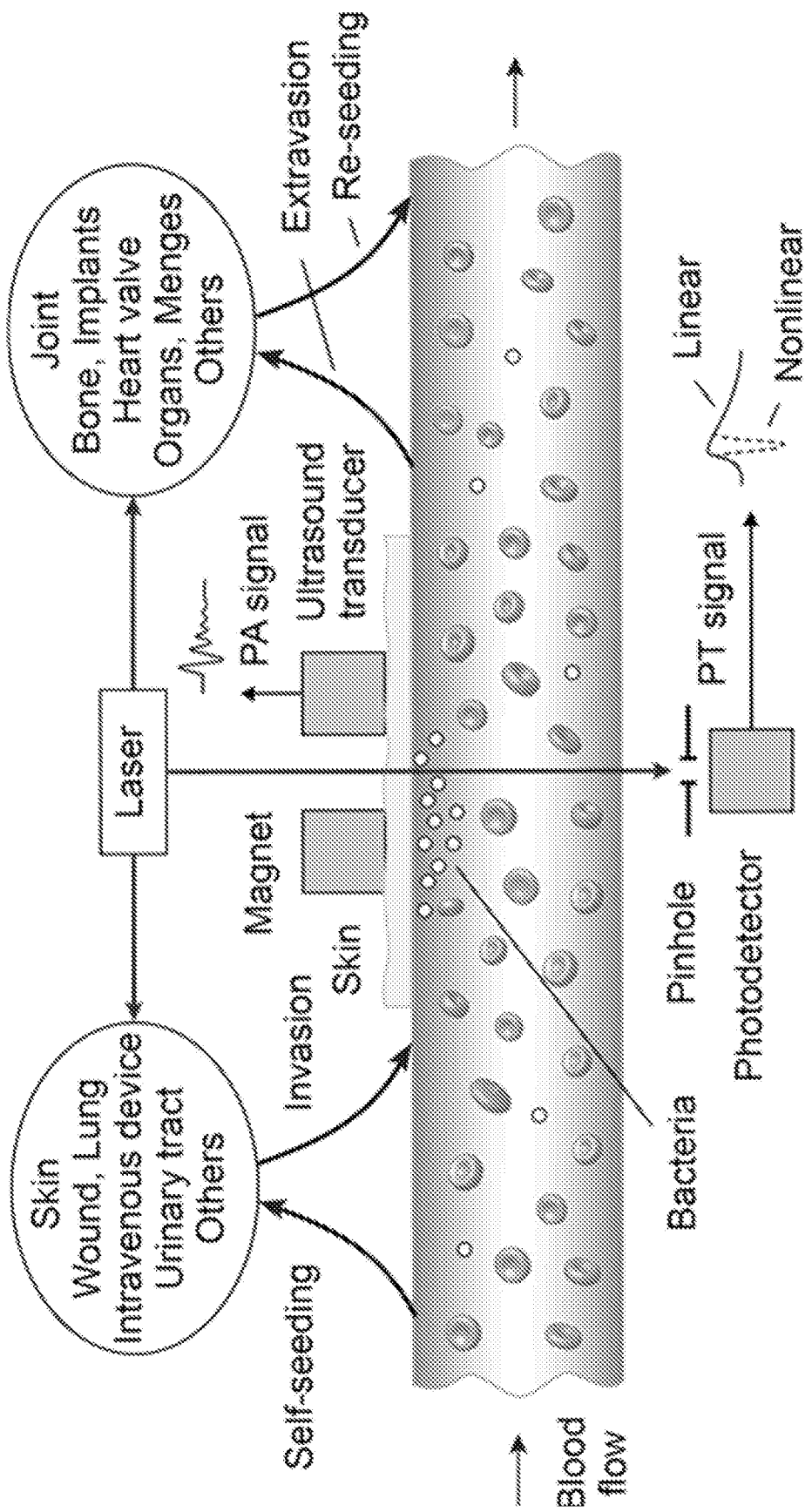
FIG. 46 is a schematic diagram illustrating the principle of in vivo integrated PA-PT nano-theranostics of bacteria in blood and distant infected sites.

FIG. 46 is a schematic diagram illustrating the principle of in vivo integrated PA/PT nano-theranostics of bacteria in blood and distant infected sites. Without being limited to any particular theory, the bacterial infection may be characterized by an initial invasion via the skin, mucous membrane, or other exterior boundary of the organism. The infection may propagate by a process of invasion, extravasation, and/or re-seeding. In invasion, bacterial cells migrate from a locally infected tissue into the blood flow; the locally infected tissue may be associated with the initial infection due to a wound, an intravenous device, a urinary tract infection, a lung infection, or any other known bacterial infection. The bacterial cells may leave the bloodstream to infect surrounding tissues that may be different from the initial local infection site in the extravasation process. The extravasated cells may propagate in the secondary infection region and may renter the blood flow in the reseeding process. In an aspect, the PA/PT nano-theranostics method monitors the bacteria moving though a vessel using the PA/PT detection methods described herein. In addition, the theranostic method may deliver high-energy pulses at selected wavelengths and pulse energy fluences to selectively destroy the bacteria cells. In this aspect, the laser wavelength may be selected based on the enhanced absorbance of the bacteria cell, which may be labeled with a contrast agent such as a functionalized nanoparticle, relative to the surrounding cells and tissues. The functionalized nanoparticle may include any of the nanoparticle contrast agents described herein, in which the nanoparticle is further complexed with a bacteria-specific targeting molecule such as an antibody raised against a bacterial surface protein, phospholipid, biomarker, or any other molecular or other bacterial feature.

I. Target Objects

The method of the present disclosure may be used to detect target objects 140 circulating in vessels, defined herein as circulatory and lymphatic vessels at a depth between about 10 µm and about 15 cm below the surface of the skin and may include capillaries, arterioles, venules, arteries, veins, lymphatic vessels, hyphae, phloem, xylem, and sinuses. The diameters of the vessels may range between about 10 µm and about 2 cm. The vessels may be located in many different organs and tissues, including, but not limited to skin, lips, eyelid, interdigital membrane, retina, ear, nail pad, scrotum, lymph nodes, brain, breast, prostate, lung, colon, spleen, liver, kidney, pancreas, heart, testicles, ovaries, lungs, uterus, skeletal muscle, smooth muscle, and bladder.

In an aspect, the at least one laser pulse 132 may be directed to a single location along one vessel, to two or more locations along a single vessel simultaneously, to two or more locations along a single vessel at two or more times, or simultaneously to locations on two or more vessels.

The method of the present disclosure may be used on organisms that possess cells circulating in vessels or sinuses, from the group of organisms including mammals, reptiles, birds, amphibians, fish, plants, fungi, mollusks, insects, arachnids, annelids, arthropods, roundworms, and flatworms.

The target objects 140 detected by the method of the present disclosure may be at least one target object 140 including but not limited to unlabeled biological cells, biological cell products, unbound contrast agents, biological cells labeled using contrast agents, and any combination thereof. The target objects 140 can be unlabeled endogenous or exogenous biological cells or cell products including but not limited to normal, apoptotic and necrotic red blood cells and white blood cells; aggregated red blood cells or clots; infected cells; inflamed cells; stem cells; dendritic cells; platelets; metastatic cancer cells resulting from melanoma, leukemia, breast cancer, prostate cancer, ovarian cancer, and testicular cancer; bacteria; viruses; fungal cells; protozoa; microorganisms; pathogens; animal cells; plant cells; and leukocytes activated by various antigens during an inflammatory reaction and combinations thereof.

The target objects 140 that are unlabeled biological cells may possess intrinsic cell-specific markers from the group comprised of hemoglobin (Hb), HbH, $HbO_2$, metHb, HbCN, HbS, HbCO, HbChr, myoglobins, melanin, cytochromes, bilirubin, catalase, porphyrins, chlorophylls, flavins, carotenoids, phytochromes, psoralens and combinations thereof.

The target objects 140 may also be biological cell products, including but not limited to products resulting from cell metabolism or apoptosis, cytokines or chemokines associated with the response of immune system cells to infection, exotoxins and endotoxins produced during infections, specific gene markers of cancer cells such as tyrosinase mRNA, p97, MelanA/Mart1 produced by melanoma cells, PSA produced by prostate cancer, and cytokeratins produced by breast carcinoma.

The target objects 140 may also be contrast agents from the group comprised of indocyanine green dye, melanin, fluorescein isothiocyanate (FITC) dye, Evans blue dye, Lymphazurin dye, trypan blue dye, methylene blue dye, propidium iodide, Annexin, Oregon Green, C3, Cy5, Cy7, Neutral Red dye, phenol red dye, AlexaFluor dye, Texas red dye, gold nanospheres, gold nanoshells, gold nanorods, gold cages, carbon nanoparticles, perfluorocarbon nanoparticles, carbon nanotubes, spectrally tunable golden carbon nanotubes, carbon nanohorns, magnetic nanoparticles, silica-coated magnetic nanoparticles, quantum dots, binary gold-carbon nanotube nanoparticles, multilayer nanoparticles, clustered nanoparticles, liposomes, liposomes loaded with contrast dyes, liposomes loaded with nanoparticles, micelles, micelles loaded with contrast dyes, micelles loaded with nanoparticles, microbubbles, microbubbles loaded with contrast dyes, microbubbles loaded with nanoparticles, dendrimers, aquasomes, lipopolyplexes, nanoemulsions, polymeric nanoparticles, and combinations thereof.

The target objects 140 may also be labeled living cells from the list above, marked with targeting agents, molecular markers and tags comprised of contrast agents selected from the list above. In an aspect, a contrast agent may be functionalized with a targeting agent. The targeting agents, molecular markers, or tags may be attached to the cells without modification, or the contrast agents may be functionalized for binding to the cells using molecules including but not limited to antibodies, proteins, folates, ligands for specific cell receptors, receptors, peptides, viramines, wheat germ agglutinin, and combinations thereof. The ligands may include but not limited to ligands specific to folate, epithelial cell adhesion molecule (Ep-CAM), Hep-2, PAR, CD44, epidermal growth factor receptor (EGFR), as well as receptors of cancer cells, stem cells receptors, protein A receptors of *Staphylococcus aureus* (Spa), lipoprotein (Lpp), chitin receptors of yeasts, ligands specific to blood or lymphatic cell endothelial markers, polysaccharide and siderophore receptors of bacteria, as well as any antibody specific for proteins highly expressed in bacteria but absent in mammalian cells.

Non-limiting examples of contrast agents that may be functionalized include golden carbon nanotubes (GNTs), about 30-nm magnetic nanoparticles (MNPs) without and with silica layer (siMNPs), about 50-nm MNPs, PEG-coated gold nanorods (GNRs) with maximal absorption at about 690 nm and about 900 nm and GNRs at about 725 nm and about 900 nm without polyethylene glycol (PEG). In an aspect, the GNTs may have an average size of about 12×98 nm and may have a maximal absorption at about 850-1000 nm. In one aspect, the GNRs may have a maximal absorption at 690 nm. In another aspect, the GNRs may have a maximal absorption at 900 nm with and without PEG coating. In an aspect, the superparamagnetic iron oxide MNPs may consist of a magnetite ($Fe_3O_4$) with an about 50-nm core (3 stands for 3 crystals of 10-15 nm each) and may be coated with 10-nm Dextran layer (i.e., to make the total MNP size about 70 nm) and FITC may be covalently attached to activated sites on the Dextran. In an aspect, the about 30-nm MNP may have a thin layer of carboxylic acid (—COOH) at a concentration of about $2.4 \times 10^{12}$/mL and may be coated with about 10-nm silica-layer (Si-MNPs). Selected nanoparticles may be additionally conjugated with Fluorescein Isothiocyanate (FITC) in another aspect.

In an aspect, the GNTs and MNPs may be functionalized or conjugated with an Ig fraction of anti-protein A (anti-Spa). GNRs with maximal absorption at about 900 nm ($GNR^{900}$) may be bioconjugated with anti-Spa antibodies and GNRs with maximal absorption at about 690 nm ($GNR^{690}$) may be bioconjugated with anti-lipoprotein antibodies (anti-LPP). In another aspect, the FITC-conjugated Ig fraction of anti-Spa and Phycoelythrin (PE)-conjugated anti-Lpp antibodies may be verified by fluorescence imaging, taking into account the excitation of 490 nm and emission of 525 nm for FITC and the excitation of 488 and 565 nm and emission of 578 nm for PE.

The multilayer nanoparticles used as contrast agents for the target objects 140 may include two or more layers of materials with optical, thermal, and acoustic properties that enhance the PA signals 142 emitted by the target objects 140. Non-limiting examples of the effects of the multilayered nanoparticles on the PA pulses 142 emitted by the target objects 140 labeled with the multilayered nanoparticles include enhancing absorption of the laser pulse energy, increasing thermal relaxation time, increasing acoustic relaxation time, increasing the coefficient of thermal expansion, decreasing the coefficient of thermal diffusion, decreasing the local speed of sound near the target object 140, decreasing the threshold of bubble formation of the target object 140 and combinations thereof.

Exogenous target objects 140 such as unbound contrast agents, functionalized contrast agents, and exogenous unlabeled biological cells may be introduced into the circulatory or lymphatic vessels of the organism parenterally, orally, intradermally, subcutaneously, or by intravenous or intraperitoneal administration.

The target objects 140 may be concentrated near the desired area of detection using a variety of techniques. For target objects 140 possessing a larger diameter than the surrounding cells, the lumen of the vessel in which the target cells 140 are to be detected may be reduced in cross-sectional area using gentle mechanical pressure on the tissue surrounding the vessel, thereby retaining the larger diameter target cells 140, while allowing the surrounding cells with smaller diameter than the target objects 140 to flow away unimpeded from the desired area of detection. Alternatively, the target objects 140, regardless of object diameter, may be marked with magnetically active tags or markers, and the target objects 140 may be held in place by the magnetic forces exerted by a magnet with a magnetic field strength of at least seven Tesla, placed near the desired area of detection.

To further increase the contrast between PA signals 142 or originating from the target objects 140 and the background PA signals from surrounding cells and tissues, a variety of approaches may be used. The organism may be exposed to hyperoxic or hypoxic atmospheric conditions to induce different levels of oxygenation, which in turn alters the light absorption properties of the red blood cells. The osmolarity of the vessel flow may be altered by injecting hypertonic or hypotonic solutions into the desired vessel, thereby causing physical swelling or shrinking of surrounding cells, and further altering the light absorption characteristics of the surrounding cells. The hematocrit of the vessel flow may be altered by the injection of a diluting solution into the vessel flow, thereby reducing the density of surrounding cells in the vessel, and the resulting light absorption characteristics of the surrounding cells.

II. Tunable Wavelength Pulsed Laser

The PAFC device 100 includes a tunable wavelength pulsed laser 120 which generates light energy at laser pulse widths ranging between about 0.1 ps and about 1000 ns, at least one wavelength ranging between about 400 nm and about 2500 nm, laser pulse rates ranging between about 1 Hz and about 500,000 Hz, and laser pulse energy fluences ranging between about 0.1 mJ/cm$^2$ and about 10 J/cm$^2$. A variety of tunable wavelength pulsed lasers 120 may be used to produce the laser pulse 128 so long as the laser energy is delivered in such a way that minimal damage occurs to any target objects 140 or surrounding cells or tissues that are illuminated by the device 100. The laser pulses of at least one wavelength may be delivered by a single tunable wavelength pulsed laser 120 or by an array of tunable wavelengths pulsed lasers 120, with each laser source 120 delivering laser pulses 128 of different wavelengths.

Several characteristics of the tunable wavelength pulsed laser 120 strongly influence the performance of the device 100, including the wavelength of light emitted by the laser ($\lambda$), the diameter of the beam emitted by the laser, the duration of the light pulses emitted by the laser ($t_P$), the laser pulse repetition rate (f), and the laser fluence defined herein as the amount of energy emitted per square centimeter by the tunable wavelength pulsed laser 120.

A) Wavelength of Laser Pulse

The wavelengths of the laser pulses 132 may be selected to optimize the contrast of a single type of target object 140, or to optimize the contrast of two or more types of target objects 140. Typically, but not necessarily, to maximize the sensitivity and resolution of the PAFC device 100, the one or more wavelengths of laser pulses 132 should be optimized to enhance the contrast between the induced PA signals from the target objects 140 and the PA signals emitted by any surrounding cells. Thus, for target objects 140 that are unlabeled cells, the wavelength is selected in a range of the spectrum near the maximum absorbance of the unlabeled cells and as far as possible from the maximum absorbance of surrounding cells. If the target objects 140 are unbound contrast agents or cells that are labeled with contrast agents, the wavelength of the laser pulse 132 must fall within the range of wavelengths that are maximally absorbed by the contrast agents. As such, the present disclosure uses wavelengths of electromagnetic radiation emitted at wavelengths ranging between about 10 Å and about 1 cm. In an aspect, the PAFC device 100 uses wavelengths of light emitted in the near-infrared spectrum ranging between about 400 nm and about 2500 nm.

In other aspects, the PAFC device 100 may use wavelengths of light ranging from about 400 nm and 600 nm, from about 500 nm to about 700 nm, from about 600 nm to about 800 nm, from about 700 nm to about 900 nm, from about 800 nm to about 1000 nm, from about 900 nm to about 1100 nm, from about 1000 nm to about 1200 nm, from about 1100 nm to about 1300 nm, and from about 1200 nm to about 2500 nm. In an aspect, the PAFC device 100 may use diode lasers that generate laser pulses 132 with wavelengths ranging between about 640 nm and about 680 nm, between about 790 nm and about 830 nm, or between about 880 nm and about 930 nm. In an aspect, the PAFC device 100 may use laser pulses or modulated continuous radiation in the x-ray spectrum (1-10 Å), the terahertz spectra (20-1000 µm) or the microwave spectra (0.5 mm-3 cm).

B) Laser Beam Dimensions

The size and spacing of the target objects 140 typically, but not necessarily, determine the laser beam's 132 cross-sectional shape and dimensions of the laser beam 132. To distinguish closely spaced target objects 140 in circulation, the minimum laser beam 132 dimension should be no smaller than the diameter of the target objects 140. For the size range of potential target objects 140 such as unbound nanoparticles, bacteria, blood cells, or metastatic cells, the minimum laser beam 132 dimension ranges between about 1 μm and about 20 μm.

The laser beams 132 may have a circular cross-section, with diameters comparable to the blood or lymph vessel diameters, for detecting rare target objects 140 that may be target cells separated by distances of at least 100 □ m in circulation. For the detection of many closely-spaced target objects 140 in larger vessels, the laser beam 132 may be adjusted using known optical methods to an elliptical cross-sectional shape, with the long axis of the ellipse set to be the diameter of the larger vessel, and the short axis of the ellipse set to be the diameter of the cell in one aspect. In another aspect, the long axis of the ellipse may be set to any length larger than the short axis and the short axis of the ellipse may be set to be the diameter of the larger vessel.

In an aspect, laser radiation may be delivered to samples by using a customized condenser to create either circular beam (a lateral resolution of about 0.7 μm with a 20× objective, and an about 300 nm with 100× oil immersion objective) or linear beam shapes whose dimensions may be adjusted from about 10×50 μm to about 25×100 μm by positioning the axial condenser. As an alternative, a fiber with miniature cylindrical optics was used to deliver laser radiation directly to skin vessels (e.g., for PT therapy).

Thus, the laser beam 132 dimensions may range between about 1 μm and about 150 μm, in either a circular or an elliptical cross-sectional shape, depending on the relative rarity of the target objects 140, the dimensions of the target objects 140, and the diameter of the vessel in which the target objects 140 are detected. In an aspect, the diameter of the laser beam 132 may range from about 1 μm to about 10 μm, from about 5 μm to about 15 μm, from about 10 μm to about 30 μm, from about 20 μm to about 40 μm, from about 30 μm to about 50 μm, from about 40 μm to about 60 μm, from about 50 μm to about 100 μm, from about 75 μm to about 125 μm, and from about 100 μm to about 150 μm.

Although any device which supplies light energy with the above characteristics may be used, the tunable wavelength pulsed laser 120 may include but is not limited to a pulsed or modulated continuous laser 122 optically connected to an optical module 132. The laser source 122 may include but is not limited to gas lasers, chemical lasers, excimer lasers, solid state lasers, fiber-hosted lasers, semiconductor (diode) lasers, dye lasers, and free electron lasers. The optical module 132 converts the wavelength of light emitted by the pulsed laser 126 to at least one different wavelength used for in vivo PAFC of the target objects 140 as specified above, typically within the visible and NIR spectral ranges. The optical module 132 can be any device capable of converting the laser wavelength or pulse rate to the desired wavelength or pulse rate using linear or non-linear optical effects, including but not limited to optical parametric oscillators, optical crystals, etalons, monochromatic filters, distributed Bragg reflector structures, Lyot filters, Raman shifters, or combinations thereof.

C) Laser Pulse Duration

Typically, but not necessarily, to generate the maximum PA signal 142 with optimal conversion of light energy into acoustic energy, the laser pulse 132 duration, or pulse width, $t_P$ is predetermined to fall below a predetermined acoustic confinement criteria in order to minimize the mechanical stresses acting on the target object 140. This criterion may be expressed in equation form:

$$t_P \leq T_A = 2R/c_s \qquad \text{Eqn. (1)}$$

where $T_A$ is the transit time of the acoustic wave traveling through the target object 140, R is the radius of the target object 140, and $c_s$ is the speed of sound inside the target object 140. Assuming a target object 140 diameter ranging between about 0.5 μm and about 15 μm for typical cells such as bacteria, blood, and metastatic cells, and assuming that the speed of sound inside the target objects 140 is approximately the same as the speed of sound in water ($1.5 \times 10^5$ cm/sec), then the range of the pulse durations required for detecting most potential target objects 140 ranges between about 0.7 ns and about 20 ns. Smaller bacterial cells may use pulse durations near the lower end of the range specified above, and larger metastatic cells may use pulse durations near the upper end of this range. Extremely small target objects 140 such as individual nanoparticles may require pulse durations of about $10^{-4}$ ns.

The device 100 typically uses a pulse duration ranging between about 1 ns and about 20 ns, depending on the size of target objects 140. In other aspects, the pulse duration may range from about 1 ns to about 5 ns, from about 3 ns to about 7 ns, from about 5 ns to about 10 ns, from about 7 ns to about 15 ns, from about 10 ns to about 15 ns, from about 13 ns to about 17 ns, and from about 15 ns to about 20 ns.

D) Laser Pulse Repetition Rate

To accurately identify and discriminate between numerous circulating target objects 140 in relatively fast flow conditions, the pulsed laser 122 must typically, but not necessarily, have a pulse repetition rate that is sufficiently rapid to ensure that only one target object 140 is illuminated per pulse. In equation form, the laser pulse repetition rate (f) must fulfill the following predetermined criterion:

$$f \geq (V_F)/D \qquad \text{Eqn. (2)}$$

where ($V_F$) is the flow velocity, and D is the diameter of the target object 140. In small mammal blood microvessels, flow velocities typically range from 1 mm/sec (capillary) to 10 mm/sec (arterioles). For a cell diameter of 20 μm, the pulse repetition rate may range between about 50 Hz and about 500 Hz. To detect smaller target objects 140, or target objects 140 in faster flowing vessels, the pulse repetition rate should be near higher end of this range. A high laser pulse repetition rate may also enhance the sensitivity of the device 100 during multi-pulse laser exposures because signal-to-noise ratio, which limits the sensitivity of the device 100, is proportional to the square root of the number of laser pulses.

In an aspect, the PAFC device 100 of the present disclosure uses a pulse repetition rate ranging between about 1 Hz and about 500,000 Hz. In other aspects, the pulse repetition rate may range from about 1 Hz to about 10 Hz, from about 5 Hz to about 25 Hz, from about 20 Hz to about 60 Hz, from about 50 Hz to about 100 Hz, from about 75 Hz to about 125 Hz, from about 100 Hz to about 500 Hz, from about 400 Hz to about 1 kHz, from about 800 Hz to about 10 kHz, from about 5 kHz to about 50 kHz, from about 40 kHz to about 100 kHz, from about 80 kHz to about 300 kHz, and from about 200 kHz to about 500 kHz.

In addition, when the one or more target objects 140 are illuminated by laser pulses of two or more different wavelengths, the time delay between the laser pulse 132 of one wavelength and the subsequent laser pulse 132 of a different wavelength should be sufficiently short so as to ensure that the two or more laser pulses illuminate the same target object 140. Further, the laser pulses 128 should have a time delay that further ensures that the second laser pulse 132 does not reach the target object 140 prior to detection of the PA signal 142 induced by the first laser pulse 132. For the range of distances at which the PAFC device 100 detects target objects 140, the time delay between laser pulses 132 ranges between about 0.1 µs and about 100 µs. In an aspect, a single laser may emit more than one wavelength within the time delay between laser pulses.

E) Laser Fluence

The laser fluence of the PAFC device 100, defined herein as the energy level of the laser pulse 132. In an aspect, the laser fluence may not exceed the ANSI safety standard, which depends on the laser's wavelength, and may range between about 30 mJ/cm$^2$ and about 100 mJ/cm$^2$ in the NIR spectral region emitted by the laser 120. In addition, the laser fluence should not exceed the thresholds at which significant cell photodamage may occur for detection of the target objects 140.

In an aspect, the PAFC device 100 may develops a laser fluence ranging between about 10 µJ/cm$^2$ and about 1000 J/cm$^2$, depending on factors such as the size and type of target objects 140, the depth of the vessel in which the target objects 140 are to be detected, and the density of the cells surrounding the vessel. In other aspects, the laser fluence may range from about 10 µJ/cm$^2$ to about 50 µJ/cm$^2$, from about 25 µJ/cm$^2$ to about 100 µJ/cm$^2$, from about 75 µJ/cm$^2$ to about 1 mJ/cm$^2$, from about 750 µJ/cm$^2$ to about 5 mJ/cm$^2$, from about 3 mJ/cm$^2$ to about 10 mJ/cm$^2$, from about 8 mJ/cm$^2$ to about 20 mJ/cm$^2$, from about 18 mJ/cm$^2$ to about 30 mJ/cm$^2$, from about 25 mJ/cm$^2$ to about 50 mJ/cm$^2$, from about 40 mJ/cm$^2$ to about 100 mJ/cm$^2$, from about 75 mJ/cm$^2$ to about 500 mJ/cm$^2$, from about 400 mJ/cm$^2$ to about 1000 mJ/cm$^2$, from about 750 mJ/cm$^2$ to about 10 J/cm$^2$, from about 5 J/cm$^2$ to about 50 J/cm$^2$, from about 25 J/cm$^2$ to about 100 J/cm$^2$ from about 75 J/cm$^2$ to about 500 J/cm$^2$ and from about 300 J/cm$^2$ to about 1000 J/cm$^2$.

When lower laser fluences are used, the resulting PA signals 142 are proportionally weaker in amplitude, and a more sensitive acoustic detection system 100 with signal acquisition properties that are optimized for the location and frequency of the PA signals 142 may be used to provide reliable detection of PA signals 142 from the target objects 140. Higher laser fluences may be used during the destruction of target objects 140.

For PAFC measurements on vessels in deeper tissues, the laser pulses 132 may be delivered non-invasively at higher laser fluence from outside the organism. To avoid potential damage to any tissues located between the pulsed laser 120 and the target objects 140 resulting from higher energy laser pulses 132 or extended periods of PAFC measurement, the tissues may be cooled using methods broadly used in dermatological laser applications including but not limited to spray cooling, contact cooling, skin cooling with forced cooled air or liquid flow, an optically transparent cooling device attached to skin and cooled using circulating cooled water or electrical effects, and combinations thereof.

In an aspect, laser pulses 132 may be delivered using a fiber optic cable placed in close vicinity of the target objects 140 using a minimally invasive needle delivery device. The laser pulses 132 may be delivered directly to the desired vessel using an optic fiber cable mounted in a catheter. The laser pulses 132 may be delivered by fiber-chip-based catheters inserted directly into the desired vessel. The target objects 140 may be detected by shunting circulating target objects 140 through artificial circulatory bypass tubes similar to those used in hemodialysis, that are transparent to laser light in the visible or NIR spectra, through a hemodialysis system, or through similar bioengineering devices known in the art.

III. Optics

Optics 130 are operatively connected to the output 128 of the tunable wavelength pulsed laser 120, and functions to deliver the laser pulses 132 to the target objects 140 or other desired area of illumination. The optics 130 are selected to deliver the laser pulses 132 to the target objects 140 with a beam dimension ranging between about 1 µm and about 40 µm, with a circular or elliptical cross-sectional geometry, as discussed above. The optics 130 may include but are not limited to conventional lenses, mirrors, optics fibers, and combinations thereof, so long as the shape and diameter of the beam may be controlled.

IV. Ultrasound Transducers

The ultrasound transducers 150 are pressure sensors that are placed in acoustical contact with the target objects 140 at a distance of up to 15 cm from the target objects 140. The ultrasound transducers 150 convert the laser-induced PA signals 142 received from the target objects 140 into voltage fluctuations that are subsequently amplified, digitized, stored, and/or analyzed. The ultrasonic transducers 150 are selected for their optimal sensitivity to the PA signals 142 emitted by the target objects 140. The ultrasonic transducers 150 typically have a sample rate ranging between about 10 kHz and about 100 MHz. Non-limiting examples of ultrasonic transducers so include, unfocused ultrasound transducers; focused ultrasound transducers with conventional and cylindrical focused lengths between about 2 mm and about 500 mm; and customized resonance ultrasound transducers. In an aspect, the ultrasonic transducer 150 and pulsed laser 122 may have a confocal configuration, in which the transducer 150 may have a ring geometry with the pulsed laser 122 and associated optics 130 passing through the center of the ring of the transducer 150. In an aspect, the PAFC device 100 may include one or more ultrasonic transducers 150.

The efficiency of acoustic matching of the ultrasound transducer 150 and the tissue of the organism may be enhanced by the application of an acoustically transparent liquid, such as glycerol, between the skin and the receiving surface of the ultrasound transducer 150. Any liquid may be placed between the skin and the receiving surface of the ultrasound transducer 150, so long as the liquid efficiently transmits ultrasound pressure waves. In addition, the acoustically transparent liquid should also transmit laser pulses in the visible and NIR spectra with minimal scattering of the laser pulse energy, if the liquid is located in the path of the laser pulse 132.

V. Amplifier

An optional amplifier 152 may be electrically connected to the voltage output 160 of the ultrasonic transducer 150, should the PA signal 142 received from the target objects 140 prove to be too weak to analyze accurately. The amplifier 152 is selected for sensitivity and responsiveness to the PA signals 142 measured by the one or more ultrasonic transducers 150. The amplifier 152 is selected to possess a low frequency boundary between about 10 kHz and about 200 kHz, a high frequency boundary between about 1 MHz and about 100 MHz, and a resonance bandwidth between about 0.3 MHz and about 5 MHz. Any amplifier 152 can be used so long as it possesses the frequency response and resonance bandwidth described above.

VI. Data Recording System

A data recording system 154 may be connected to the voltage output 160 of the ultrasonic transducer 150, or alternatively, the amplified output 162 of the ultrasonic transducer 150. Any digital or analog device capable of acquiring and storing incoming voltage data at frequencies as high as 50 MHz may be used. Non-limiting examples of the data recording system 154 include a boxcar averager device, a video camera recording the display of an oscilloscope electrically connected to receive the output of the ultrasonic transducer 150 or the amplifier 152, and combinations thereof.

In an aspect, the data recording system 154 may include a high-speed (about 200 MHz) analog-to-digital converter board. A boxcar averager device averages the output of several successive PA signals 142 to optimize the accuracy of the PAFC device 100. The oscilloscope display may be run at low speed to acquire the counts of many target objects 140 passing the PAFC device 100 in close succession, or the oscilloscope display may be run at high speed to discern detailed characteristics of the PA signal 142 such as wave magnitude or wave shape used to discriminate the target object 140 from surrounding cells. The data recording system 154 may include a still camera may be used to record the display an oscilloscope connected to the output of the ultrasonic transducer 150 or the amplifier 152.

VII. Data Analysis Software

The data analysis software 158 may access the stored data 164 from the data storage device 154, the voltage output 160 from the ultrasonic transducer 150, the voltage output 162 from the amplifier 152, or combinations thereof. The data analysis software 158 may also function as an amplifier 152, a data storage device 154, and combinations thereof. Any data analysis software 158 capable of processing data that fluctuates at frequencies ranging between about 20 Hz and 200 MHz may be used, including but not limited to user-written software, or commercially available analysis software. Non-limiting examples of commercially available analysis software includes Matlab (The MathWorks, Inc., USA), Mathematica (Wolfram Research, Inc., USA), Labview (National Instrument, USA), Avisoft (Avisoft Bioacoustics, Germany), and TomoView (Olympus NDT Inc., USA).

In an aspect, each PA signal trace may be analyzed for the presence of peaks with height exceeding a defined threshold height. The stable baseline due to the background absorption by blood may be subtracted electronically and accurately, to help observe very small peaks.

VIII. Magnetic Module

The photoacoustic flow cytometry (PAFC) device 100 may include a magnetic module for interacting with magnetic contrast agents. In an aspect, the local permanent magnetic field in selected vessels may be provided by a cylindrical Neodymium-Iron-Boron (NdFeB) magnet with a Ni—Cu—Ni coating. The magnet may be about 3.2 mm in diameter and about 9.5 mm long with a surface field strength of about 0.39 Tesla.

IX. Combined Photoacoustic/Photothermal/Fluorescent Flow Cytometry Systems

The photoacoustic flow cytometry (PAFC) device 100 may include additional elements including, but not limited to photodetectors, a CCD camera, additional lasers and optics, and additional analysis software associated with other in vivo flow cytometry methods that detect the target objects using the conventional and Raman scattering of the laser pulses by the target objects, photothermal effects induced by laser pulses on the target objects, and the fluorescence of the target objects induced by absorbed laser pulses. In an aspect, the device 100 may be configured to simultaneously detect cells using photoacoustic methods, photothermal methods, light scattered by target objects, induced fluorescence of target objects, and any combination thereof.

In an aspect, the device 100 may be capable of high-resolution and high-speed transmission and fluorescent microscopy. PA and PT microscopes may be equipped with high resolution fluorescent and transmission modules. A cooled, color CCD camera may be used for the navigation of laser beams and for the verification of PA and PT data with fluorescent images using specific fluorescent tags. High-resolution (about 300 nm) transmission digital module (TDM) fitted with a high-speed (up to about 40,000 fps) CMOS and high sensitive CCD cameras may be used for imaging blood vessels, ear and other organs with bacteria.

X. Method of In Vivo Flow Cytometry

The present disclosure further provides a method of in vivo flow cytometry using laser-excited photoacoustic pulses 142 emitted by at least one type of target object 140 circulating in the vessels of an organism. The method includes pulsing the target objects 140 moving through the vessels with at least one pulse of laser energy 132 at one or more wavelengths. As described above, the target objects 140 absorb the at least one pulse of laser energy 132 and emit at least one ultrasound photoacoustic pulse 142. The photoacoustic pulses 142 are detected by at least one ultrasound transducer 150, as described above. The photoacoustic pulses 142 are analyzed to determine at least one characteristic of the detected target objects 140. The characteristics of the detected target objects 140 may include, but are not limited to the type of target objects 140, the quantity of target objects 140, the concentration of target objects 140, the flow speed of the target objects 140, the total blood volume, and combinations thereof.

The flow speed of the target objects 140 may be based on analysis of the width of the PA signal 142 emitted by a target object 140, the time delay between two PA signals 142 measured at two locations separated by a known distance, or the frequency shift of a PA signal 142. The total circulating blood or lymph volume may be estimated using the degree of dilution of one or more absorbing dyes, or blood cells extracted from the organism, labeled using the marking compounds discussed above, and reintroduced into the vessels of the organism.

A) PA Signal Patterns

Signature PA signal patterns associated with each type of target object 140, include but are not limited to signal shape, frequency spectrum, amplitude, phase, and time delay between the one or more laser pulses 132 and the received PA signal 142. The PA signal patterns may be discriminated between PA signals 142 received from target objects 140 and background PA signals received from surrounding cells, blood and lymphatic vessel walls, and tissues. Further, the blood or lymph flow velocity may be determined using PA signal patterns including but not limited to the PA signal duration, the PA frequency shift, or the time delay between two PA signals 142 produced by a single target object 140 pulsed by two distinct laser pulses 132 applied at a known separation distance.

Different target object 140 types possess unique combinations of pigments and sub-cellular structures that absorb laser pulses 132 and emit PA signals 142 differently. Each type of target object 140 may be discriminated by its distinctive PA signature, as well as the particular wavelengths of laser pulses 132 used to elicit the PA signals 142 from target objects 140 without need for labeling. The contrast of the target objects 140 may be enhanced using contrast agents bound to the target objects 140 as described above.

The contrast of the PA signal patterns of the target objects 140 relative to surrounding cells and tissues are typically based on PA signal 142 amplitudes from the target objects 140 that are significantly higher than amplitudes of the PA signals 142 amplitudes from the surrounding cells and tissues. For example, aggregations of red blood cells in circulation may be detected using time-resolved monitoring of dynamic increases of PA signal amplitudes due to the higher local absorption of laser pulses 132 that result in higher amplitude PA signals 142 from the red blood cell aggregates relative to surrounding cells and tissues.

The PA signal amplitude emitted by target objects 140 may also be significantly lower than the PA signal 142 amplitudes from the surrounding cells and tissues. For example, circulating blood clots may be detected through the time-resolved monitoring of dynamic decreases of the PA signal amplitude, due to the attenuated PA signal amplitude emitted by blood clots relative to the PA signal amplitude emitted by red blood cells. The decreased PA signal amplitude emitted by blood clots is due to the lower light absorption of platelets (the dominant component of blood clots) relative to the light absorption of red blood cells (the dominant cell type overall in typical blood flows) in the visible and near-infrared spectral range. Whether the PA signal 142 of the target objects 140 is significantly higher or significantly lower than the PA signal 142 from surrounding cells and tissues, sufficient contrast must exist to accurately detect the PA signals of the target cells 140.

B) Detection of Target Objects in Lymph Vessels

For the detection of target objects 140 in the lymph vessels, target objects 140 are illuminated while passing between the leaves of a valve in a lymphatic vessel. The restricted flow through the valve of the lymphatic vessel facilitates the detection and identification of individual target objects 140. The phasic contractions of lymph vessels naturally concentrate the flow of target objects 140 near the center of the lymph vessel, and the lymph valves act as natural nozzles to provide the positioning of target objects 140 in single file with minimum radial fluctuation. To exclude detecting the same target objects 140 during their retrograde motion, as is typical in lymphatic vessels, the timing of the laser pulses 32 may be adjusted to synchronize with the phasic rhythms of the lymphatic flow. In addition, detection of forward moving target objects 140 may be achieved by synchronizing the laser pulses 132 with the motion of the lymphatic vessel wall or lymphatic valves that typically occurs during forward flow of lymph. The motion of the lymph vessel wall or lymphatic valves may be sensed using an additional pilot laser that produces signals that may be used to trigger the PAFC laser pulses 132.

The sensitivity of the detection of target objects 140 in lymph vessels may be enhanced by creating a higher rate of lymph flow through the lymphatic valve by inducing the contraction of the upstream lymphangion, defined herein as the lymph vessel between two lymphatic valves. For example, the lymphangion may be induced to contract by exposure to a pulse of laser light 132 at a wavelength ranging between about 400 nm and about 950 nm, applied prior to the laser pulses 132 used to induce PA signals 142 from the target objects 140.

XI. Method of In Vivo Detection of Circulating Melanoma Cells

The present disclosure further provides a method for non-invasive detection of circulating unlabeled metastatic melanoma cells. The method includes pulsing at least one circulating metastatic melanoma cell with at least one pulse of NIR laser energy 132 at least one wavelength ranging between about 650 nm and about 950 nm and a laser fluence ranging between about 20 mJ/cm$^2$ and about 100 mJ/cm$^2$. The circulating unlabeled metastatic melanoma cells absorb the at least one laser pulse 132 and emit at least one ultrasound photoacoustic pulse 142, that is detected by at least one ultrasound transducer 150. The detected photoacoustic pulse 142 is analyzed to detect the presence of any metastatic melanoma cells in circulation.

Unlabeled metastatic melanoma cells in particular may be detected in the circulatory or lymphatic system of the organism using the method of the present disclosure. Without being bound to any particular theory, the large stores of melanin characteristic of melanoma cells readily absorb light at a wavelength of approximately 850 nm and emit strong photoacoustic ultrasound signals 142. Using the device 100 of the present disclosure with a tunable wavelength pulsed laser 120 with a pulse wavelength of about 850 nm, a laser fluence of about 35 mJ/cm$^2$, and a laser pulse duration of about 8 ns, circulating unlabeled metastatic melanoma cells may be detected with a resolution of at least 1 melanoma cell per $10^{10}$ cells.

XII. Method for Selectively Destroying Circulating Cells in Vivo

In an aspect, photoacoustic (PA)/photothermal (PT) theranostic platforms may be used as part of a method for detecting and destroying circulating target objects 140. The circulating target objects 140 may include, but are not limited to circulating bacterial cells (CBCs) and circulating tumor cells (CTCs). The circulating target objects 140 may be targeted in vivo by functionalized contrast agents to enhance the PA signal for detection and subsequently more specific destruction of the target objects 140. Non-limiting examples of the contrast agents include gold nanoparticles, gold nanorods, spectrally tunable golden carbon nanotubes, silica-coated magnetic nanoparticles, and any combination thereof. In an aspect, the contrast agents may be functionalized with protein A (Spa) and/or lipoproteins to specifically target bacteria cells.

There are no efficient antibiotics for infections, currently available to the clinician, for which resistance has not been reported. Thus, it is imperative to develop therapeutic approaches that can alleviate this limitation. The in vivo PA/PT nano-theranostic platform offers many advantages: (1) physical destruction of bacteria, thus retaining its therapeutic efficacy irrespective of the antibiotic resistance status of the offending bacteria; (2) integration of molecular detection and targeted elimination of fast-moving, 1-2 μm bacteria in heterogeneous blood flow with real-time monitoring of therapeutic efficacy; (3) ultra-high sensitivity (0.5 CFU/mL) for both diagnosis and treatment at the level of a single bacterial cell in the exposed volume; (4) the use of nanoparticles as high absorbing, low toxic molecular contrast agents allowing for significant amplification of their signal properties, thus requiring as few as 100-1000 nanoparticles per cell; (5) high spectral specificity based on distinct ultrasharp spectral resonances of gold nanoparticles and asymmetric nonlinear spectra of magnetic nanoparticles; (6) intravascular magnetic capturing of CBCs for further amplification and laser ablation; and (7) multiplexing capability using antibody cocktails to avoid the development of resistance and effectively target genotypically and phenotypically diverse strains both within and across different bacterial pathogens, thus facilitating the treatment of polymicrobial infections.

Referring back to FIG. 2 the theranostic method may selectively destroy circulating target objects 140 using laser pulses 132 with a higher laser fluence than is typically used by the PAFC device 110. In an aspect, the circulating target objects 140 may include, but is not limited to metastatic cancer cells and bacteria cells. The method may include detecting the target objects 140 circulating in the vessels. The detection of a target object 140 may trigger a pulse of laser energy 132 that is delivered to the detected target object 140 at a wavelength and fluence sufficient to cause the destruction of the detected target objects 140. The method may include monitoring the frequency of detection of target objects 140 circulating through the vessels, and terminating the method when the frequency of detection of the target objects 140 falls below a threshold level. The method of destroying target objects 140 may be terminated when the frequency of detection of target objects 140 falls below between about $10^{-3}$ target objects/min and about $10^2$ target objects/min.

The target objects 140 may be detected using a method of in vivo flow cytometry using laser-excited photoacoustic waves 142 emitted by the target objects 140.

Because the absorption of target objects 140 are much higher than surrounding cells and tissue, the laser fluence may be increased beyond the level normally used for PAFC to levels that selectively damage the target objects 140 without harming the surrounding cells and tissues. Target objects 140 that are selectively destroyed using the method of the present disclosure include but are not limited to tumor cells, bacteria, viruses, clots, thromboses, plaques, and combinations thereof. This approach may be used for the selective destruction of target objects 140 circulating in blood vessels or lymph vessels. The PAFC methods of the present disclosure may be used to detect the target objects 140, trigger the high energy laser pulse 132 used to destroy the target objects 140, and detect the subsequent decrease in the target objects 140, thereby guiding the cell destruction at the single cell level.

Better understanding of the characteristics of life-threatening pathogens is very important for the successful development of antimicrobial therapeutic agents. Surprisingly, many of key questions about bacteria dissemination to distant organs are still unanswered, including migration in tissue, invasion dynamics, interaction with blood and endothelial cells, and extravasations. The method of selectively destroying circulating cells and in combination with animal models of bacteremia may establish a research tool, which could provide new insights on CBC dissemination, leading to the development of metastatic foci of infection, including endocarditis, osteomyelitis, and infections associated with catheters and implants. Similarly as with the study of CTCs, this, tool could facilitate understanding of the CBC properties, including possible re-entering back into the circulation from the distant sites (i.e., lung at pneumonia or brain at meningitis) with further haematogenous spreading to other sites (reseeding) or even to the site of origin (self-seeding). Without being limited to any particular theory, aggressive populations of CBCs may be analogous to cancer stem cells, which may significantly contribute to bacterial colonization and drug resistance.

Figure 44:
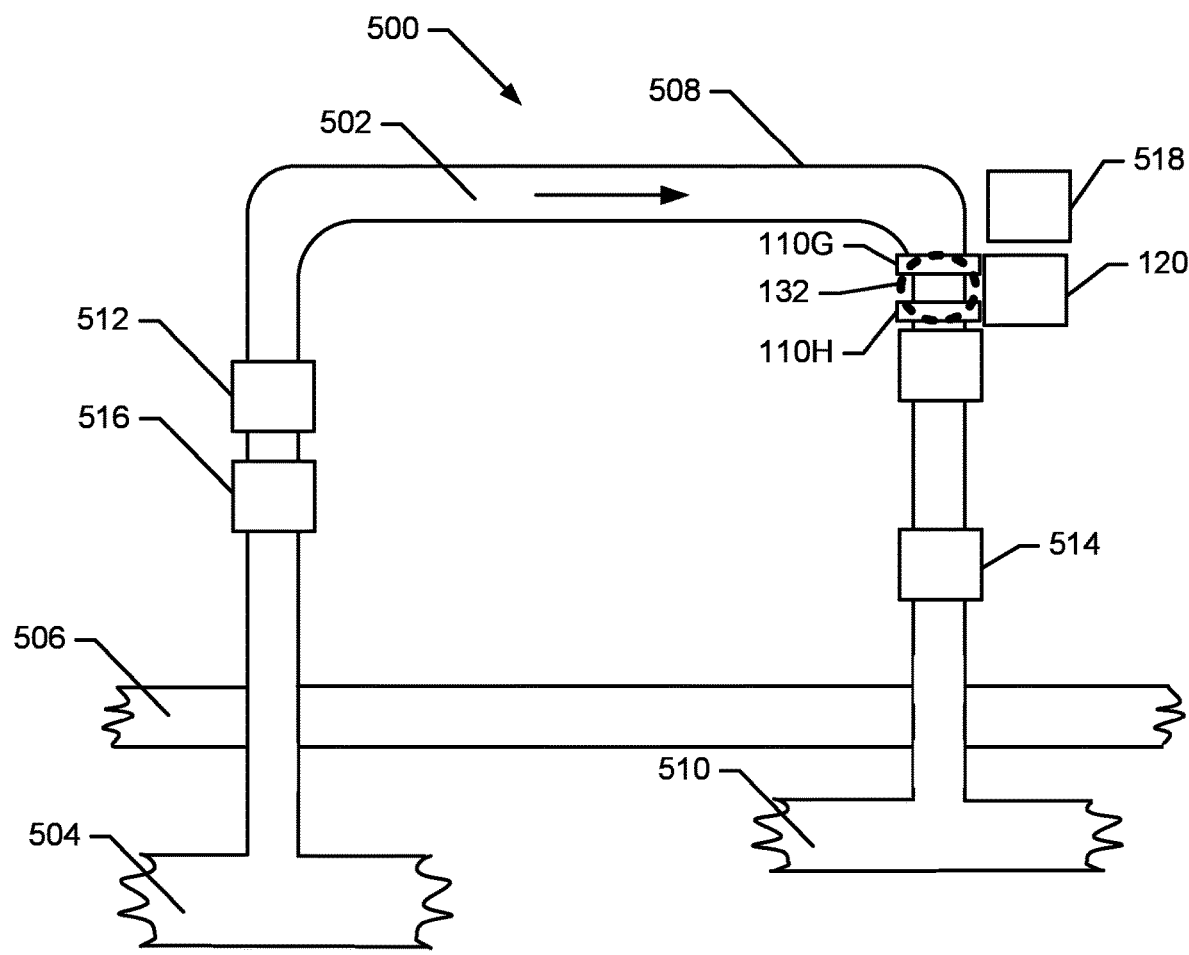
FIG. 44 is a diagram of an extracorporeal shunt inserted into an organism to direct the flow of a biofluid outside of the organism and to return the biofluid back into the organism.

In an aspect, laser-based detection and treatment of CBCs may be accomplished in a 0.5-1.5 mm hand vein at 1-2 mm depths, which is within well-documented capacity of PA technology to access much deeper (3 cm) and larger (1 cm) human blood vessels. In an aspect, bypass schematics such as the extracorporeal device illustrated in FIG. 44, may be utilized for purging of infected blood during sepsis crisis with simultaneous magnetic removal of CBCs and MNPs from circulation. This method would also retain the molecular specificity for the involved bacteria, even with slowly growing biofilm-associated *S. aureus* bone infection, in which, like the gene encoding protein A, the gene encoding the lipoprotein is highly conserved and highly expressed among different strains of *S. aureus* including antibiotic-resistant strains. In an aspect, the label-free approach at NIR wavelengths near 740 nm may be useful for rapid (minute-scale), non-toxic and noninvasive diagnosis of skin infections, and potentially for disinfection of instruments or food without antimicrobial agents.

EXAMPLES

The following examples illustrate various aspects of the disclosure.

Example 1. In Vitro Photothermal (PT) Imaging was Used to Determine the Effect of Laser Energy Levels on Laser-Induced Cell Damage to Blood Cells and Subsequent Cell Viability To determine whether the laser pulses using in in vivo flow cytometry caused any significant damage to cells or tissues of the organism, the following experiment was conducted. The laser-induced damage threshold of single cells was evaluated as a function of the pumped-laser energy levels at a range of wavelengths using established methods (Zharov and Lapotko 2005, Lapotko and Zharov 2005). In vitro measurements of specific changes in photothermal (PT) images and PT responses from individual cells were used to determine cell damage. During the PT imaging, individual cells were illuminated with a pulse of laser light at a specified energy level and wavelength. After absorbing the energy of the laser pulse, the short-term temperature of the cell increased by as much as 5° C. The laser-induced temperature-dependent refractive heterogeneity in the vicinity of cells caused defocusing of a collinear He—Ne laser probe beam (model 117A; Spectra-Physics, Inc.; 633 nm, 1.4 mW) that illuminated the cell immediately after the initial laser pulse. This defocusing caused a subsequent reduction in the beam's intensity at its center, which was detected with a photodiode (C5658; Hamamatsu Corp.) through a 0.5-mm-diameter pinhole.

PT measurements were performed in vitro using mouse blood cells in suspension on conventional microscope slides. To simulate blood flow conditions, a flow module fitted with a syringe pump-driven system (KD Scientific, Inc.) was used with glass microtubes of different diameters in the range of 30 μm to 4 mm that provided flow velocities of 1-10 cm/sec, which were representative of the diameters and flow rates of animal microvessels.

Individual cells flowing through the glass microtubes were exposed to an 8 ns burst of laser light in a 20-□m circular or elongated beam at a variety of wavelengths ranging between 420 nm and 2300 nm. At each wavelength of the initial laser pulse, the laser fluence, defined as the energy contained in the laser beam, was varied between 0.1 mJ/cm$^2$ and 1000 J/cm$^2$. Damage to the cells was determined by assessing the changes in the PT imaging response of cells to laser pulses of increasing fluence. In addition, cell viability after exposure to laser energy was assessed using a conventional trypan blue exclusion assay. Cellular damage was quantified as ED50, the level of laser fluence at which 50% of the measured cells sustained photodamage in vitro. The ED50 values measured for rat red blood cells (RBC), white blood cells (WBC) and K562 blast cells using laser pulses in the visible light spectrum are summarized in Table 1. The ED50 values measured for rat red blood cells (RBC) and white blood cells (WBC) using laser pulses in the near-infrared (NIR) light spectrum are summarized in Table 2.

TABLE 1

Photodamage thresholds for single rat blood
cells in the visible light spectrum.

| Wavelength of laser pulse (nm) | Photodamage threshold ED50 (J/cm$^2$) | | |
|---|---|---|---|
| | Rat RBC | Rat WBC | Rat K562 blast cell |
| 417 | 1.5 | 12 | 36 |
| 555 | 5 | 42 | 90 |

TABLE 2

Photodamage thresholds for single
rat blood cells in near-IR spectral

| Wavelength of laser pulse (nm) | Photodamage threshold ED50 (J/cm$^2$) | |
|---|---|---|
| | Rat RBCs | Rat WBCs |
| 740 | 6.9 | 21.7 |
| 760 | 6.8 | |
| 780 | 17.7 | 152 |
| 800 | 17.5 | 219 |
| 820 | 28.0 | 251 |
| 840 | 43.5 | |
| 860 | 43.8 | 730 |
| 880 | 76.5 | |
| 900 | 69.4 | |
| 920 | 77.7 | 357 |
| 960 | 33.5 | 48.8 |

In the visible spectral range, the relatively strong light-absorbing RBCs sustained cell damage at much lower intensities of laser energy, resulting in ED50 values that were about an order of magnitude lower than the ED50 values measured for WBC or K562 blasts. In the NIR spectral range, where most cells, including RBC, have minimal absorption, cells did not sustain damage until much higher laser energy levels compared to the energy levels at which cellular damage occurred to cells exposed to laser energy in the visible spectrum. The damage thresholds (ED50) for RBCs and WBCs in the spectral range of 860-920 nm were more than one order magnitude higher compared to those in the visible spectrum as shown in Tables 1 and 2.

The results of this experiment established the levels of laser energy at which laser-induced cellular damage may occur. In the NIR spectrum, in which cells exhibited the strongest photoacoustic effects, the damage thresholds are several orders of magnitude above the maximum safety level of approximately 20-100 mJ/cm$^2$ set by ANSI safety standards. Thus, photoacoustic flow cytometry may be performed in vivo with little risk of cell or tissue damage.

Example 2. Prototype In Vivo Photoacoustic Flow Cytometry System Used to Detect Contrast Dye Circulating in Mice The following experiment was conducted to demonstrate the feasibility of in vivo photoacoustic flow cytometry (PAFC) for real-time, quantitative monitoring in the blood circulation of a conventional contrast agent, Lymphazurin. In this experiment, a prototype PAFC system was used to detect Lymphazurin circulating in the blood vessels of a mouse ear.

The prototype PAFC system was built on the platform of an Olympus BX51 microscope (Olympus America, Inc.) and a tunable optical parametric oscillator (OPO) pumped by an Nd:YAG laser (Lotis Ltd., Minsk, Belarus). The general layout of the PAFC system is shown in FIG. 2. Laser pulses had an 8 ns pulse width, a regular repetition rate of 10 Hz with the ability to provide short-term pulses at 50 Hz, and a wavelength in the range of 420-2,300 nm. Laser energy was directed to the blood vessels using a conventional lens, or an optical fiber. PA waves emitted by the cells were detected by ultrasound transducers (unfocused Panametrics model XMS-310, 10 MHz; focused cylindrical Panametrics model V312-SM, 10 MHz, focused lengths of 6 mm, 12 mm, and 55 mm; and customized resonance transducers), and the ultrasound transducer outputs were conditioned by an amplifier (Panametrics model 5662, bandwidth 50 kHz-5 MHz; Panametrics model 5678, bandwidth 50 kHz-40 MHz; customized amplifiers with adjustable high and low frequency boundaries in the range to 50-200 KHz and 1-20 MHz, respectively; resonance bandwidth of 0.3-1.0 MHz). The amplifier output signals were recorded with a Boxcar data acquisition system (Stanford Research Systems, Inc.) and a Tektronix TDS 3032B oscilloscope, and were analyzed using standard and customized software. The Boxcar data acquisition technique provided averaging of the PA waves from cells in the blood vessels, and discriminated the PA waves from background signals from surrounding tissue on the basis of the difference in time delays between the two signals. The signals from the oscilloscope screen were recorded with a digital camera (Sony, Inc.) and video camera (JVC, Inc.).

A high-speed computer (Dell Precision 690 workstation with a quadcore processor, 4 GB of RAM and Windows Vista 64 bit operating system) and digitizer (National Instruments PCI-5124 high speed digitizer) were used to acquire the PA signal data from the PAFC device. National Instruments software (Labview Version 8.5 and NI Scope Version 3.4) was used to control the digitizer and create a data logging user interface. The hardware and supporting program were capable of collecting data at a rate of 200 megasamples per second, corresponding to a time resolution of 5 ns.

A laser beam with a circular cross section and a diameter of approximately 50 μm, a wavelength of 650 nm, and a fluence of 35 mJ/cm$^2$ was used to illuminate the flow in the blood vessels. The 650 nm wavelength used was near the wavelength of maximum absorption of Lymphazurin, the contrast dye used in this experiment, and well separated from the wavelengths of maximum absorption of other blood components. Navigation of the laser beams was controlled with transmission digital microscopy (TDM) at a resolution of approximately 300 nm using a Cascade 650 CCD camera (Photometrics).

All in vivo experiments described below were performed using a nude mouse ear model. PAFC detection was performed using relatively transparent, 270 μm thick mouse ears with well-distinguished blood microvessels. The ear blood vessels examined were located at a depth of 30-100 μm, had diameters in the range of 30-50 μm, and blood velocities of 1-5 mm/sec. After undergoing anesthesia using ketamine/xylazine at a dosage of 50/10 mg/kg, each mouse was placed on a customized heated microscope stage, together with a topical application of warm water, which provided acoustic matching between the transducer and mouse ear.

The contrast dye used for the experiments described below was Lymphazurin, a contrast agent commonly used for the delineation of lymphatic vessels. A 1% solution of Lymphazurin (Isosulfan Blue) was purchased from Ben Venue Labs Inc., USA.

After anaesthetizing each mouse and placing the mouse on the microscope stage as described above, 200 µL of a 1% aqueous solution of Lymphazurin was injected into the tail vein of the mouse.

PAFC measurements of the circulating dye were performed at a laser pulse wavelength of 650 nm. FIG. 3 shows oscilloscope traces of PAFC signals from the blood vessels and surrounding tissues in the rat ear before and after injection with Lymphazurin. Prior to injection, the maximum 240 mV PA signals from blood vessels, shown in FIG. 3A, were approximately 1.5 times higher than the 160 mV PA background signals from surrounding tissue, shown in FIG. 3B. Maximum PA signals from the blood vessel after dye administration, shown in FIG. 3C, increased approximately three-fold over pre-injection levels. The PA signals from tissue around vessels after dye injections, shown in FIG. 3D, gradually increased approximately 2.5-fold over pre-injection levels during the first 15-20 minutes, and then remained relatively constant for the next 1-1.5 hours, probably due to the passage of the Lymphazurin out of the blood vessels and into nearby lymphatic vessels.

Figure 4:
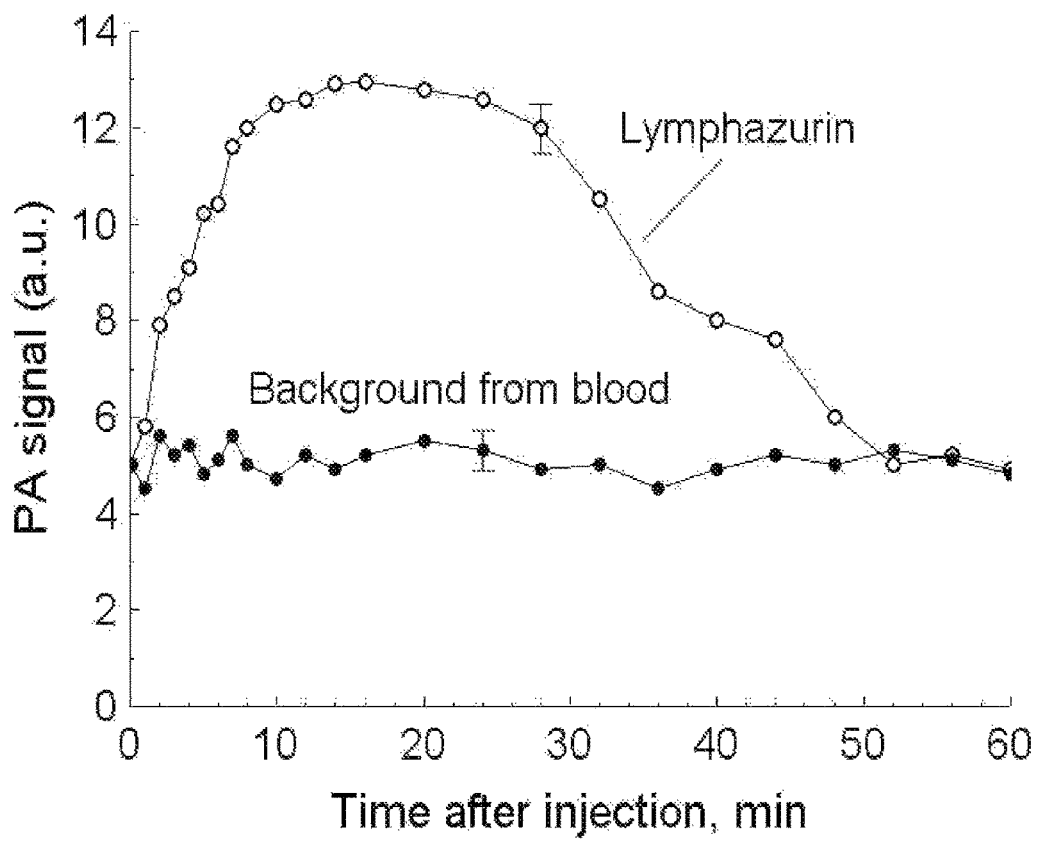
FIG. 4 shows the PA signal detected from the monitoring of the blood flow in a 50-µm rat ear microvessel with diameter after intravenous injection of Lymphazurin dye in the tail vein.

FIG. 4 summarizes the maximum PAFC signals from Lymphazurin compared to background PAFC signals from the blood vessels, observed for one hour after the injection of Lymphazurin. As shown in FIG. 4, continuous monitoring of PA signals from the ear blood microvessels revealed a rapid appearance of Lymphazurin in the blood flow within a few minutes after injection, followed by clearance of Lymphazurin from the blood over the next 50 minutes.

The results of this experiment demonstrated that the prototype PAFC system exhibited sufficient sensitivity to detect the presence of ultrasonic contrast dyes in circulation.

Example 3. Prototype In Vivo Photoacoustic Flow Cytometry System Used to Detect Nanoparticles Circulating in Rats To demonstrate the sensitivity of a prototype in vivo photoacoustic flow cytometry (PAFC) system described in Example 2 an experiment was conducted using the prototype PAFC system to detect nanoparticles intravenously injected into the tail veins of rats.

The in vivo measurements in this experiment were performed using the rat mesentery model. The rat (White Fisher, F344) was anesthetized using ketamine/xylazine at a dosage of 60/15 mg/kg, and the mesentery was exposed and placed on a heated microscope stage, and bathed in Ringer's solution at a temperature of 37° C. and a pH of 7.4. The mesentery consisted of transparent connective tissue of 7-15 µm thickness, and a single layer of blood and lymph microvessels.

The nanoparticles used in this experiment were gold nanorods (GNR), obtained from the Laboratory of Nanoscale Biosensors at the Institute of Biochemistry and Physiology of Plants and Microorganisms in Saratov, Russia. On the basis of TEM and dynamic light scattering analyses, the GNR were estimated to be approximately 15 nm in diameter and approximately 45 nm in length on average. The nanoparticles were used either uncoated, or functionalized using thiol-modified polyethylene glycol (PEG) (Liao and Hafner 2005).

A 250-µL suspension of GNR with a concentration of $10^{10}$ particles/ml was injected into the tail veins of three rats, followed by the continuous monitoring of PA signals measured from 50-µm diameter blood vessels in the rat mesentery using the PAFC system described in Example 2. PAFC measurements were taken using a laser fluence of 100 mJ/cm$^2$, a laser beam diameter of approximately 50 µm, and a laser wavelength of 830 nm, near the maximum absorption of the GNR.

Figure 5:
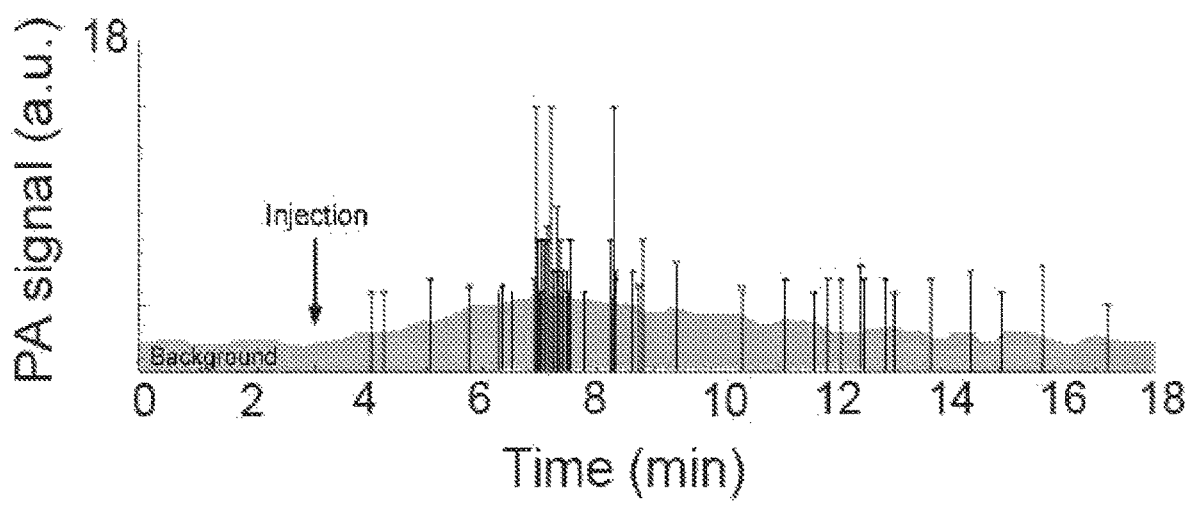
FIG. 5 shows the PA signal from circulating GNR in 50-µm rat mesentery microvessels as a function of post-injection time.

Uncoated GNR were rapidly cleared from the blood circulation within 1-3 minutes preferentially by the reticuloendothelial system (data not shown). After PEGylated GNR injection, strong fluctuating PA signals appeared with amplitudes significantly exceeding the PA background signals from blood vessels within the first minute and continued for 14-25 minutes, depending on the individual animal. In addition, the PA background signal from the blood vessel increased approximately 1.5-2 times above the pre-injection background levels, reaching a maximum level between four and nine minutes after injection, as shown in FIG. 5.

Figure 6:
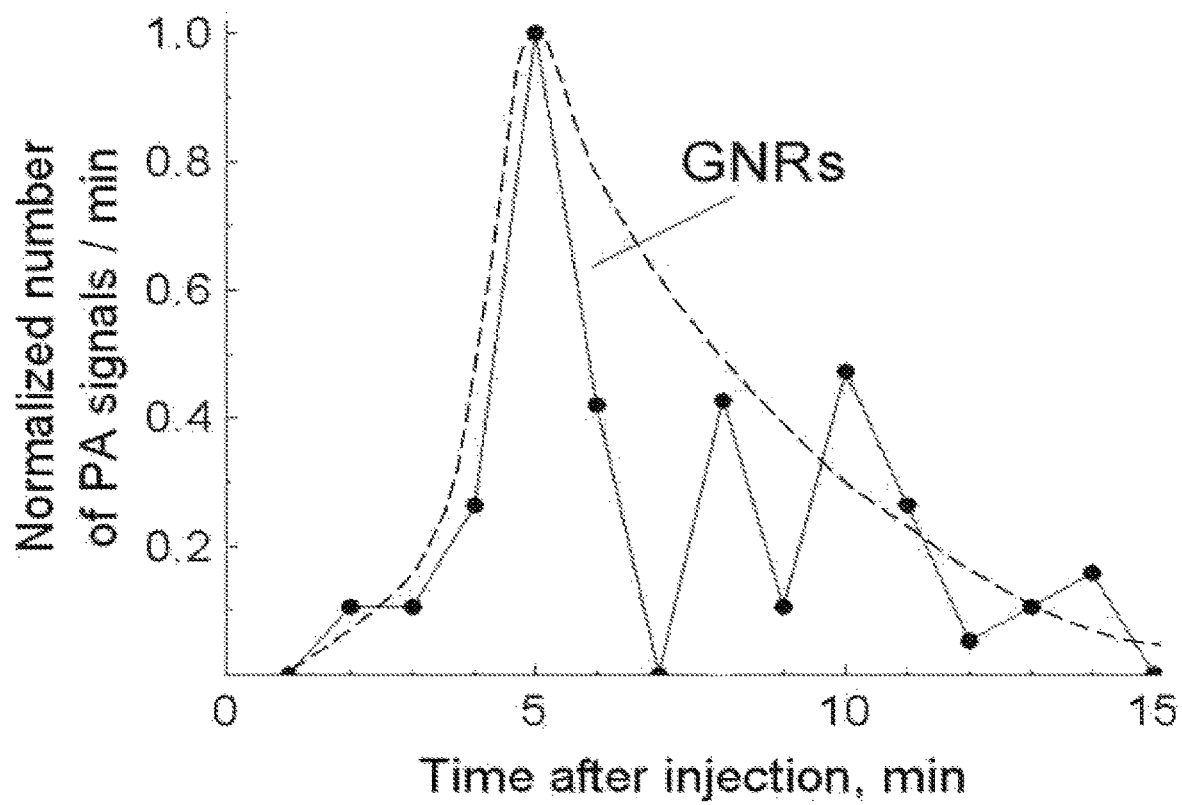
FIG. 6 is a graph of the normalized number of circulating GNR in blood microvessels of the rat mesentery as a function of post-injection time and a dashed curve showing averaged data (N=3).

The averaged PA signals from three animals, measured for 15 minutes after injection with GNR suspensions, are summarized in FIG. 6. The maximum rate of individual PA signals per minute, representing the number of GNR in circulation, was achieved approximately 5 minutes after injection, with a gradual decrease in the signal rate over the next 10 minutes.

The results of this experiment demonstrated that the prototype PAFC system possessed sufficient spatial and temporal resolution to continuously monitor the circulation of nanoparticles as small as 15 nm in diameter. In addition, the prototype PAFC system was sufficiently sensitive to track fluctuations of the concentration of circulating particles from the time that they were injected to the time that the particles were cleared from circulation.

Example 4. Prototype In Vivo Photoacoustic Flow Cytometry System Used to Detect *S. aureus* Bacteria Circulating in Mice To demonstrate the ability of the prototype photoacoustic flow cytometry (PAFC) system to detect bacteria cells in vivo under biological conditions, the following experiment was conducted. The prototype PAFC system, previously described in Example 2, was used to measure *S. aureus* bacteria in the circulation of nude mice.

The mouse ear model described in Example 2 was used for all measurements of circulating bacteria in the experiment. Because the endogenous light absorption of *S. aureus* bacteria was relatively weak compared to the absorption of other blood components in the NIR spectral range, the bacteria were labeled with the NIR-absorbing contrast substances indocyanine green dye (ICG) and carbon nanotubes (CNT), due to their relatively high labeling efficiency and low toxicity (data not shown).

The *S. aureus* bacterium strain designated UAMS-1 was isolated from a patient with osteomyelitis at the McClellan Veterans Hospital in Little Rock, Arkansas, USA. The strain was deposited with the American Type Culture Collection and is available as strain ATCC 49230. UAMS-1 was cultured in tryptic soy broth and grown aerobically for 16 h at 37° C. Cells were harvested by centrifugation, resuspended in sterile PBS and incubated with Indocyanine Green (ICG) dye (Akorn Inc., USA) or carbon nanotubes (CNT) as described below.

Before incubation, ICG dye was filtered through a 0.22 µm pore size filter. A 150-µl aliquot of bacteria in suspension was incubated with 375 µg of ICG in 150 µL of solution for 30 min at room temperature and then for 2 h at 37° C.

Labeled bacteria were centrifuged at 5,000 rpm for 3 min and the resulting pellet was resuspended in PBS.

Single-walled and multi-walled carbon nanotubes (CNT) were purchased from Carbon Nanotechnologies Inc. (Houston, TX) and Nano-lab Inc. (Newton, MA), respectively. The CNT samples used in this study were processed using known methods (Kim et al. 2006). The average length and diameter of the single-walled CNT were 186 nm and 1.7 nm respectively, and the average length and diameter of the multi-walled CNT were 376 nm and 19.0 nm respectively.

CNT solutions were treated with five cycles of 1.5 min of ultrasound at a power of 3 W followed by 0.5 min of rest, for a total of 10 minutes of interrupted ultrasound. A 150-µL aliquot of bacteria in suspension was incubated with 150 µL of CNT solution for 30 minutes at room temperature followed by 2 additional hours of incubation at room temperature. Labeled bacteria were centrifuged at 10,000 rpm for 5 min and the resulting pellet was resuspended in PBS.

Labeled 100-µl suspensions of S. aureus bacteria at a concentration of $5 \times 10^5$ cells/ml were injected into the mouse's tail vein, and the clearance of the labeled bacteria was monitored using PAFC measurements taken from 50-µm diameter microvessels in the ears of mice. Laser energy was delivered at a wavelength of 805 nm for the S. aureus that was labeled with ICG, and at a wavelength of 850 nm for the S. aureus that was labeled with CNT. For both label types, the laser energy was delivered at a beam diameter of approximately 50 µm and at a fluence ranging between 20 and 50 $mJ/cm^2$.

Figure 7:
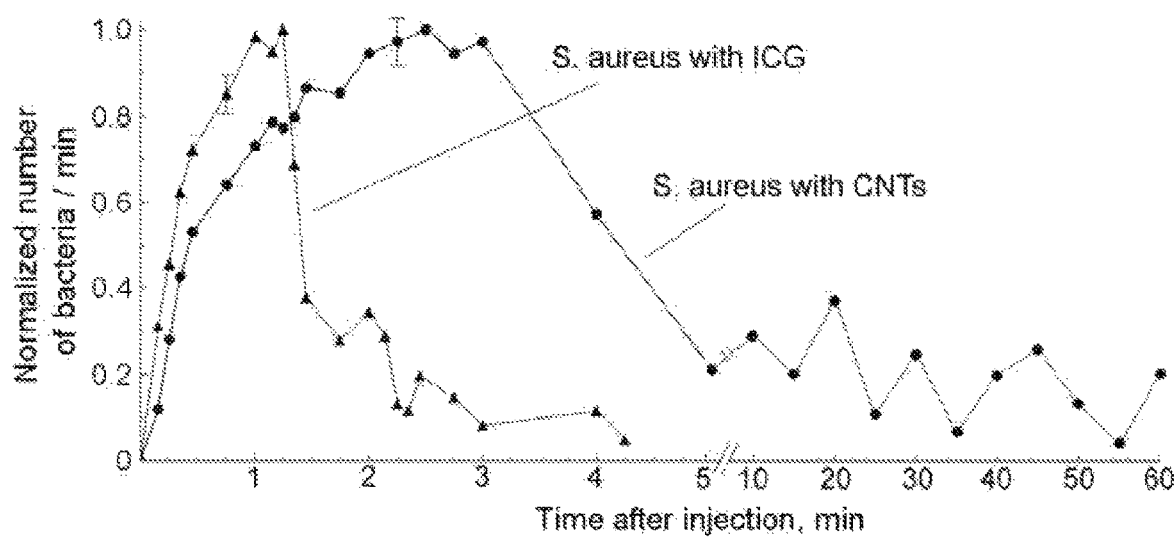
FIG. 7 is a graph of the normalized number of circulating *S. aureus* in blood microvessels of the mouse ear as a function of post-injection time, for bacteria labeled using two different contrast substances, ICG dye and CNT.

S. aureus bacteria labeled with ICG and CNT contrast substances yielded similar results, summarized in FIG. 7. After injection of labeled S. aureus, PAFC detected a rapid appearance of bacteria in the ear blood microvessels within the first minute, followed by a steady elimination of the bacteria from the blood circulation over the next 3-5 minutes. Periodic PAFC monitoring of mice blood vessels over the next few days revealed that very rare bacteria labeled with CNT or possibly unattached CNT continued to appear at an average rate of one PA signal every three minutes, and the labeled bacteria or CNT was not completely cleared from circulation until about 60 hours after the initial injection (data not shown).

The results of this experiment established the feasibility of PAFC for the in vivo monitoring of individual cells in the circulatory systems of living organisms. Using appropriate contrast enhancement substances, the laser fluence required for effective detection of cells in circulation was well below the threshold levels for laser-induced cell damage.

Example 5. Prototype In Vivo Photoacoustic Flow Cytometry System Used to Detect E. coli Bacteria Circulating in Mice To demonstrate the ability of the prototype photoacoustic flow cytometry (PAFC) system to detect bacteria cells in vivo under biological conditions, the following experiment was conducted. The prototype PAFC system, previously described in Example 2, was used to detect the bacteria E. coli strain K12, in the circulation of nude mice.

The mouse ear model described in Example 2 was used for all measurements of circulating bacteria in the experiments described below. Because the endogenous light absorption of E. coli bacteria was relatively weak compared to the absorption of other blood components in the NIR spectral range, the bacteria were labeled with NIR-absorbing carbon nanotubes (CNT).

E. coli K12 strain was obtained from the American Type Culture Collection (Rockville, MD) and maintained in Luria-Bertani (LB) medium, a solution consisting of 1% tryptone, 0.5% yeast extract, and 0.5% NaCl at a pH of 7. A 100-µl aliquot of E. coli in PBS was incubated with 100 µL of the CNT solution as described in Example 4 for 60 min at room temperature.

Figure 8:
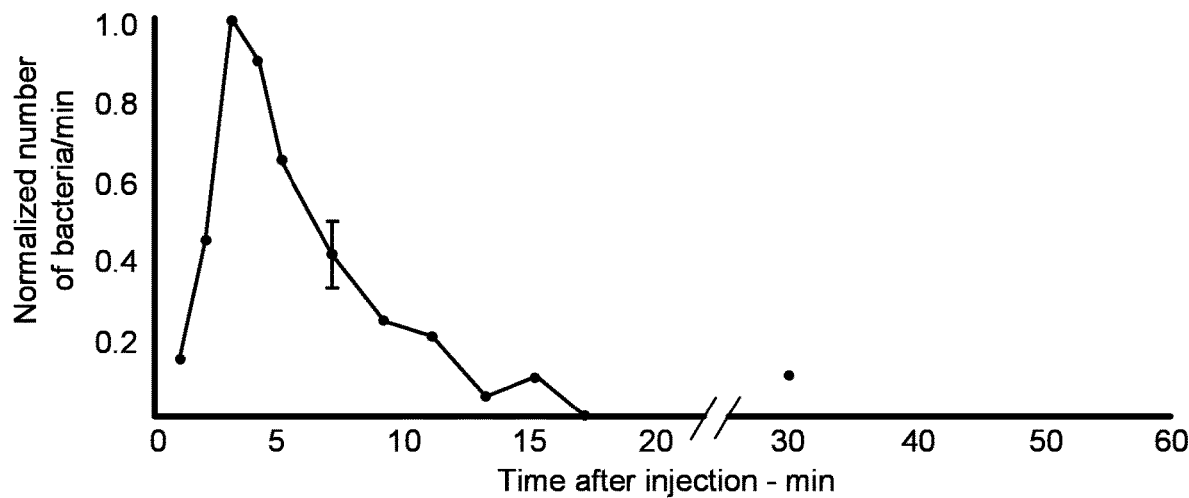
FIG. 8 is a graph of the normalized number of circulating *E. coli* in blood microvessels of the mouse ear as a function of post-injection time.

100-µl suspensions of CNT-labeled E. coli bacteria at a concentration of $5 \times 10^5$ cells/ml were injected into the mouse's tail vein, and the clearance of the labeled bacteria was monitored using PAFC measurements taken from 50-µm diameter microvessels in the ears of mice. Laser energy was delivered at a wavelength of 850 nm, a beam diameter of approximately 50 µm and at a laser fluence of 100 $mJ/cm^2$. PAFC measurements, summarized in FIG. 8, detected a rapid appearance of the bacteria in circulation after injection, and the bacterial concentrations in the blood decreased exponentially over the next 15-17 minutes.

The results of this experiment confirmed the feasibility of PAFC for the in vivo monitoring of individual cells in the circulatory systems of living organisms. The laser fluence required for effective detection of E. coli cells in circulation was well below threshold levels for laser-induced cell damage.

Example 6. In Vivo PAFC Used to Detect Circulating Exogenous Melanoma Cells

To demonstrate the ability to use in vivo PAFC to detect unlabeled melanoma cells in circulation with extremely high sensitivity through skin cells with varying levels of melanin pigmentation, the following experiment was conducted.

B16F10 cultured mouse melanoma cells (ATCC, Rockville, MD) were used in this experiment. The cells were maintained using standard procedures (Ara et al. 1990, Weight et al. 2006, Zharov et al. 2006), including serial passage in phenol-free RPMI 1640 medium (Invitrogen, Carlsbad, CA) supplemented with 10% fetal bovine serum (FBS, Invitrogen). For comparison to the detection of unlabeled melanoma cells, the endogenous cell absorption was increased by staining with ICG (Akorn Inc., USA), a strongly absorbent dye in the NIR range, for 30 min at 37° C. and in the presence of 5% $CO_2$. No toxicity was observed after labeling as assessed using the trypan blue exclusion assay (data not shown).

Figure 9:
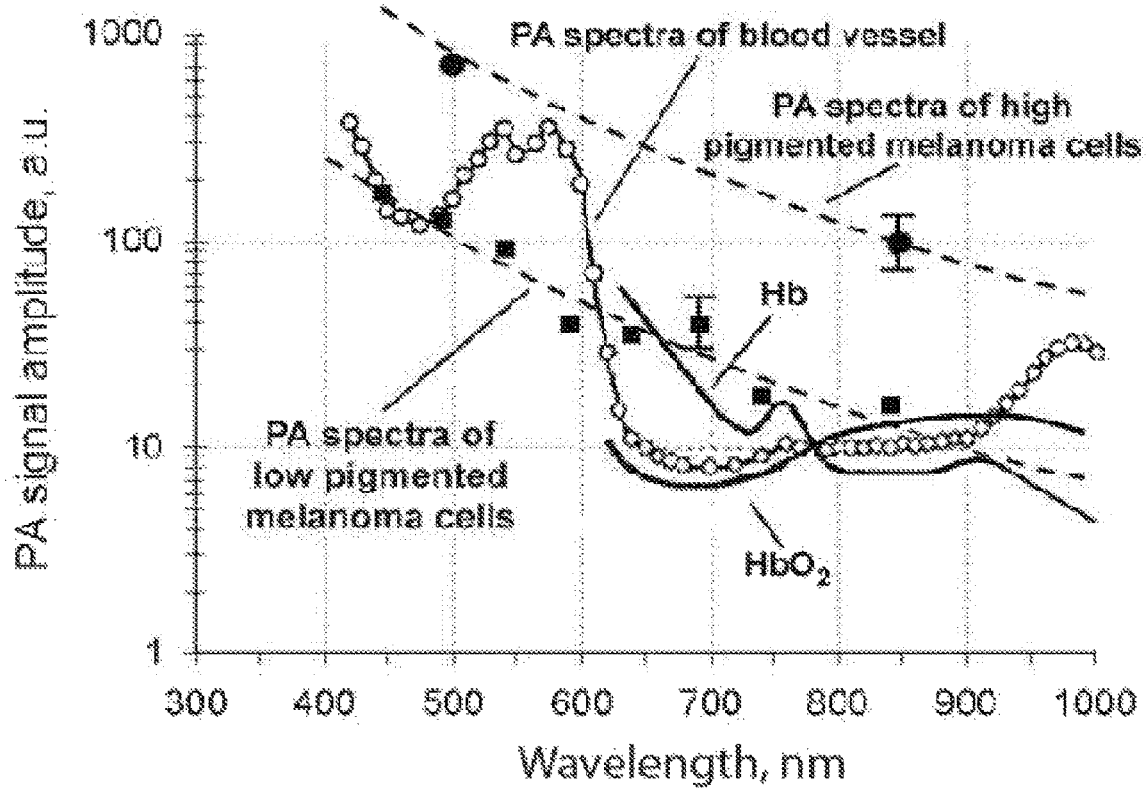
FIG. 9 shows the PA spectra of 50-µm diameter veins in the mouse ear (empty circles), conventional absorption spectra of the B16F10 mouse melanoma cells with strong pigmentation (upper dashed curve) and weak pigmentation (lower dashed curve), spectra normalized using PA signals for the single mouse melanoma cells with strong pigmentation (black circles) and weak pigmentation (black squares), and absorption spectra for pure Hb and $HbO_2$ (fragments of solid curves in the spectral range 630-850 nm).

In vivo measurements of melanoma cells used the PAFC system previously described in Example 2 with a laser wavelength of 850 nm and a laser fluence of 80 $mJ/cm^2$. This wavelength falls within a region in which the absorbance of melanoma cells is relatively high compared to the absorbance of hemoglobin, a major component of blood, as determined by in vitro measurements summarized in FIG. 9.

To estimate the influence of endogenous skin melanin on PAFC detection limits, Harlan Sprague mice, strain: NIH-BG-NU-XID were used in this experiment. Female mice of this strain possess high levels skin pigmentation between 8 and 10 weeks of age. Mice were anaesthetized and placed on the heated microscope stage as previously described in Example 2.

Figure 10A:
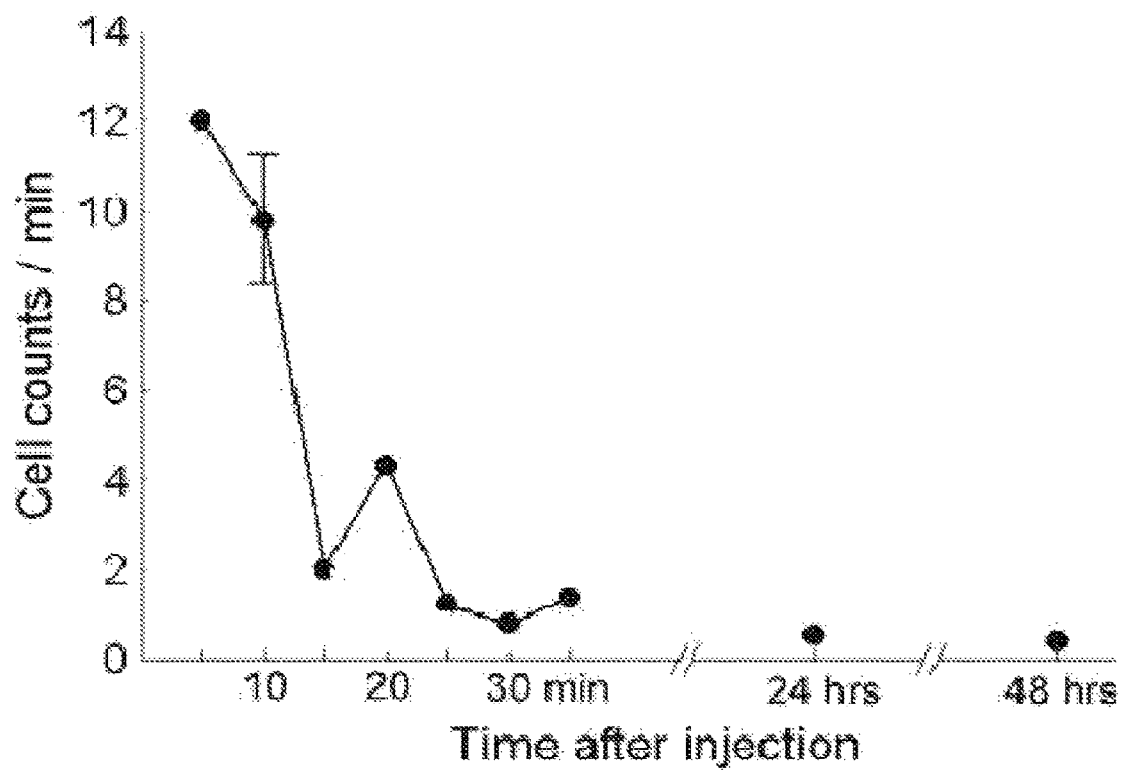
FIG. 10A-FIG. 10B is a graph showing the frequencies of circulating mouse melanoma cells (B16F10) detected with label-free PAFC in 50-µm mouse ear veins, with a flow velocity of 5 mm/s, in mice with low (FIG. 10A) and high (FIG. 10B) melanin pigmentation as a function of post-injection time.
Figure 10B:
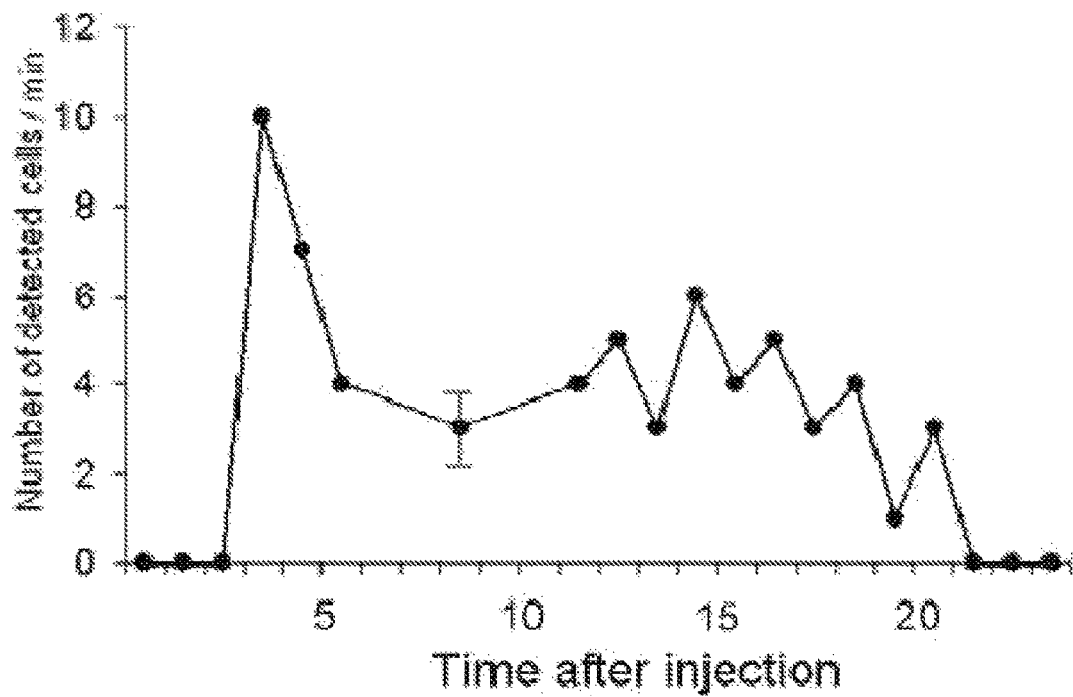

A 200-µl volume of saline solution containing approximately $10^5$ mouse melanoma cells was injected into the mouse circulatory system through a tail vein and then monitored using the PAFC system. The number of melanoma cells per minute detected using PAFC for melanoma cells after injection are summarized in FIG. 10 for melanoma cells with low melanin content (FIG. 10A) and for melanoma cells with high melanin content (FIG. 10B). In the first 5 minutes of PA detection following intravenous injection of cultured mouse melanoma cells, 600±120 PA signals (representing melanoma cells) per hour were observed, and the rate of detection of melanoma cells steadily decreased over the subsequent 20-30 min. Approximately 20 cells/hour and 4 cells/hour were detected after 24 h and 48 h of monitoring, respectively. The initial PA signal rate after the injection of melanoma cells stained with ICG contrast enhancement substances was 720±105 cells/hour (data not shown). Assuming that all stained melanoma cells were detected by in vivo PAFC, 82.4% of the unlabeled melanoma cells in circulation were detected by in vivo PAFC measurements.

The results of this experiment demonstrated the ability of in vivo PAFC to detect and monitor the appearance and progression of metastatic melanoma cells in circulation non-invasively.

Example 7. In Vivo PAFC was Used to Detect Circulating Spontaneous Metastatic Cells During Tumor Progression An experiment was conducted to determine the ability of in vivo PAFC to detect relatively scarce endogenous metastatic melanoma cells circulating in lymph vessels. The PAFC system described in Example 2 was used to monitor endogenous metastatic melanoma cells in mice. The laser characteristics used in this experiment are identical to those described in Example 5.

Nude mice were anaesthetized and placed on the heated microscope stage as previously described in Example 2. The ear blood vessels under examination were located 50-100 μm deep and had diameters of 35-50 μm with blood velocities of 3-7 mm/sec. To increase the probability of detection of rare metastatic cells, blood vessels with relatively large diameters of 150-300 μm and flow velocities up to 10-30 mm/s in the skin of the abdominal wall were examined using a customized skin fold chamber.

50-μl suspensions containing $10^6$ B16F10 cultured mouse melanoma cells (ATCC, Rockville, MD) were subcutaneously injected into nude mice. Melanoma tumors subsequently formed in the ears of the mice and in the skin on the backs of the mice. PAFC was performed on ear and abdominal blood vessels to monitor the circulatory system for the appearance of metastatic cells, and PA mapping, described below, was used to monitor the growth of tumors.

During ear tumor development, individual or groups of melanoma cells were first detected in the skin area close to the tumor site on the sixth day following tumor inoculation using PA mapping measurements. PA mapping measurements utilized PA signals derived by scanning a focused laser beam with diameter of 10 μm across ear. Metastatic cells first appeared in ear microvessels near the tumor on the twentieth day after inoculation at a rate of 12±5 cells/hour (data not shown). Surprisingly, during the same time period, no melanoma cells had yet been detected in the abdominal skin blood vessels. 25 days after inoculation, the average count of melanoma cells detected in the ear veins increased to 55±15 cells/hour, and at this same time, melanoma cells were detected in abdominal wall skin vessels at a rate of 120±32 cells/hour. Thirty days after inoculation, the detection rate decreased to 30±10 cells/hour in the abdominal vessel, which may be attributed to inhibition of metastatic cell production in the primary tumor. PA mapping of selected tissue and organs revealed multiple micrometastases in cervical and mesenteric lymph nodes, as well as in lung and liver tissues.

PAFC measurements of the nude mouse back tumor model revealed the appearance of metastatic melanoma in abdominal skin blood vessels close to the tumor site on day 5, much earlier than in the tumor ear model. This indicates a much greater likelihood of detecting the initial metastatic process in the vicinity of the primary tumor.

Thirty days after tumor inoculation, the average concentration of melanoma cells was 150±39 cells/ml, corresponding to a circulating rate of approximately 4-10 cells/min in a 50-mm blood vessel and a flow velocity of 5 mm/s. The ultimate PAFC threshold sensitivity of the nude mouse back tumor model was estimated as 1 cell/ml. This circulating rate corresponded to an incidence of approximately one melanoma cell among 100 million normal blood cells.

The results of this experiment indicated that in vivo PAFC and PA mapping were sensitive methods with which to monitor the development of metastasized melanoma cells non-invasively, with high sensitivity and accuracy.

Example 8. In Vivo PAFC was Used to Detect Spontaneous Metastatic Cells in Lymphatic Vessels During Tumor Progression To determine the feasibility of detecting individual metastatic cells in lymph flow, the following experiment was conducted. A photoacoustic flow cytometer (PAFC) was used to monitor lymph flow for the presence of WBC, RBC, and metastatic melanoma cells.

The animal models used in this experiment were nu/nu nude mice, weighing 20-25 g (Harlan Sprague-Dawley). PAFC measurements were taken using the lymphatic vessels in the ears using a heated platform as described in Example 2. Melanoma tumors in the ear and back skin of the mice were induced by the subcutaneous injection of B16F10 mouse melanoma cells as described in Example 6.

To locate the lymphatic vessels in the mouse ear, a PA mapping process using a PA contrast agent was used. Ethylene blue (EB) dye, commonly used for lymphatic research, was injected into the lymphatic vessel walls. A 639 nm laser beam was then used to illuminate the lymphatic vessel at a wavelength of 639 nm, corresponding to the maximum absorption of EB dye, and the resulting PA signal emitted by the EB dye was monitored. The position of the laser beam on a lymph vessel was fixed when the PA signal amplitude reached its maximum at the laser wavelength of 639 nm.

Figure 11:
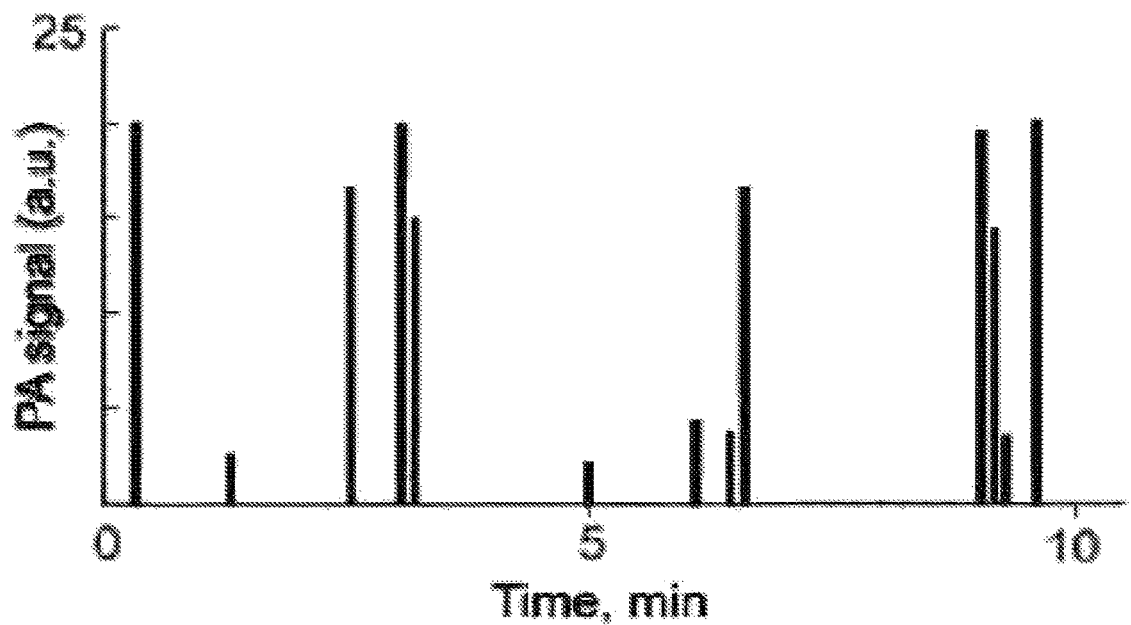
FIG. 11 is a summary of the PA signal rates from single melanoma cells detected in a mouse ear lymph microvessel 5 days after tumor inoculation.

In vivo PAFC detection of unlabeled melanoma cells relied on melanin as an intrinsic cell marker, as in Example 7. Melanoma cells were detected using a laser wavelength of 850 nm, a laser fluence of 35 mJ/cm$^2$, and a laser beam diameter of approximately 50 μm. In mice with induced skin melanomas, metastatic cells were observed to appear in a lymphatic vessel of the mouse's ear on the fifth day after inoculation at a rate of 1.2±0.5 cells/min, which steadily increased over the course of 2 weeks (data not shown). In mice with a melanoma tumor in the ear, melanoma cells appeared in skin lymphatics 20 days after inoculation. 30 days after inoculation strong PA signals detected the presence of metastatic melanoma cells in the sentinel lymph nodes, which was later confirmed by histology (data not shown). FIG. 11 shows the PA signals detected from single metastatic melanocytes circulating in the lymphatic vessel in the mouse ear five days after tumor inoculation.

The results of this experiment demonstrated the feasibility of detecting relatively scarce metastatic melanoma cells circulating in the lymphatic system using in vivo PAFC techniques, with high sensitivity and accuracy.

Example 9. In Vivo PAFC was Used to Detect Red Blood Cells and Lymphocytes Simultaneously Circulating in Lymph Vessels To determine the feasibility of detecting unlabeled individual cells of different types circulating in lymph flow, the following experiment was conducted. A photoacoustic flow cytometer (PAFC) was used to monitor lymph flow for the presence of red blood cells and lymphocytes.

The animal models used in this experiment were 150-200 g rats (Harlan Sprague-Dawley). PAFC measurements were taken using lymphatic vessels in the mesentery of the rat, using the method described in Example 3. Lymphatic vessels were located, and the laser was focused on the lymphatic vessel using the methods described in Example 8.

Spectroscopic studies in vitro revealed that PA signals from lymphocytes reached maximal amplitude in the visible-spectral range near 550 nm, associated with cytochrome c acting as an intrinsic absorption marker (data not shown). Background PA signals from vessels and surrounding tissues were approximately 4-6-fold less than from single lymphocytes at this wavelength due to the low level of background absorption and laser focusing effects.

Figure 12:
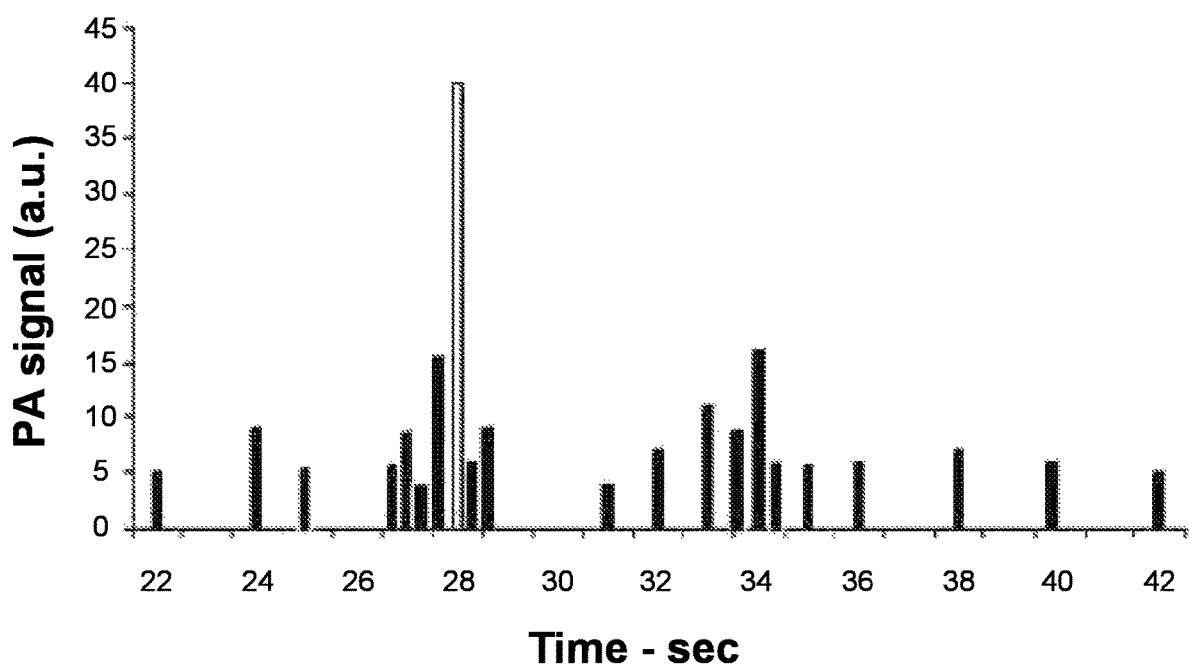
FIG. 12 is a summary of the PA signal rates from a single RBC (white bar) and lymphocytes (black bars) detected by PAFC in the lymph flow of rat mesentery.

The in vitro PAFC system described in Example 2 was used to detect circulating cells in the lymphatic vessels of the rat mesentery. The laser used in the PAFC system had a wavelength of 550 nm and a fluence of 100 mJ/cm$^2$, and a circular beam diameter of approximately 50 µm. The cell detection rate obtained in lymphatic vessels was 60±12 cells/min. A graph showing the PA signals detected by the PAFC system in a rat mesentery lymphatic vessel is shown in FIG. 12. Lymphocyte heterogeneity resulted in 2-2.5-fold fluctuations in PA signal amplitude from cell to cell. A small fraction of the detected cells had strong PA signal amplitudes exceeding those of the lymphocyte signals by a factor of 10 to 20-fold. One such strong PA signal is shown as a white bar in FIG. 12 at 28 seconds. Subsequent spectral and imaging analysis identified rare single red blood cells (RBCs) as the sources of these excessively strong PA signals.

The results of this experiment demonstrated that the in vivo PAFC system possessed sufficient sensitivity and accuracy for the simultaneous detection of red blood cells and lymphocytes circulating in the lymphatic vesicles.

Example 10. In Vivo Two-Wavelength PAFC was Used to Discriminate Between 3 Different Exogenously Labeled Cell Types in Circulation within Lymph Vessels To demonstrate the ability of the photoacoustic flow cytometry (PAFC) system to detect cells using more than one wavelength of laser light, the following experiment was conducted. In this experiment, a PAFC system was used to detect exogenous blood cells that were labeled with three different nanoparticles, while circulating in blood vessels (data not shown) and in lymphatic vessels. The PAFC system detected the cells by illuminating the cells with laser pulses of two different wavelengths in the near-infrared (NIR) spectrum.

A PAFC system similar to that described in Example 2 was used to detect the circulating cells. However, in the PAFC system used in this experiment, the laser of the PAFC system pulsed light at two different wavelengths, corresponding to the wavelengths of maximum absorption for two of the nanoparticles used to label the cells. The first laser pulse was at a wavelength of 865 nm, a laser fluence of 35 mJ/cm$^2$, and pulse duration of 8 ns. 10 µs after the end of the first laser pulse, a second laser pulse was delivered at a wavelength of 639 nm, a laser fluence of 25 mJ/cm$^2$, and pulse duration of 12 ns. The paired laser pulses were repeated at a frequency of 10 Hz.

The animal models used in this experiment were nu/nu nude mice, weighing 20-25 g (Harlan Sprague-Dawley). PAFC measurements were taken using lymphatic vessels in the mesentery of the mouse, using the methods described in Example 3. Lymphatic vessels were located, and the laser was focused on the lymphatic vessel using the methods described in Example 8.

Normal fresh blood cells were obtained from heparinized whole-blood samples of donor mice after terminal blood collection. Red blood cells were isolated by simple centrifugation, and lymphocytes were isolated by Histopaque (Sigma-Aldrich) density gradient centrifugation as recommended by the supplier.

The nanoparticles used to label the various blood cells used in this experiment were gold nanorods (GNR) and gold nanoshells (GNS), provided by The Laboratory of Nanoscale Biosensors at the Institute of Biochemistry and Physiology of Plants and Microorganisms in Saratov, Russia. The GNR had an average diameter of 16 nm, an average length of 40 nm, and a relatively narrow absorption band of 660±50 nm. The GNS had an average diameter of 100 nm, and a maximum absorption near 860 nm. Both GNR and GNS were coated with polyethylene glycol in the process described in Example 3. Single-walled CNT with an average length of 186 nm and an average diameter of 1.7 nm were purchased from Carbon Nanotechnologies Inc. CNT absorb laser energy over a wide range of wavelengths with an efficiency that monotonically decreases as wavelength increases. All particles were in suspension at a concentration of about $10^{10}$ nanoparticles/ml.

Live neutrophils were labeled with the GNS, live necrotic lymphocytes were labeled with the GNR and apoptotic lymphocytes were labeled with the CNT. The cells were labeled by incubating 100-µl aliquots of each cell type in phosphate-buffered saline with 100 µL of CNT, GNR, or GNS for 15 min at room temperature.

The labeled cells, mixed in approximately equal proportions, were intravenously injected into the tail vein of the mouse. After 6 h, mesenteric lymphatics were illuminated with two laser pulses at wavelengths of 865 nm and 639 nm as described above. PA signals at a rate of 1-3 signals/min were detected at this time.

Figure 13A:
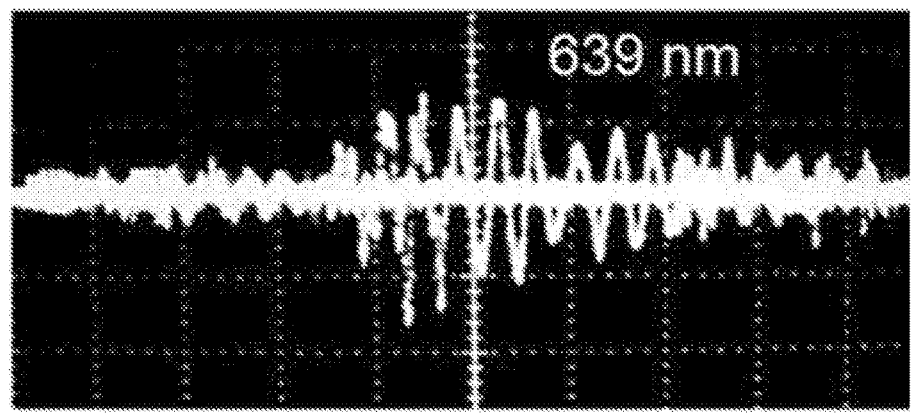
Figure 13B:
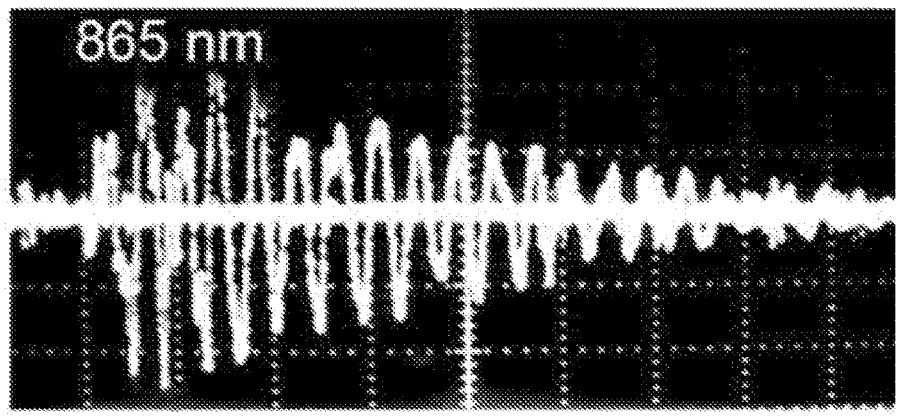
Figure 13C:
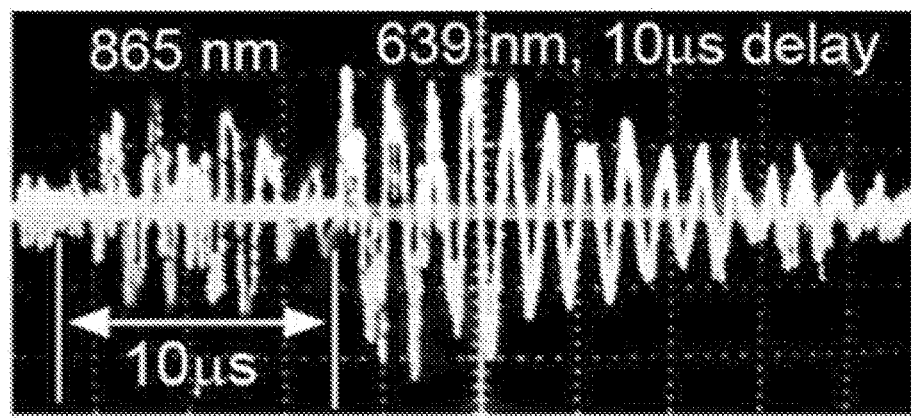

The PA signals had one of three distinctive temporal shapes associated with the response of the three different labels to the paired laser pulses, shown in FIG. 13. PA signals from necrotic lymphocytes marked with GNR were generated in response to the 639 nm laser pulse only, after a 10-µs delay, as shown in FIG. 13A. The apoptotic lymphocytes marked with GNS generated PA signals in response to laser pulse at a wavelength of 865 nm with no delay, as shown in FIG. 13B. Live neutrophils marked with CNT generated two PA signals after a 10-µs delay, as shown in FIG. 13C. One signal was generated in response to the 639 nm laser pulse, and the second PA signal was generated in response to the 850-nm laser pulse, due to comparable CNT absorption at both wavelengths.

The results of this experiment demonstrated that with the use of various contrast substances and two wavelength cell identification techniques, the in vivo PAFC apparatus detected and discriminated between live neutrophils, necrotic lymphocytes, and apoptotic lymphocytes that were circulating in the lymphatic vessels. This method may also be extended to unlabeled cells circulating in the lymphatic or circulatory systems, using a pair of laser pulse wavelengths selected to generate a unique PA signal shape for each cell type to be detected.

Example 11. Spatial Resolution and Maximum Detectible Vessel Depth of a Prototype In Vivo PAFC System was Assessed To determine the maximum spatial resolution and maximum detectible vessel depth of the PAFC system, the following experiment was conducted using the prototype PAFC system described in Experiment 2 and the mouse ear model with circulating melanoma cells, as described in Example 7. Mouse melanoma cells were injected into the tail veins of nude mice and PAFC measurements were conducted as described in Example 7.

The PAFC system achieved a lateral resolution of 5-15 µm when detecting melanoma cells circulating in mouse ear blood vessels with diameters of 10-70 µm at depths of 50-150 µm. However, when melanoma cells circulating in mouse ear blood vessels at a depth of 0.5 mm were measured, the lateral resolution decreased to 30-50 µm due to the scattering of the 850 nm laser pulses by the additional tissue between the PAFC laser and the targeted blood vessels.

The maximum potential of the PAFC to detect cells circulating in deep vessels was estimated by overlaying layers of mouse skin of varying thickness over intact mouse skin containing peripheral blood vessels at a depth of approximately 0.3 mm below the surface of the intact skin. Using the PAFC system described in Example 2 with an unfocused ultrasound transducer (Panametrics model XMS-310, 10-MHz), PA signals were detected at total skin thicknesses up to approximately 4 mm, with a 27-fold signal attenuation due to light scattering. When a focused ultrasound transducer was used (Panametrics model V316-SM, 20 MHz, focal length 12.5 mm), PA signals were detected from melanoma cells circulating in the mouse aorta at a depth of approximately 2.5 mm, resulting from a laser pulse wavelength of 850 nm. Even at a total tissue depth as high as 11 mm, the PA signals emitted by circulating metastatic melanoma cells illuminated by 532 nm laser pulses remained discernible from the background PA signals from surrounding tissues. The lateral resolution at this vessel depth, measured by changing the angle of the ultrasonic transducer, was estimated to be approximately 250 µm (data not shown).

The results of this experiment demonstrated that the PAFC system was capable of detecting circulating melanoma cells at a vessel depth of up to 11 mm with a resolution of approximately 250 µm. This resolution may be improved significantly through the use of higher frequency ultrasound transducers, such as 50 MHz transducers.

Example 12. The Sensitivity of the Spatial Resolution of a Prototype In Vivo PAFC Device to Skin Pigmentation Levels was Assessed Using the Nude Mouse Model To determine the sensitivity of the PAFC system to the level of skin pigmentation, the following experiment was conducted. The PAFC device described in Example 2 was used to measure PA signals from blood vessels in nude mice skin with low and high levels of pigmentation using methods similar to those described in Example 7.

In the low-pigmented nude mouse model, the background PA signal from skin cells was very weak. PA signals measured by a high frequency ultrasound transducer (Panametrics model V-316-SM, 20 MHz) resulting from the simultaneous irradiation of two circulatory vessels at depths of approximately of 0.3 mm and 2.4 mm, were determined to have a time separation of approximately 1.4 ms. This delay is consistent with signals emitted by cells with a separation distance of 2.1 mm, assuming a velocity of sound in soft tissue of approximately 1.5 mm/ms. Similar results were obtained for measurements of circulatory vessels in the highly pigmented nude mouse model (data not shown).

The results of this experiment demonstrated that the level of skin pigmentation did not significantly affect the spatial resolution of the PAFC device. For strongly pigmented skin, the assessment of deeper vessels may actually be enhanced because the skin pigmentation may facilitate the discrimination between PA signals from circulating individual cells and PA signals from the skin.

Example 13. Methods of Enriching the Incidence of Circulating Metastatic Cells Measured by PAFC In Vivo were Demonstrated Using the Mouse Ear Model To determine the feasibility of novel methods for increasing the concentrations of circulating metastatic cells detected by the in vivo PAFC device, the following experiment was conducted. Using the mouse ear model to measure the incidence of circulating metastatic melanoma cells, as described in Example 7, the effect of gentle mechanical squeezing of blood microvessels was assessed. This method of enriching the local incidence of rare circulating cancer cells in vivo exploited the size differences between melanoma cells (16-20 mm), WBC (7-8 mm), and RBC (5-6 mm) and the high deformability of RBC compared to cancer cells. The lumen size of the microvessel was decreased to 10-15 µm through gentle mechanical squeezing of blood microvessels in 50-µm microvessels of mouse ear. After squeezing a 50-µm mouse ear blood vessel for 10 min, then quickly releasing the vessel, the rate of metastatic melanoma cells measured by PAFC immediately after vessel release increased approximately 8-fold, relative to the rate measured before squeezing. The degree of blood vessel squeezing could be controlled by monitoring increases and decreases in PA signal amplitudes.

The results of this experiment demonstrated that local enrichment of circulating metastatic melanoma cells was achieved through the mechanical restriction of circulatory vessels.

Example 14. The Background Absorption by Surrounding Blood Cells was Manipulated by Changes in Blood Oxygenation, Hematocrit, and Blood Osmolarity To determine the effects of changes in blood oxygenation, hematocrit, and osmolarity on the background absorption of blood cells during in vivo PAFC, the following experiment was conducted. The absorption of laser energy by hemoglobin in its oxygenated ($HbO_2$) and deoxygenated (Hb) forms differs, depending on the oxygen saturation state of the hemoglobin and the wavelength of the laser pulse. The total absorption of red blood cells decreases as oxygenation increases for laser pulse wavelengths 810-900 nm, and the absorption of red blood cells decreases with increasing blood oxygenation at laser pulse wavelengths of 650-780 nm. Thus, the oxygenation of the red blood cells can be manipulated to minimize the background PA signals emitted by the red blood cells.

Pure oxygen was delivered to a mouse using a mask around the mouse's head, and the background PA signal obtained before and after the increased blood oxygenation was measured using the in vivo PAFC system described in Example 2. The increased blood oxygenation resulting from the exposure of the mouse to pure oxygen for 15 minutes caused the background PA signal from veins to decrease by a factor of $1.36\pm0.14$, using a laser pulse wavelength of 750 nm. Replacing the delivery of pure oxygen with the delivery of pure nitrogen led to a 35% decrease in background PA signal in an arteriole at a laser pulse rate of 900 nm.

Another experiment was conducted to assess the effects of decreasing the density of the circulating RBC as measured by the hematocrit on the background signal from circulating red blood cells. The hematocrit of a mouse's blood was temporarily reduced by the intravenous injection of 0.5 ml of standard saline solution into the vein tail. After the saline injection, PA signals from a 50-µm ear mouse vein dropped by a factor of $2.3\pm0.3$, and nearly returned to initial levels within about 1.5 minutes.

Blood osmolarity causes an increase in the RBC volume (swelling) that resulted in a decrease in the average intracellular Hb concentration. Injection of 100-mL of hypertonic NaCl solution into the mouse tail vein led to an approximately 2-fold decrease in the PA signal in the ear vein.

The results of this experiment demonstrated that the background PA signals resulting from the emission of PA signals by red blood cells may be minimized by manipulation of the chemical environment of the blood, including blood oxygenation, hematocrit, and blood osmolarity. These approaches may be readily applicable to human subjects because the procedures used in this experiment are routinely used in clinical practice.

Example 15. Microbubbles Conjugated with Nanoparticles were Assessed as a Contrast Agent for PAFC To assess the effectiveness of microbubbles conjugated with nanoparticles as a contrast agent in PAFC, the following experiment was conducted. Microbubbles (Definity Inc.) with average diameters of 2-4 µm were incubated with PEG-coated gold nanoshells (GNS), previously described in Example 10 for 1 hour at room temperature. The measurement of PA signals in vitro, as described in Example 1 was conducted for microbubbles only, GNS only and microbubbles conjugated with GNS. The microbubbles conjugated with GNS emitted the strongest PA signals, the GNS only emitted somewhat weaker PA signals, and the microbubbles alone emitted negligible PA signals (data not shown).

Increasing the energy of the laser pulses illuminating the GNS-conjugated microspheres led to a dramatic increase of the emitted PA signals, followed by the disappearance of the microbubbles after a single laser pulse. This observation was attributed to the laser-induced overheating of the GNS leading to a dramatic temperature increase of the gas trapped inside of the microbubbles that ultimately ruptured the microbubbles.

The results of this experiment demonstrated that microbubbles conjugated with GNS were an effective contrast agent, but that the energy of the laser pulses must be carefully moderated to avoid bursting the microbubbles. Because the microbubbles may be selectively attached to blood clots or taken up by activated white blood cells, this contrast agent may expand the potential applications of in vivo PAFC to include the detection of blood clots and certain activated white blood cells.

Example 16. Two-Wavelength In Vivo PAFC Used to Detect Circulating Exogenous Melanoma Cells To demonstrate the ability to use two-wavelength in vivo PAFC to detect injected unlabeled melanoma cells in circulation with extremely high sensitivity, the following experiment was conducted. B16F10 cultured mouse melanoma cells (ATCC, Rockville, MD) were obtained and maintained as described in Example 6. The experiments were performed using a nude mouse ear model similar, described in Example 2 (n=25). To mimic metastatic cells, approximately $10^5$ tumor-derived B16F10 cells in a 100-µl volume of saline solution were injected into the mouse circulatory system through a tail vein and then monitored in an ear vein using an apparatus and methods similar to those described in Example 10. An ear blood vessel was illuminated by two laser pulses at wavelengths of 865 nm and 639 nm with a 10-ms delay between the pulses.

Figure 14A:
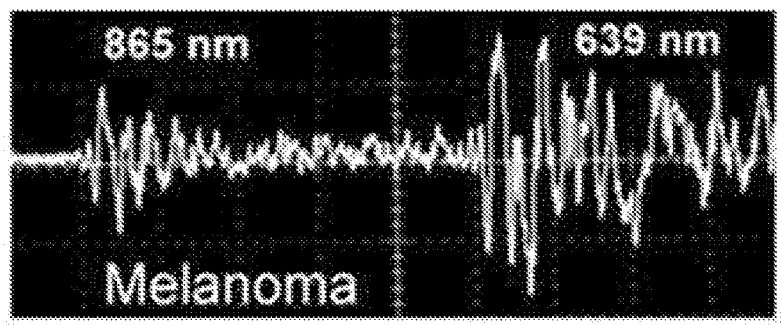
Figure 14B:
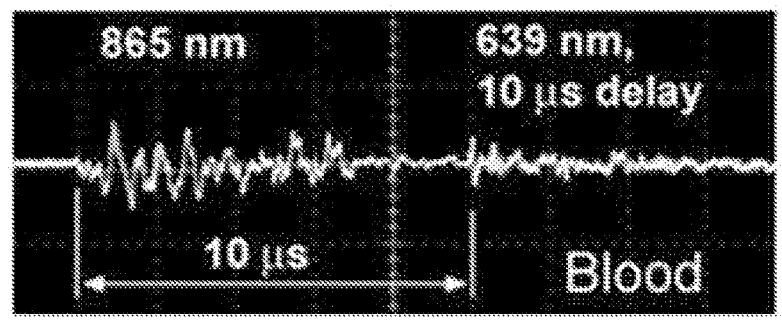

The melanoma cells were distinguished from surrounding blood cells, based upon the distinctive absorption spectra of the melanoma cells, as described previously in Example 6 and summarized in FIG. 9. Melanoma cells emitted two PA signals with a 10-ms delay, corresponding to the two laser pulses. The first PA signal, induced by the 639 nm laser pulse, had a higher amplitude than the PA signal induced by the 865 nm pulse, as shown in FIG. 14A. Red blood cells, the most numerous blood cells in circulation, generated two PA signals with lower amplitudes than the corresponding PA signals generated by the melanoma cells. In addition, for the red blood cells, the amplitude of the PA signal induced by the 865 nm pulse was slightly higher than the PA signal induced by the 639 nm laser pulse, as shown in FIG. 14B.

Figure 15:
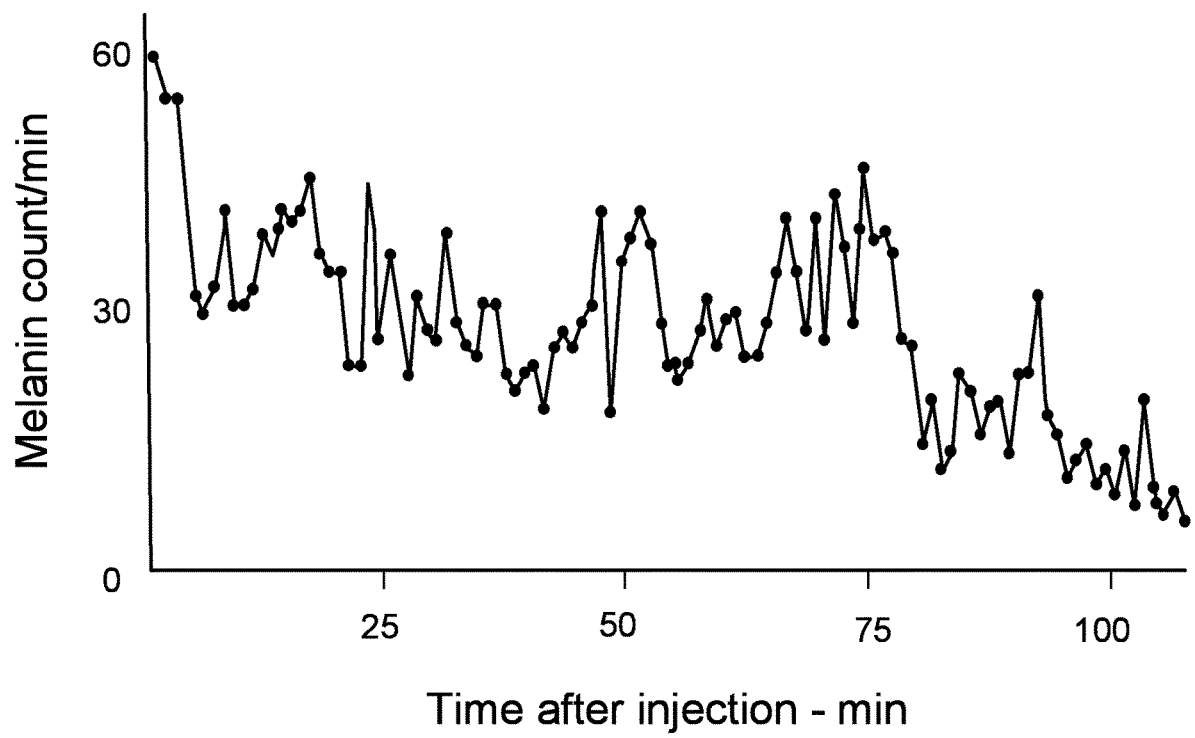
FIG. 15 is a summary of the PA signal rates from melanin particles detected in a mouse ear lymph microvessel 2 hours after injection.

The PA signals corresponding to the melanin particles were cleared over a two-hour period following the injection, as shown in FIG. 15.

Based on comparisons to similar data measured for melanoma cells labeled with markers that emitted strong PA signals, it was estimated that approximately 89% of the unlabeled melanoma cells were detected (data not shown). This percentage was lower than that found in previous in vitro studies (96%) and indicated a false-negative-signal rate of 1.5 cells/min because of the influence of background absorption by RBCs (data not shown). Longer-term monitoring of PA signals from ear blood vessels without prior melanoma cell injection detected no false-positive signals using as its criteria a signal-to-noise ratio $\geq 2$, where the signal noise was associated with fluctuations of laser energy and the density of red blood cells in the detected volume.

The results of this experiment demonstrated that two-color in vivo flow cytometry was an effective method of detecting metastatic melanoma cells in circulation. It was estimated that the method described above detected approximately 89% of the melanoma cells in circulation, with slightly lower detection rates due to skin pigmentation.

Example 17. Two-Wavelength In Vivo PAFC was Used to Detect Circulating Spontaneous Metastatic Cells During Tumor Progression An experiment was conducted to determine the ability of two-wavelength in vivo PAFC to detect relatively scarce endogenous metastatic melanoma cells circulating in lymph vessels. The PAFC system described in Example 10 was used to monitor endogenous metastatic melanoma cells in mice. Tumors were induced in nude mice by subcutaneous injections of melanoma cells using methods similar to those described in Example 7. Tumors formed and proliferated in the skin of the ear and the back of the nude mice over a period of 4 weeks, as previously described in Example 7.

Figure 16:
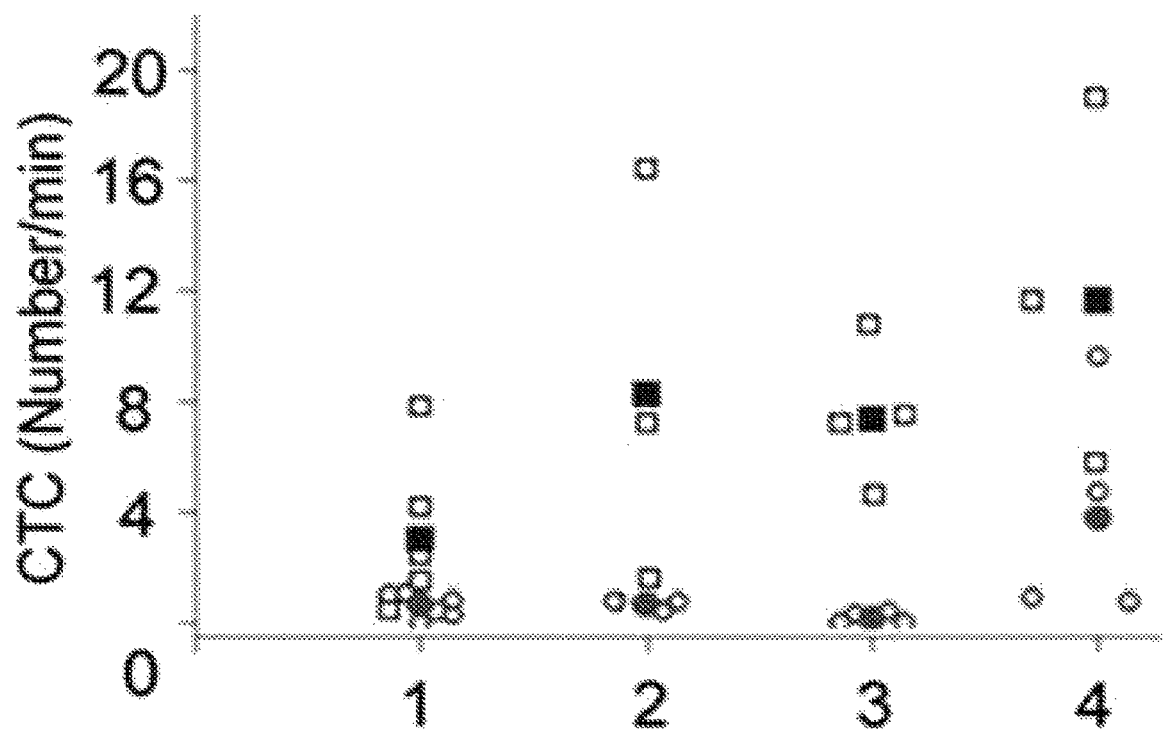
FIG. 16 is a summary of the PA signal rates from single melanoma cells detected in a mouse ear lymph microvessel 4 weeks after tumor inoculation.

PAFC was used to count spontaneous metastatic melanoma cells in a ~50 μm-diameter ear blood vessel and a 100-200-μm-diameter skin blood vessel during tumor progression in the ear and skin of a mouse, as summarized in FIG. 16. As previously described in Example 7, the skin tumor growth rate was faster than that of the ear tumors, and metastatic melanoma cells appeared more quickly in the circulation, as indicated by the mean cell detection rate measured in the skin capillaries, shown as solid square symbols in FIG. 16. In particular, within the first week after the induction of the tumors, about 1-4 melanoma cells/min were detected in the skin vasculature, and as the tumor size increased, the rate of detection of metastatic melanoma cells gradually increased to about 7 cells/min and about 12 cells/min after 3 weeks and 4 weeks, respectively.

The results of this experiment indicated that in vivo PAFC and PA mapping were sensitive methods with which to monitor the development of metastasized melanoma cells non-invasively, with high sensitivity and accuracy.

Example 18. PAFC System was Used to Determine Photoacoustic Response of Quantum Dot Markers In Vitro An experiment was conducted to determine the ability of two-wavelength in vivo PAFC to detect quantum dot cell markers in vitro. The PAFC system described in Example 2 was used to measure photoacoustic pulses emitted by quantum dots in response to laser pulses with wavelengths of 625 nm, pulse widths of 8 ns, and laser fluences ranging 0.001-10 J/m². The laser beam used to pulse the quantum dots had a diameter of about 20-30 μm in the sample plane. Quantum dots were obtained commercially with a polymer coating as well as with a streptavidin protein coating (Qdot 655 nanocrystals, Invitrogen, Carlsbad California). The quantum dots had diameters of about 15-20 nm and an emission wavelength of about 655 nm. Either single or aggregations of quantum dots were diluted with a buffer of 2% BSA/PBS and mounted in a layer of less than 1 μm on a microscope slide.

Figure 17:
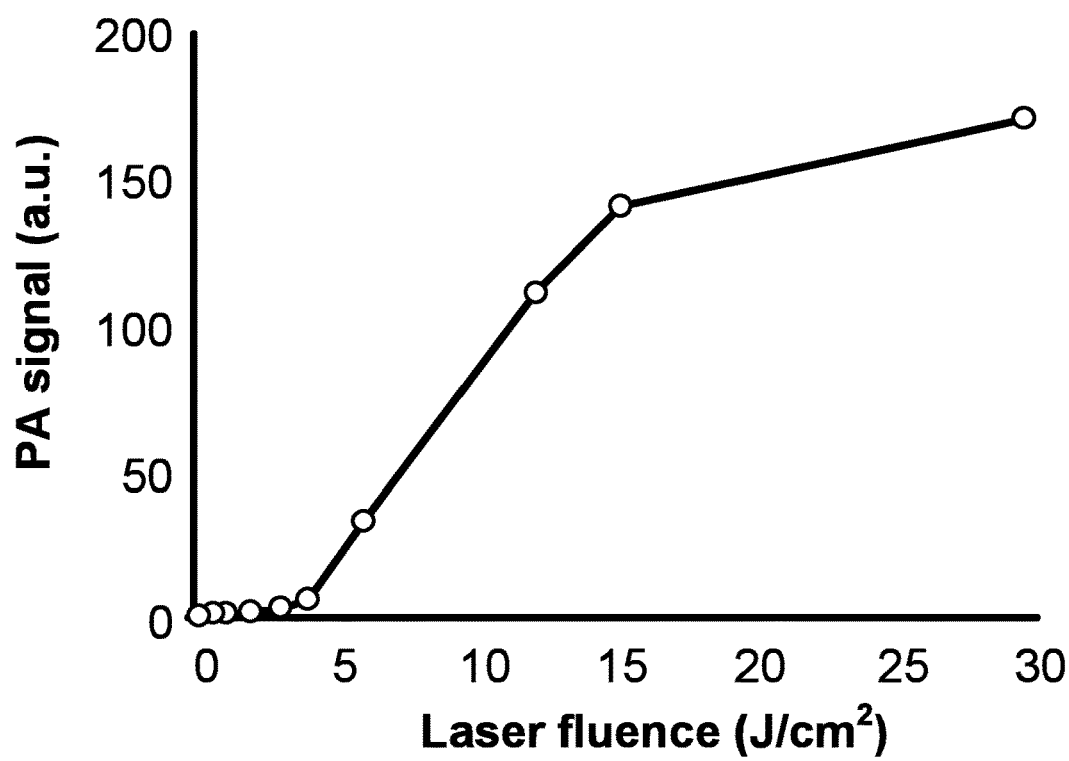
FIG. 17 is a summary of the PA signal amplitude generated by quantum dot markers as a function of laser fluence.

The PAFC system was used to pulse the quantum dot preparation with laser fluences ranging from 0.001-30 J/m². The magnitudes of the PA signals emitted by the quantum dots are summarized in FIG. 17. The PA signal response of the quantum dot preparations had a non-linear response to the variations in laser fluences. PA signal amplitude gradually increased in the laser fluence range from 0.1-1 J/cm². Through the laser fluence range between 1.5-7 J/cm², the response increased dramatically in a non-linear manner, and continued to increase in magnitude up to a laser fluence of 15 J/cm². At laser fluences above 15 J/m², the responses of the quantum dot preparations were saturated.

Figure 18:
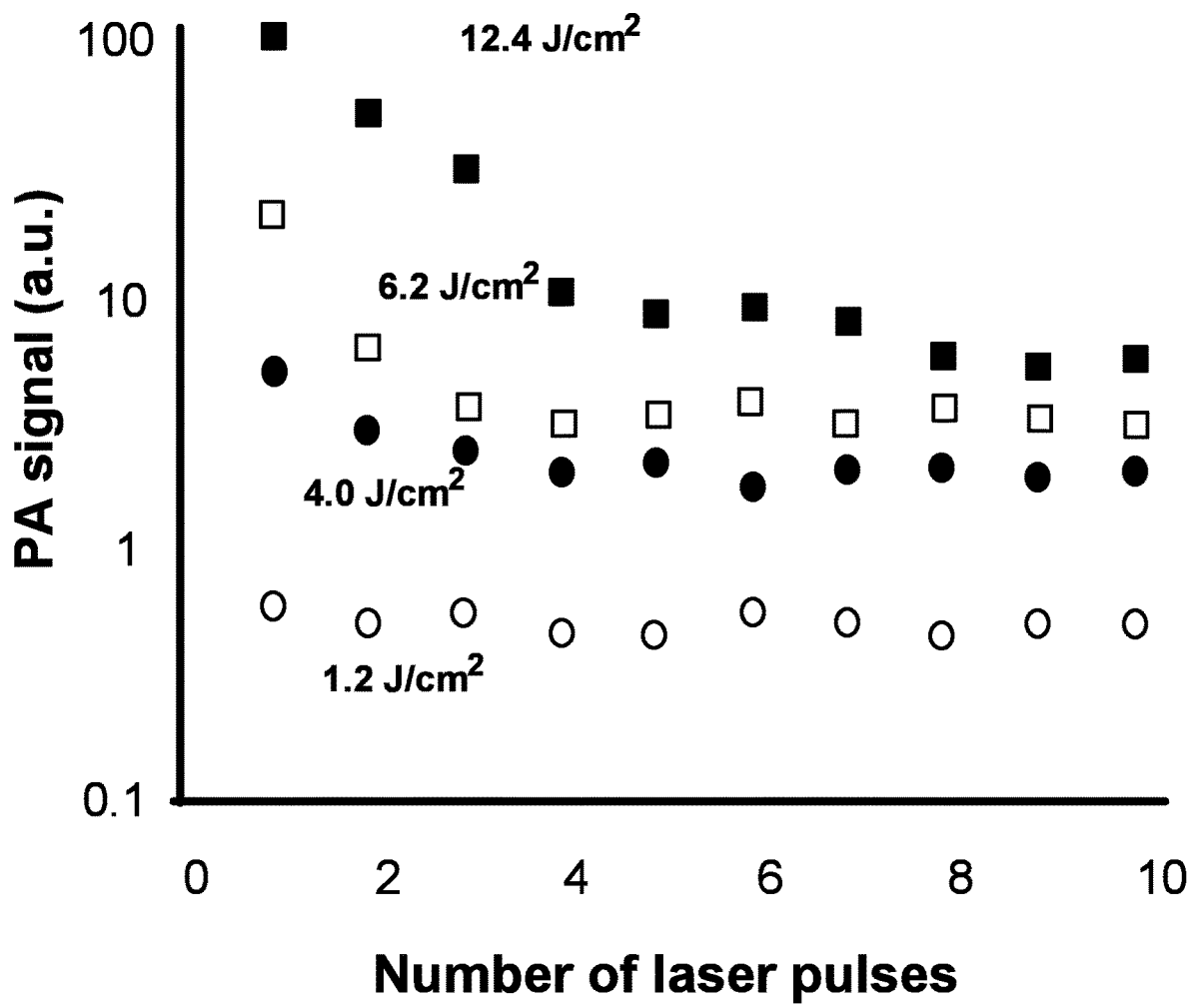
FIG. 18 is a summary of the PA signal amplitude generated by quantum dot markers as a function of the number of laser pulses.

The PA signal response as a function of the number of laser pulses for laser fluences of 1.2, 4.0, 6.2, and 12.4 J/cm² are summarized in FIG. 18. There was no sign of alteration of the laser pulse-induced PA signals at laser fluences below 3 J/cm², indicating no blinking behavior, unlike the stereotypical fluorescent blinking behavior observed in quantum dots. At higher laser fluences, significant decreases in the PA signal amplitude were observed with an increase in the number of pulses, possibly due to laser induced melting of thermal-based destruction by explosion of the quantum dots.

The results of this experiment indicated the quantum dots generated strong PA signals in response to laser pulses.

Example 19. PAFC System was Used to Detect Bacteria and Melanoma Cells Marked with Magnetic Nanoparticles In Vivo To demonstrate the application of magnetic nanoparticles as photoacoustic (PA) contrast agents, the following experiment was conducted.

*S. aureus* bacteria, described in Example 4, and melanoma cells, described in Example 6, were labeled with super paramagnetic iron oxide nanoparticles (Clementer Associates, Madison, CT). The nanoparticles consisted of a 50-nm core of magnetite ($Fe_3O_4$), coated with a 10-15 nm layer of Dextran and fluorescent dye. Both bacterial cells and melanoma cells were cultured at a density of approximately $10^6$ cells/mL, and magnetic nanoparticles were added to the cell cultures at a density of 0.5 mg/mL, and loaded into the cells by endocytosis for a minimum of 1 hour at 37° C. Labeled cells were centrifuged at 5,000 rpm for 3 minutes and the resulting pellets were resuspended in PBS.

The photoacoustic flow cytometry system (PAFC) system was similar in design to the PAFC system previously described in Example 2, with modifications to the laser, amplifier, and transducer components. A diode laser 905-FD1S3J08S (Frankfurt Laser Company) with driver (IL30C, Power Technology Inc., Little Rock, AR) was used to pulse the unbound magnetic nanoparticles and labeled cells with a pulse width of 15 ns, and a pulse repetition rate of 10 kHz. The laser beam dimensions used to pulse the nanoparticles and cells had an elliptical cross-section with minor and major axis dimensions of 11 μm and 75 μm, respectively, and a fluence energy maximum of 0.6 J/cm². The laser-induced PA signals were detected by a 5.5 mm-diameter, 3.5 MHz ultrasound transducer (model 6528101, Imasonic Inc., Besangon, France), amplified using a 2 MHz amplifier (Panametrics model 5660B) and recorded with a Boxcar data recorder (Stanford Research Systems, Inc.) and a Tektronix TDS 3032B oscilloscope.

To determine the clearance rate of unbound magnetic nanoparticles, the nude mouse ear model described in Example 2 was used. A 100-mL PBS suspension of the magnetic nanoparticles at a concentration of about $10^{11}$ nanoparticles/mL was injected into the vein tail of the mice.

Figure 19:
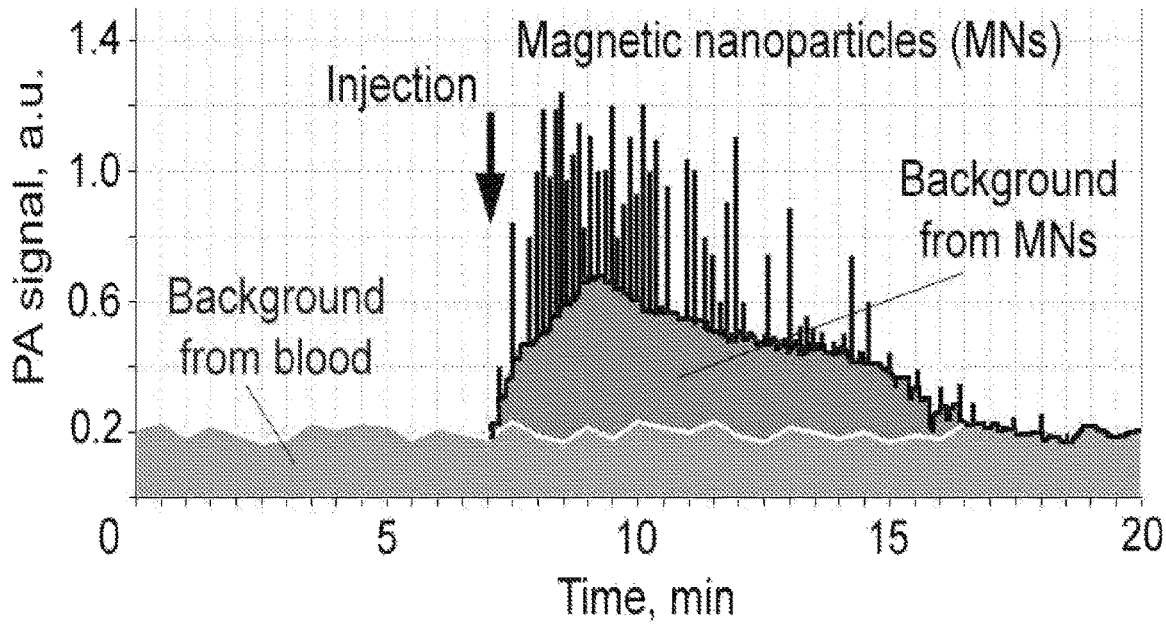
FIG. 19 is a summary of the PA signal amplitudes from a capillary over the 20 minutes following the injection of magnetic nanoparticles.

The magnetic nanoparticles were detected using the PAFC system described above. The laser pulses were delivered to the unbound magnetic nanoparticles at a wavelength of 639 nm and a laser fluence of 1.5 J/cm². The detection and subsequent clearance of the magnetic particles in the nude mouse ear model are summarized in FIG. 19. PA signals corresponding to the magnetic nanoparticles appeared within the first minute after injection. The PA signals were a combination of a fluctuating continuous PA background with superimposed large-amplitude PA signals. The magnitude of the background signal associated with the magnetic nanoparticles exceeded the PA background signals from the blood vessels by a factor of 2-3. The stronger but less frequent large-amplitude PA signals may be associated with random fluctuations of the number of magnetic nanoparticles in the detected volume and appearance of small aggregates of magnetic nanoparticles. The clearance time of the magnetic nanoparticles from the mouse ear microcirculation was in the range of 10-20 minutes.

Figure 20:
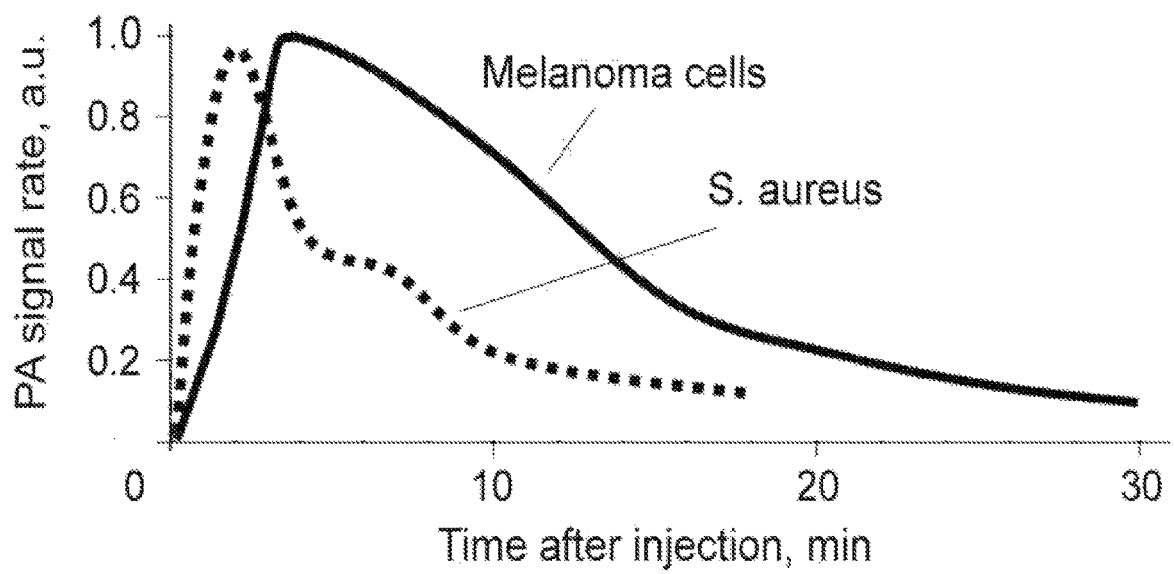
FIG. 20 is a summary of the PA signal rates from single melanoma cells and bacteria cells labeled with magnetic nanoparticles detected in a mouse ear capillary 30 minutes after injection.

Approximately $10^5$ B16F10 melanoma cells or *S. aureus* labeled with magnetic nanoparticles in 100 μL of saline solution were injected into a mouse tail vein and then monitored in the mouse ear using the PAFC system described above. Labeled melanoma cells were detected using a 905 nm, 0.4 J/cm² laser pulse, and the bacterial cells were detected using an 850 nm, 0.9 J/cm² laser pulse. The resulting PA signals emitted by *S. aureus* and melanoma cells labeled with magnetic nanoparticles are summarized in FIG. 20. Numerous PA signals from individual circulating cells were detected, with a maximum rate of detection within the first 1-3 minutes. The average half-life of the labeled bacteria and cancer cells in the blood microcirculation was 4.5 and 12 min, respectively.

Figure 21:
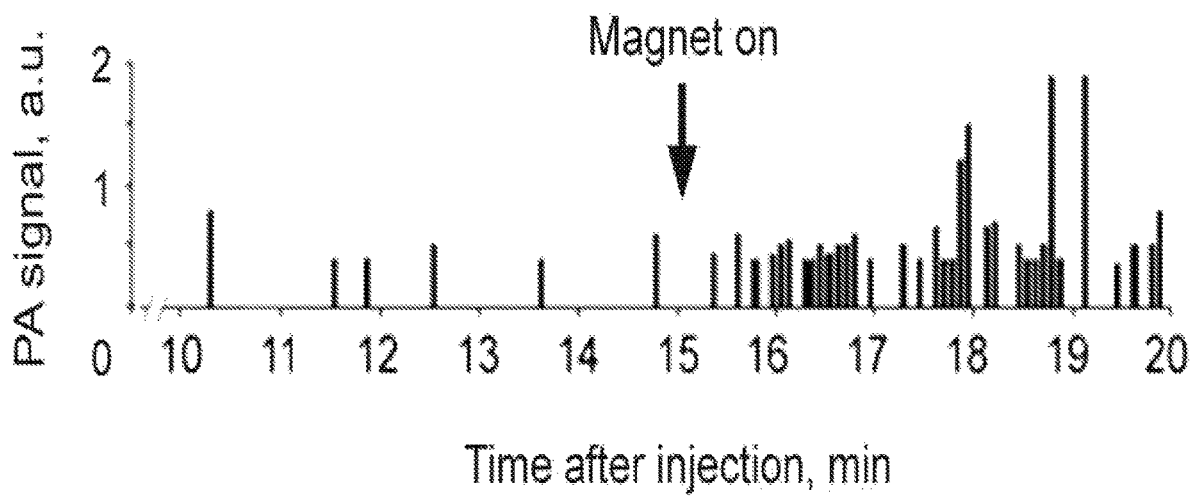
FIG. 21 is a summary of the PA signal rates from melanoma cells labeled with magnetic nanoparticles before and after the application of a magnetic field, detected in a mouse ear capillary 20 minutes after injection.
Figure 22:
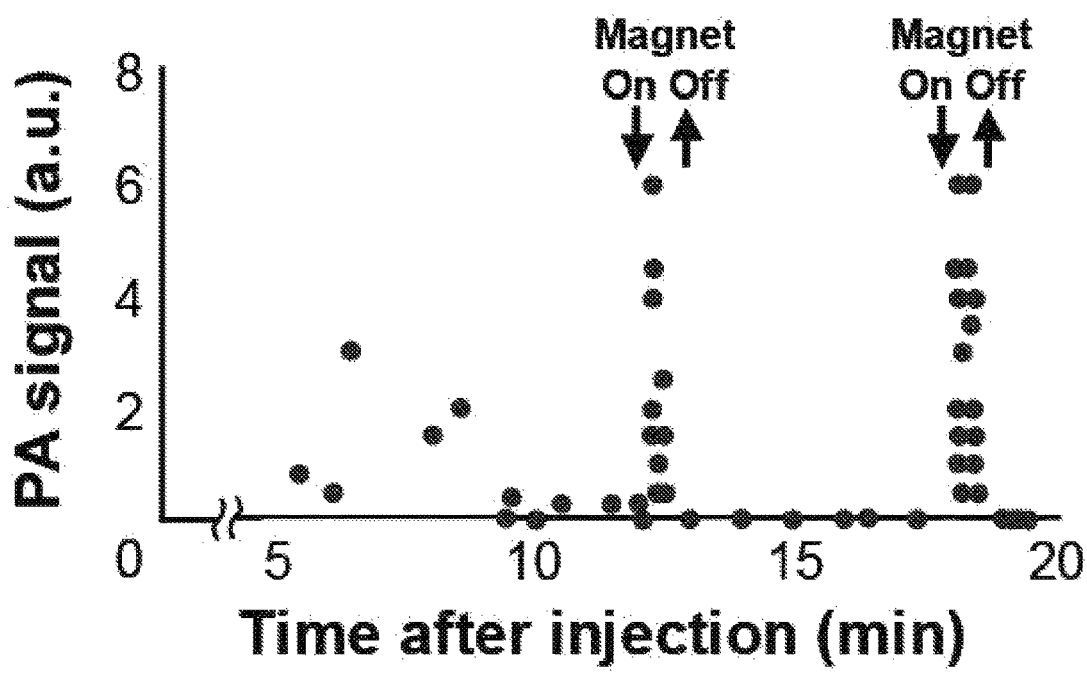
FIG. 22 is a summary of the PA signal rates from bacterial cells labeled with magnetic nanoparticles before and after the application of a magnetic field, detected in a mouse ear capillary 20 minutes after injection.

After the labeled melanoma cells and bacteria were essentially cleared from the circulation and only rare PA signals were detected, a local permanent magnetic field was imposed through intermediate tissue to the blood microvessels. The local permanent magnetic field was provided by a cylindrical Neodymium-Iron-Boron (NdFeB) magnet with Ni—Cu—Ni coating that was 3.2 mm in diameter and 9.5 mm long with a surface field strength of 0.39 Tesla (MAGCRAFT, Vienna, VA). The distance between the magnet and the microvessel walls ranged between 50-100 μm. As shown in FIGS. 21 and 22, the application of the magnetic field to the blood microvessels led to an immediate increase in both PA signal amplitudes and rate of detection in the vicinity of the magnet for the labeled melanoma cells and bacterial cells respectively.

The results of this experiment demonstrated that magnetic nanoparticles could be used to label circulating melanoma and bacteria cells for use in the prototype PAFC system. Further, a magnetic field applied to the blood microvessel in which the PAFC detected circulating cells was able to locally enrich the concentration of cells to be detected.

Example 20. Magnet-Induced Amplification of Signals from CD44+ Cells Targeted by Magnetic Nanoparticles To assess the viability of manipulating cells labeled with magnetic nanoparticles (MNPs) using an external magnetic field, the following experiments were conducted.

Human breast cancer cells (MDA-MB-231, American Type Culture Collection, Manassas, VA) were cultured according to the vendor's specifications. The cells were cultured to confluency in vitro, detached with 0.25% trypsin-0.53 mM EDTA, washed and resuspended in PBS. The resuspended cells were then incubated for one hour at 37° C. with 30 nm spherical magnetic nanoparticles (Ocean NanoTech, Springdale, AR) conjugated with antibodies targeted to human CD44 receptor (MNP-CD44). In addition, the antibodies were stained with fluorescent labels (fluorescein isothiocyanate-Dextran [FITD], BD Pharmaceuticals) according to the manufacturer's specification prior to conjugation to the MNPs. The concentration of MNP-CD44 particles added to the PBS was about $0.1 \times 10^3$-$1 \times 10^3$ particles per suspended cell. The labeled cells were resuspended in PBS, placed in 8.6 ml wells (Molecular Probes) and covered with a top cover. In this example, the cells were triple labeled, since the MNP portion of the MNP-CD44 particle functions as a photoacoustic and photothermal contrast agent, and the FITD staining of the antibody functions as a fluorescent label.

A permanent magnetic field was provided by a magnet tip gently attached to the top cover of the slides for the manipulation of the labeled cells. The magnet was a cylindrical neodymium-iron-boron (NdFeB) magnet with Ni—Cu—Ni coating (MAGCRAFT, Vienna, VA). This cylindrical magnet had a diameter of 3.2 mm, a length of 9.5 mm, and a surface field strength of 0.39 Tesla.

Figure 23A:
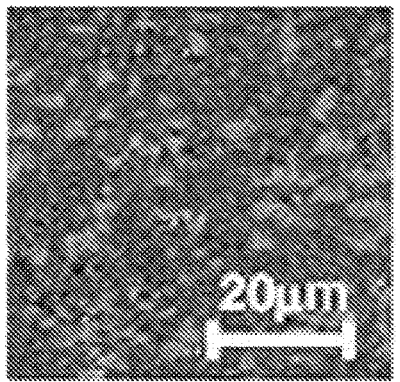
FIG. 23A-FIG. 23B includes fluorescent microscopic images of a suspension of magnetic nanoparticles conjugated with targeted antibodies.
Figure 23B:
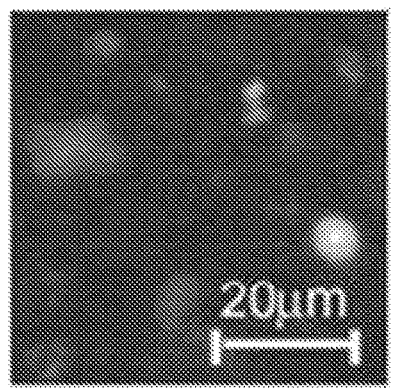

To assess the effectiveness of the magnet at attracting and clustering the MNP-CD44 particles, the magnetic tip was attached the top cover of a slide containing suspended MNP-CD44 particles only in PBS at a concentration of $10^{11}$ particles/mL. The attachment of the magnet tip to the top cover of the slide induced the migration of the MNPs to the immediate vicinity of the magnet, resulting in a dark spot visible with the naked eye. The identity of the MNP-CD44 particles within the dark spot was verified by fluorescent microscopy. FIG. 23 shows the fluorescent image of the slide before (FIG. 23A) and after (FIG. 23B) the application of the magnetic field to the top cover; the clustered MNP-CD44 particles appear as a bright spot in the lower right corner of FIG. 23B.

Figure 24A:
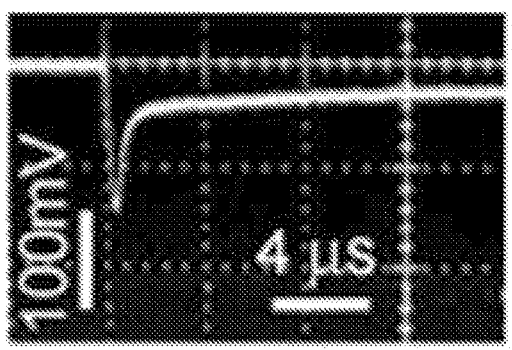
FIG. 24A-FIG. 24B includes non-linear photothermal (PT) signals obtained from a suspension of magnetic nanoparticles conjugated with targeted antibodies.
Figure 24B:
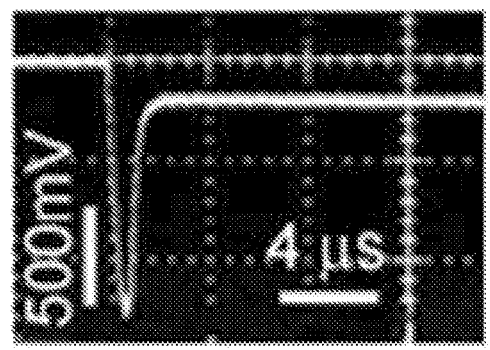

Non-linear photothermal (PT) signals were obtained for the same slide before and after the application of the magnetic field, as shown in FIG. 24. The laser used in this experiment had a wavelength of 639 nm, a beam diameter of 15 μm, and a fluence of 50 mJ/cm². The PT signal from the region with a high local concentration of MNP-CD44 particles after the application of the magnetic field (FIG. 24B) was 10-20-fold higher than the PT signal obtained prior to the applied magnetic field (FIG. 24A).

Figure 25A:
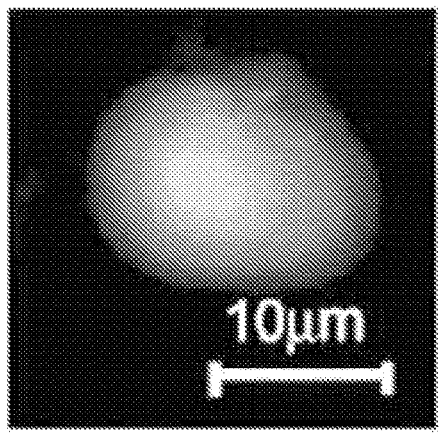
FIG. 25A-FIG. 25B includes fluorescent microscopic images of a single cancer cell labeled using magnetic nanoparticles conjugated with targeted antibodies.
Figure 25B:
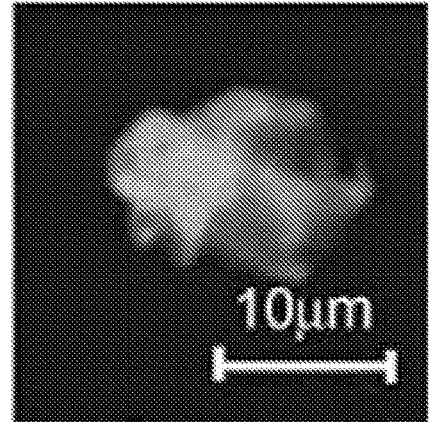
Figure 26A:
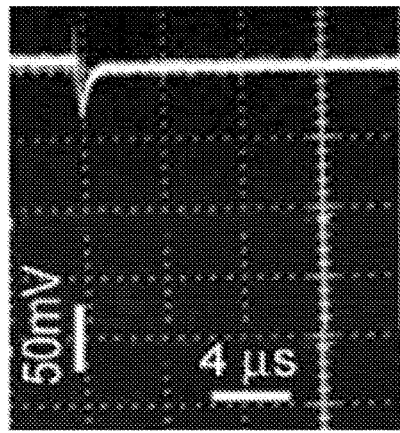
FIG. 26A-FIG. 26B includes non-linear photothermal (PT) signals obtained from a single cancer cell labeled using magnetic nanoparticles conjugated with targeted antibodies.
Figure 26B:
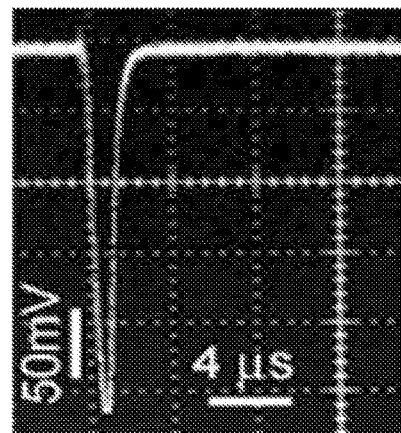

Single cancer cells labeled with MNP-CD44 as described above were similarly assessed before and after exposure to the external magnetic field. As shown in FIG. 25, the application of the external magnetic field induced an enhancement of the local fluorescence gradient within the single isolated cell (FIG. 25B) compared to the relatively homogenous spatial fluorescent light distribution prior to exposure to the external magnetic field (FIG. 25A), suggesting magnetic field-induced clustering of the MNPs within the single cell. Further, as shown in FIG. 26, exposure of the isolated labeled cells to the external magnetic field resulted in a 6.6-fold enhancement of the PT signals obtained from these cells (FIG. 26B) relative to the PT signals obtained from the cells before exposure to the magnetic field (FIG. 26A). The appearance of locally dense intracellular clusters of MNPs is likely due to the accumulation of the MNPs under the magnet near cellular structures such as cell membrane that may have acted as mechanical obstacles to impede the further movement of the MNPs.

The results of this experiment indicated that the labeling of cells using MNPs conjugated with antibodies or other biological compounds targeted toward particular cell types renders the cells amenable to manipulation using magnetic fields. Further, the external magnetic field induces the formation of intracellular clusters of MNPs, resulting in the enhancement of PT signals of the labeled cells.

Example 21. Efficacy of Conjugated Nanoparticles Targeted to Circulating Tumor Cells To assess the efficacy of the binding of nanoparticles conjugated with target compounds directed to receptors specific to circulating tumor cells, the following experiments were conducted. A magnetic nanoparticle (MNP) and a gold nanotube (GNT) were conjugated to known ligands of cancer cell-specific receptors and assessed to determine the contrast of the PA signals produced relative to other blood components, the efficiency of binding to circulating cancer cells, the ability to capture labeled CTCs and circulating MNPs using an external magnetic field, the clearance dynamics of the nanoparticles in vivo, and the clearance dynamics of CTCs labeled using the nanoparticles.

Because human tumor cells are typically heterogeneous, multiplex targeting and a multicolor detection strategy was utilized to increase the specificity of the nanoparticles needed to implement the in vivo identification of circulating tumor cells (CTCs). To this end, the CTCs were labeled with two different labeling particles (magnetic nanoparticles and golden carbon nanotubes), which emitted photoacoustic (PA) signals distinguishable from background PA signals from surrounding blood cells and endothelial tissues. The PA detection of the CTCs labeled using the MNPs and CTCs was conducted by exposing the CTCs to laser pulses at two different wavelengths to enhance the contrast of the PA signal produced by each type of labeling particle.

Figure 27:
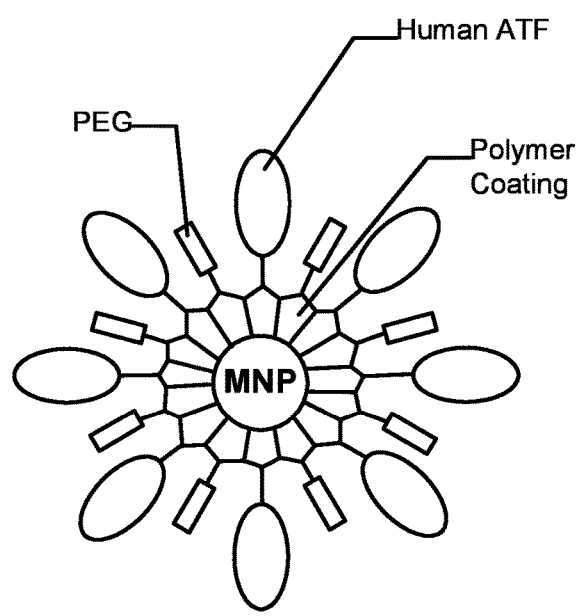
FIG. 27 is a schematic illustration of a conjugated magnetic nanoparticle.

Using methods similar to those described in Example 20, magnetic nanoparticles (MNPs) were conjugated to an amino-terminal fragment (ATF) of the human urokinase plasminogen activator, which serves as specific ligand for the urokinase plasminogen activator receptors that are highly expressed on many types of cancer cells but are expressed at a low level in normal blood and endothelial cells. These conjugated MNPs (MNP-ATFs), illustrated schematically in FIG. 27, served as dual magnetic and photoacoustic contrast agents due to the intrinsic absorption properties of the $Fe_2O_3$ core of the MNPs. In addition, the MNP-ATFs were further conjugated with fluorescein (FITC) to provide additional fluorescence imaging capability in a manner similar to Example 20.

Figure 28:
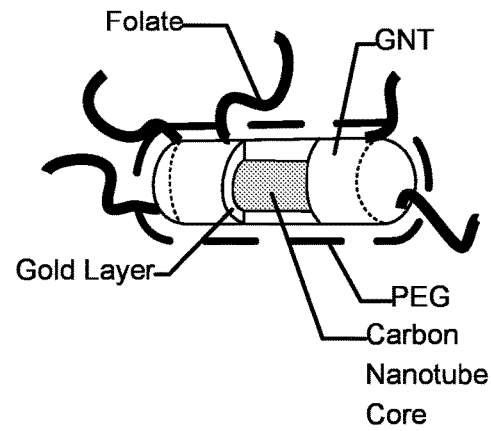
FIG. 28 is a schematic illustration of a conjugated gold nanotube.

The golden carbon nanotubes (GNTs) were conjugated to folate, which serves as a ligand for the folate receptors that are expressed in cancer cells but absent in normal blood. The GNTs selected had average lengths of about 98 nm and average diameters of about 12 nm. The folate was conjugated to the GNTs using electrostatic interactions. The resulting folate-GNT conjugates were washed three times in the presence of 1% polyethylene glycol (PEG) and conjugated with fluorescein (FITC) to provide additional fluorescence imaging capability. These folate-conjugated golden carbon nanotubes (GNT-FOLs) are illustrated schematically in FIG. 28.

Figure 29:
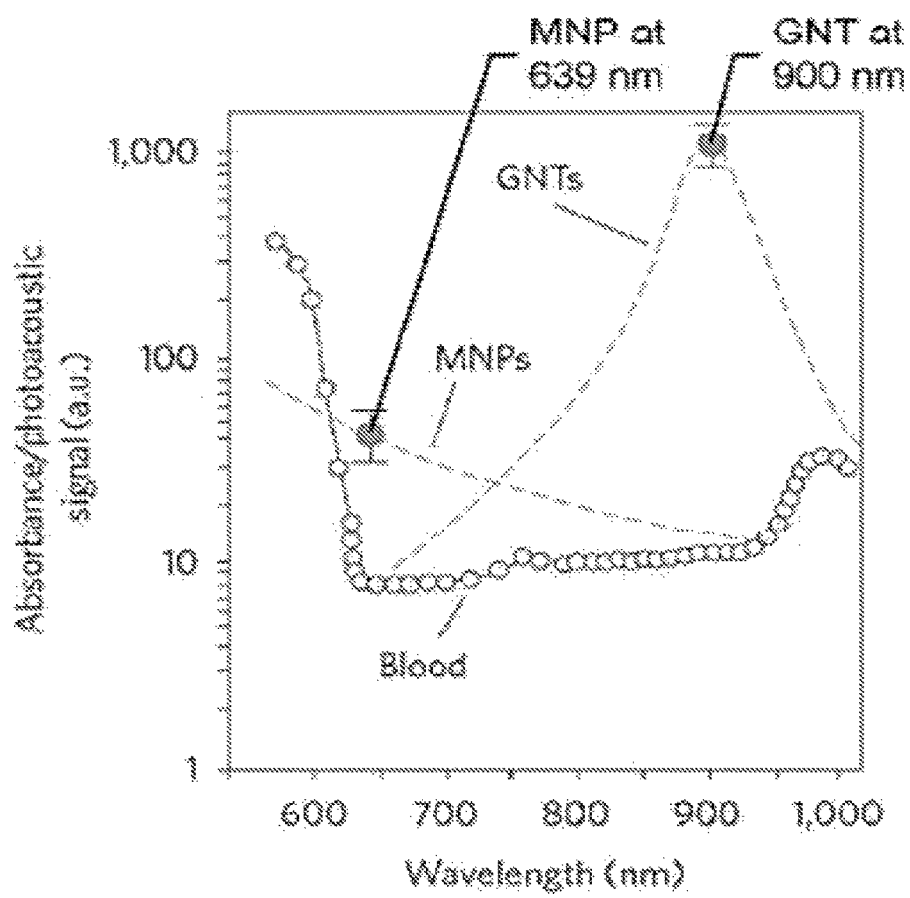
FIG. 29 are estimated photoacoustic spectra showing the PA signals of a magnetic nanoparticle, a gold nanotube, and blood background signals as a function of laser pulse wavelength.

Two laser wavelengths were selected to perform the photoacoustic sensing of the dually-labeled tumor cells. The first wavelength was selected to be 639 nm to provide strong photoacoustic contrast of the PA signal from the MNPs, and the second wavelength of 900 nm was selected to enhance the contrast of the PA signal of the GNTs relative to other blood components. An estimated photoacoustic spectra showing the PA signals of the MNPs, the GNTs, and the blood background signals are shown in FIG. 29, along with the two wavelengths selected for PA sensing.

Figure 30A:
FIG. 30A-FIG. 30B includes microscope images of a single cancer cell incubated with unconjugated magnetic nanoparticles (FIG. 30A) and of a single cancer cell incubated with conjugated magnetic nanoparticles (FIG. 30B).
Figure 30B:
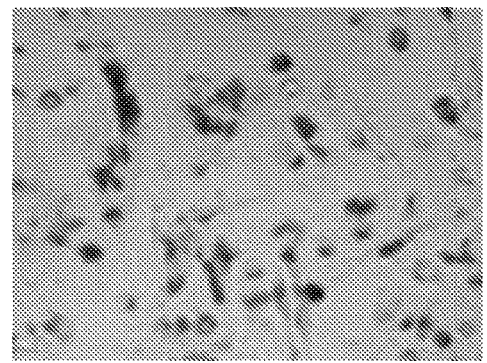
Figure 31A:
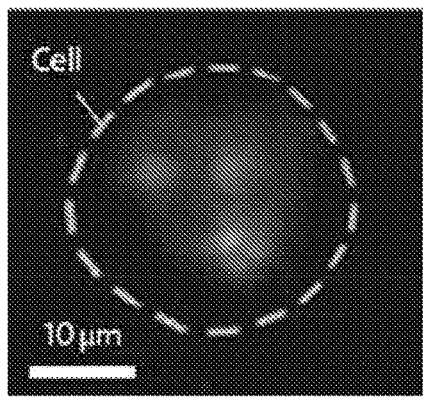
FIG. 31A-FIG. 31B contains fluorescent microscope images of a single cancer cell incubated with fluorescein-stained unconjugated gold nanotubes (FIG. 31A) and a single cancer cell incubated with fluorescein-stained, folate-conjugated gold nanotubes (FIG. 31B).
Figure 31B:
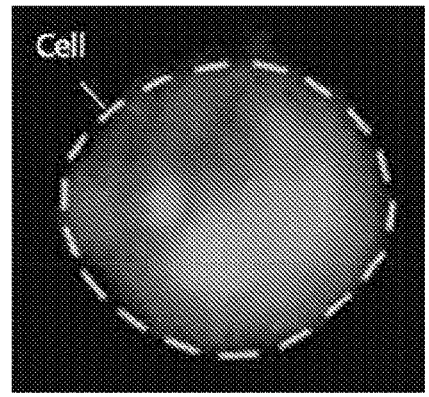

The human breast cancer cell line MDA-MB-231, which is positive for both the urokinase plasminogen activator and the folate receptor, were used in these experiments. To verify the target specificity of the conjugated MNP nanoparticles in vitro, the cancer cells were incubated with unconjugated MNP and with conjugated MNP-ATF nanoparticles for two hours at 37° C. After incubation, the cells were subjected to Prussian Blue staining, which stained the iron cores of any MNPs attached to the cells. FIG. 30 includes microscope images of a single cancer cell incubated with unconjugated MNPs (FIG. 30A) and with MNP-ATF (FIG. 30B). To verify the target specificity of the conjugated GNTs in vitro, the cancer cells were incubated with GNTs conjugated with fluorescein only or with the conjugated GNT-FOL nanoparticles for two hours at 37° C. Fluorescent images of a single cell incubated with the fluorescein-conjugated GNTs (FIG. 31A) and a single cell incubated with the GNT-FOL (FIG. 31IB) indicated that the GNT-FOL attached specifically to the cancer cells.

Figure 32:
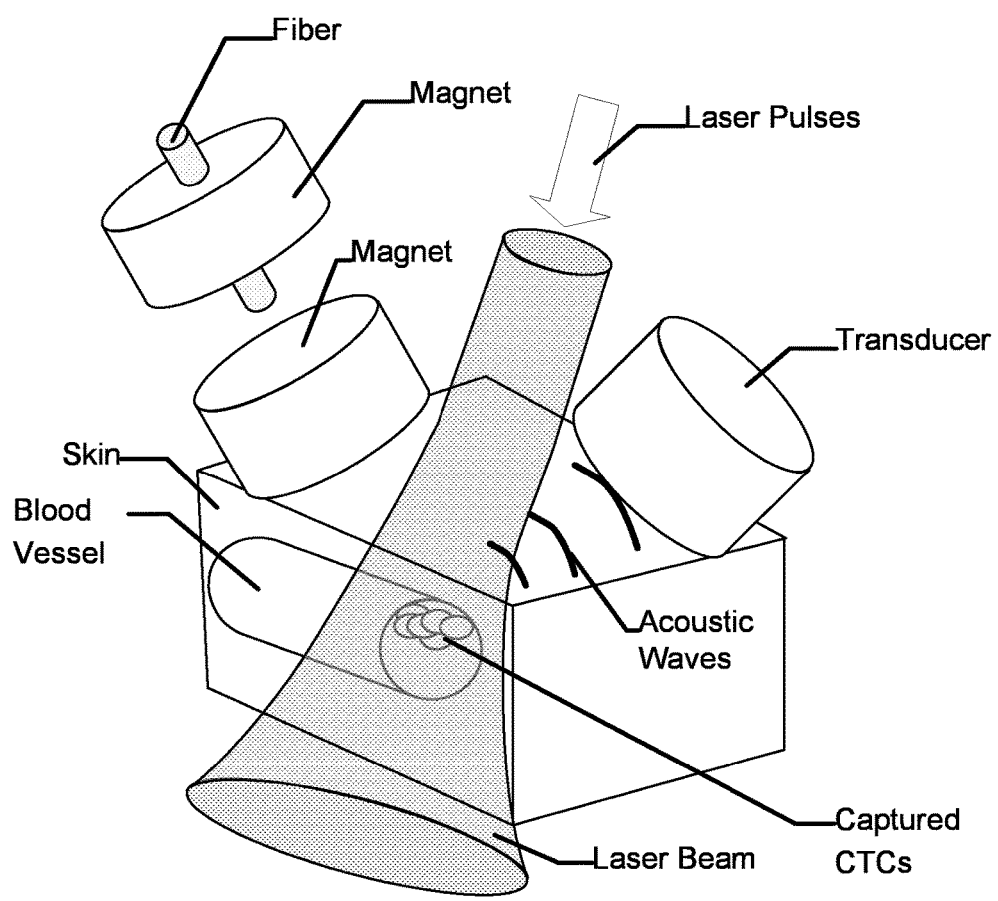
FIG. 32 is a schematic illustration of a PAFC system modified to provide the capability to attach a magnet near the area of interest of the PAFC system.

A PAFC system similar to that described in Example 10 was used with the following modifications, illustrated in FIG. 32. A diode laser (905-FD1S3J08S, Frankfurt Laser Company) and associated driver (IL30C, Power Technology) was used to deliver laser pulses at a wavelength of 905 nm, a pulse width of 15 ns and a pulse repetition rate of 10 kHz. In addition, a second co-linear probe pulse from a Raman shifter was delivered at a wavelength of 639 nm, a pulse duration of 12 ns and at a 10-ms delay relative to the 905 nm pump pulse. The delivery of laser radiation to the area of interest was performed either with microscope optics or using a 330-mm fiber with focusing tip.

The laser-induced photoacoustic waves were detected using 3.5 MHz ultrasound transducers having a diameter of 4.5 mm (model 6528101, Imasonic). The transducer was gently attached to the external surface of the sample containing the labeled cells or nanoparticles to be detected and warmed water or ultrasound gel was topically applied to the surface to enhance the acoustic matching between the transducer and the samples. The detected signal was amplified using a 2 MHz, 60 dB gain amplifier (model 5660B, Panametrics), and the amplified signal was digitized, recorded, and analyzed as described in Example 2.

Also shown in FIG. 32 is a magnet similar to the magnet described in Example 20 that was used to apply an external magnetic field to the area of interest. In selected experiments, a similar magnet was used that incorporated a custom-made 0.7-mm hole through which the 330-mm fiber was threaded to deliver the laser radiation. The magnet was gently attached to the surface of the sample containing the nanoparticles or labeled cells to be detected. In those cases in which the sample was a live mouse, the distances between the magnet and examined vessels ranged from 50 to 100 mm (mouse ear) or 0.3 to 0.5 mm (abdominal area).

Figure 33:
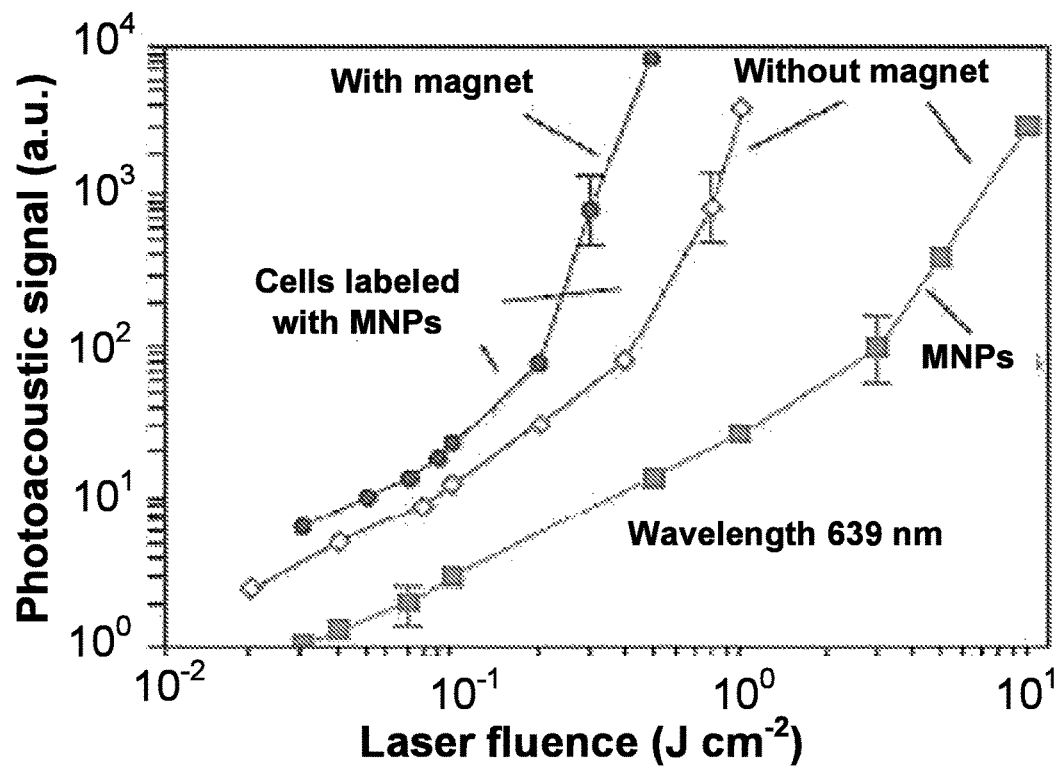
FIG. 33 is a summary of the PA signal rates produced by three different samples at a range of laser fluences: a suspension of magnetic nanoparticles, a suspension of cells labeled with magnetic nanoparticles, and a suspension of cells labeled with magnetic nanoparticles in an external magnetic field.

Samples containing suspensions of either $10^{11}$ MNPs/ml of 10-nm MNPs in PBS, or a single MDA-MB-231 cell labeled with the MNPs as described above were placed onto 120-mm-thick microscope slides. The PAFC system detected PA signals generated using laser fluences ranging from about $10^{-2}$ to about $10^1$ J/cm$^2$, either in the presence or absence of an external magnetic field that was applied for 10 minutes prior to PA detection. As shown in FIG. 33, the PA signals from the MNP-labeled cells were significantly higher than the PA signals from unbound MNPs, particularly at the higher laser fluences and after exposure to the magnetic field for 10 min. This signal amplification may be due to magnet-induced MNP clustering within the labeled cells and laser-induced microbubbles around the MNP clusters.

Figure 34:
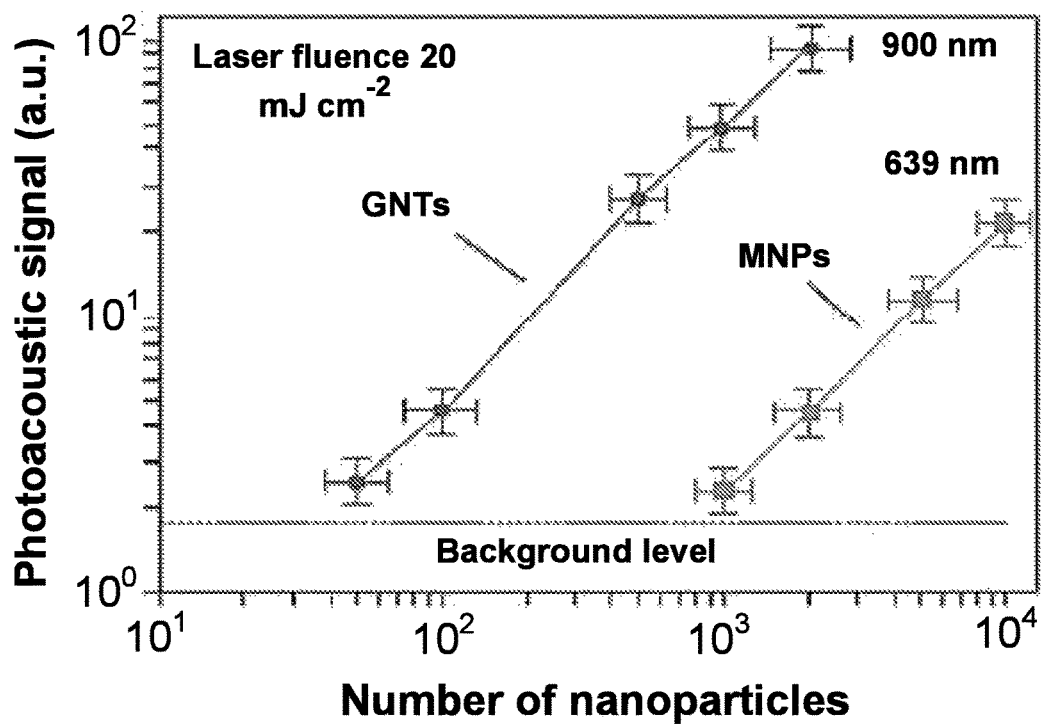
FIG. 34 is a summary of the PA signal rates from samples of gold nanotubes and magnetic nanoparticles spiked into mouse blood at a range of nanoparticle concentrations.

MNPs and GNPs were spiked into mouse blood samples at a range of concentrations and PA signals of the spiked samples were obtained using laser pulses at a laser fluence of 20 mJ/cm$^2$ and pulse wavelengths of 639 nm and 900 nm for the MNP and GNP samples, respectively. The photoacoustic signals measured for the two sample types are summarized in FIG. 34; the lowest detectable concentrations of nanoparticles above the background PA signals from other blood components were determined to be 35 GNTs and 720 MNPs.

Labeling efficiency of the MDA-MB-231 cells using different combinations of unconjugated and conjugated nanoparticles was assessed using the PAFC system on static cell cultures. The samples to be labeled included MDA-MB-231 cells suspended in PBS, MDA-MB-231 cells spiked into mouse blood, and unspiked mouse blood with no added MDA-MB-231 cells. The labeling particles added to the samples included: 1) unconjugated MNPs, 2) unconjugated GNTs, 3) a 20:80 ratio mixture of GNTs and MNPs, 4) conjugated MNP-ATF particles, 5) conjugated GNT-FOL particles, and 6) a 20:80 ratio mixture of GNT-FOL and MNP-ATF particles. The samples were treated with the labeling particles for one hour at 37° C. Table 3 summarizes the labeling efficiencies obtained using the PAFC system. The conjugated nanoparticle mixture cocktail showed the best targeting efficiency (96±2.1%) for the cells on mouse blood under static conditions.

TABLE 3

Labeling Efficiency of Unconjugated vs. Conjugated Nanoparticles

| Nanoparticles | Labeling Efficiency (%) | | |
|---|---|---|---|
| | Cells in PBS | Cells in Mouse Blood | Normal Mouse Blood (control) |
| MNP | 5 | 3 | 5 |
| GNT | 15 | 8 | 4 |
| MNP + GNT | 18 | 11 | 8 |
| MNP-ATF | 85 | 71 | 98 |
| GNT-FOL | 89 | 76 | 96 |
| MNP-AFT + GNT-FOL | 98 | 96 | 9 |

Figure 35:
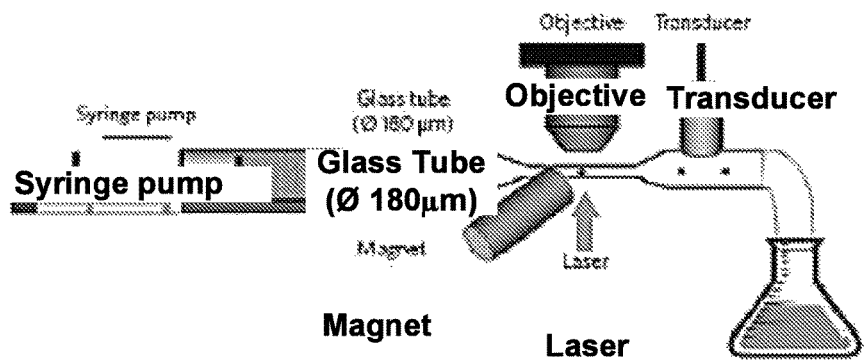
FIG. 35 is a schematic illustration of a PAFC flow simulation system.
Figure 36A:
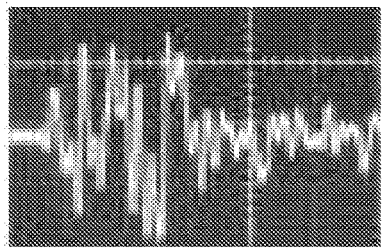
FIG. 36A-FIG. 36B includes non-linear photothermal (PT) signals obtained from labeled cancer cells (FIG. 36A) and from the surrounding suspension medium (FIG. 36B) using a PAFC flow simulation system.
Figure 36B:
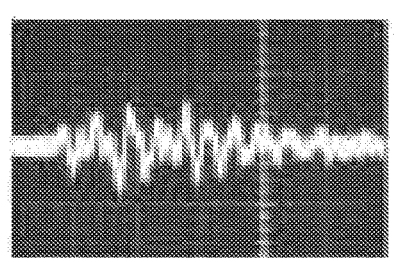
Figure 37A:
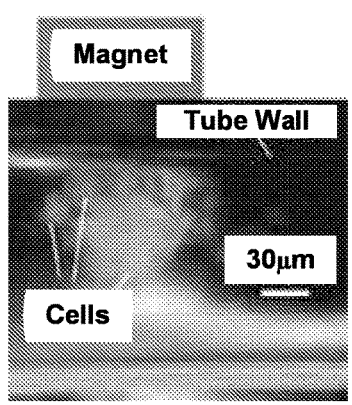
FIG. 37A-FIG. 37C includes fluorescent microscopic images of cancer cells labeled with conjugated magnetic nanoparticles in the vicinity of a magnet showing the labeled cancer cells suspended in PBS at a flow velocity of 0.5 cm/s (FIG. 37A), the labeled cancer cells with additional conjugated magnetic nanoparticles at flow velocities of 0.1 cm/s (FIG. 37B) and 5 cm/s (FIG. 37C).
Figure 37B:
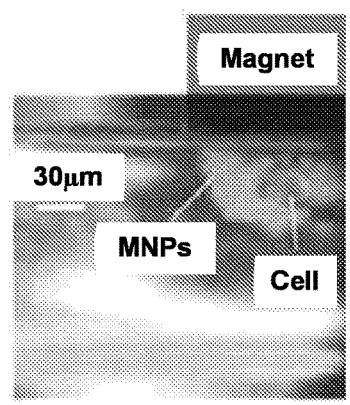
Figure 37C:
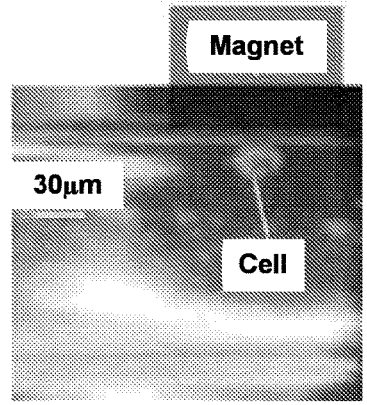

To assess the ability to capture cancer cells labeled with MNP-AFT particles using a magnetic field, a PAFC flow simulation system, shown in FIG. 35 was used visualize the capture of the labeled cancer cells and to measure PA signals generated by labeled cancer cells at different flow velocities ranging from 0.1-10 cm/s. The PAFC flow simulation system included a syringe pump attached to a 180 μm diameter glass tube. The glass tube directed the flow of the sample exiting the syringe pump past a magnet and laser and into a flask. A microscope objective and an ultrasound transducer were also attached to the glass tube in close proximity to the magnet and laser to obtain microscopic images and PA signals, respectively. Labeled cancer cells were suspended in PBS either with or without additional MNP-AFT particles and observed as they flowed through the glass tube at a range of flow velocities. The PA signals produced by the labeled cancer cells and the surrounding suspension medium are shown in FIGS. 36A and 36B, respectively. FIG. 37 is a series of fluorescent microscopic images taken in the vicinity of the magnet of labeled cancer cells in PBS at a flow velocity of 0.5 cm/s (FIG. 37A), for labeled cancer cells with additional MNP-AFT particles at flow velocities of 0.1 cm/s (FIG. 37B) and 5 cm/s (FIG. 37C).

Figure 38:
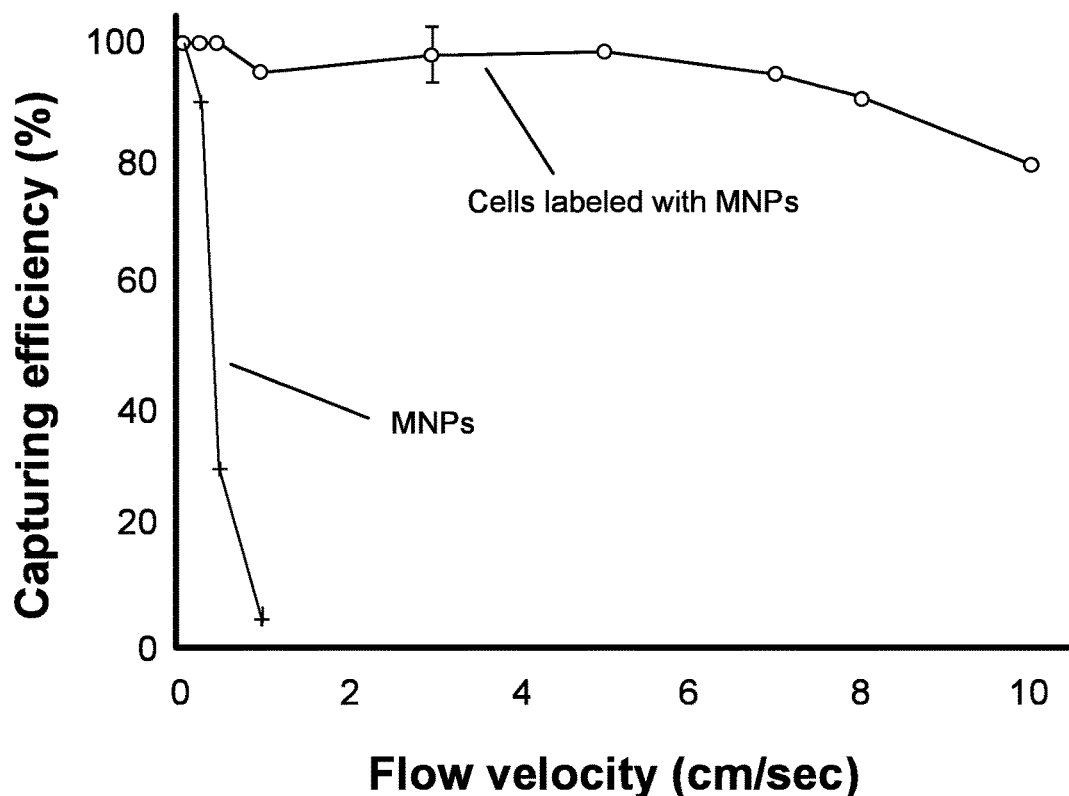
FIG. 38 is a summary of the capture efficiency (the number of cells or particles captured at a flow velocity as a percentage of the number of cells or particles captured at 0.1 cm/s.

The attached magnet of the PAFC flow simulation system captured the MNP-labeled cancer cells at a broad range of flow velocities (0.1-10 cm/s), accompanied by strong PA signals from the area under the magnet is excess of those signals outside the magnet corresponding to rare uncaptured cells and unbound MNPs. Both the additional MNPs and the MNP-labeled cells were captured at a flow velocity of 0.1 cm/s, as shown in FIG. 37B. However, increasing the flow velocity to 5 cm/s removed most of the free MNPs but the MNP-labeled cell remained captured, as shown in FIG. 37C. FIG. 38 summarizes the capture efficiency of the labeled cells and the MNPs, defined as the relative number of cells or MNPs captured at different flow velocities as a percentage of the corresponding number captured at a flow velocity of 0.1 cm/s. The capture efficiency of the unbound MNPs falls off rapidly as flow velocity increases above 0.1 cm/s, while the capture efficiency is maintained at a level of at least 90% for all but the highest flow velocities. Because magnetic force is proportional to the density of magnetic material within a particular volume, the randomly distributed free MNPs were more likely to be removed from the magnetic field by flow drag forces than the labeled cancer cells that contained a higher local MNP concentration or dense MNP clusters.

Figure 39:
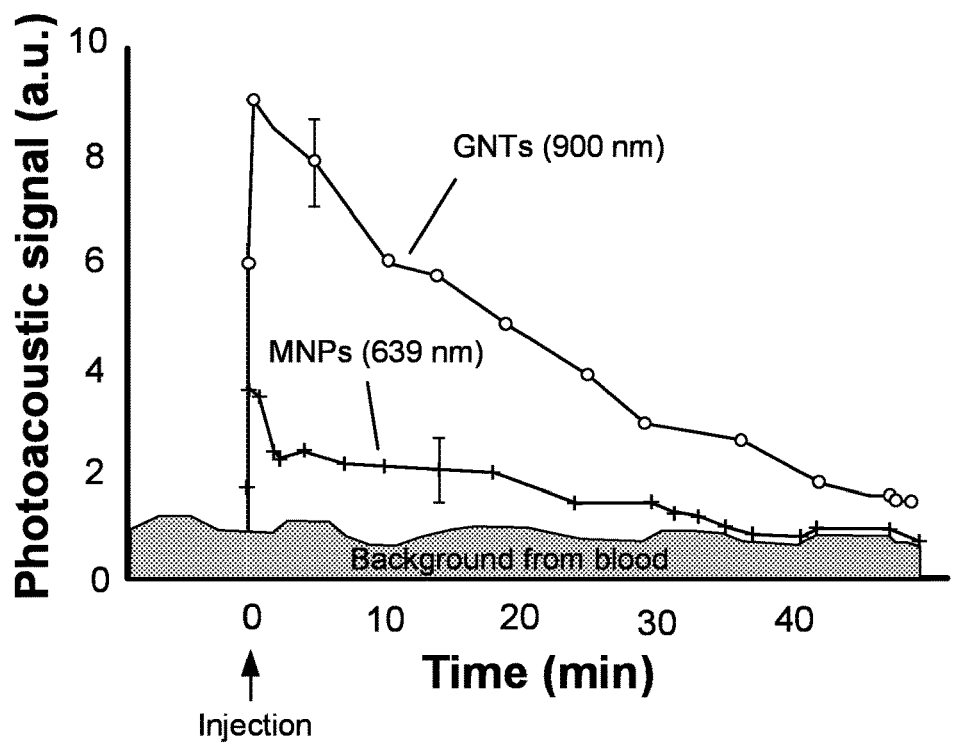
FIG. 39 is a summary of the PA signal rates produced by circulating gold nanotubes and magnetic nanoparticles in a mouse ear vein after an initial injection of the nanoparticles into the tail vein of the mouse.

To determine the depletion kinetics of the nanoparticles in vivo, MNPs and GNTs were separately injected through mouse tail vein of nude mice (nu/nu) and the circulation of the nanoparticles was monitored using the mouse ear model described in Example 2. The nanoparticles were injected in two separate samples consisting of MNPs in 10 mL of PBS at a concentration of $10^9$ nanoparticles/mL, and GNTs in 10 mL of PBS at a concentration of $10^{11}$ nanoparticles/mL. Photoacoustic monitoring of vessels in the mouse ear was conducted using laser pulses at 639 and 900 nm to detect concentration of the circulating nanoparticles. As summarized in FIG. 39, the half-life of both nanoparticles in circulation was about 15-20 minutes. At later times, rare flashes of PA signals appeared, preferentially from the MNPs, which were likely associated with random fluctuation of nanoparticle numbers in the detected volume and the non-specific uptake of the nanoparticles by circulating blood cells such as macrophages. No photoacoustic signals were detected from either nanoparticle at a concentration of less than $10^9$ nanoparticles/mL, suggesting that the PA signals from unbound or non-specifically bound nanoparticles fell below the background level from the blood.

Figure 40:
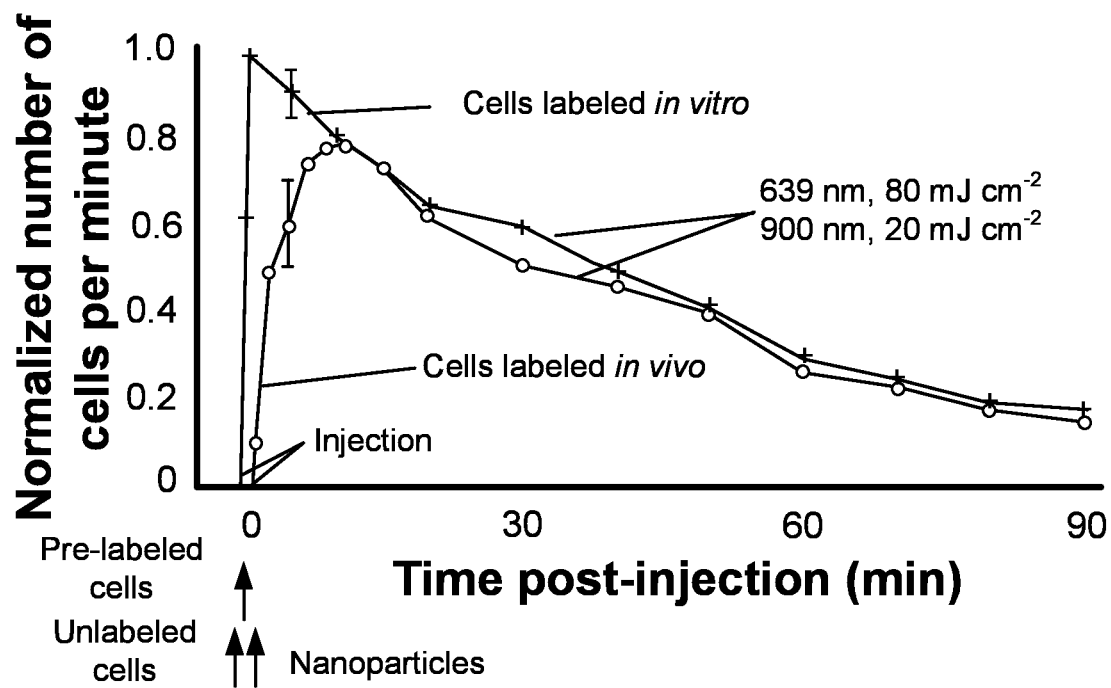
FIG. 40 is a summary of the PA signal rates produced by circulating cancer cells that were labeled with nanoparticles either in vitro or in vivo measured from a mouse abdominal vein an initial injection of the labeled cells (in vitro) or after an initial injection of unlabeled cancer cells followed by a separate injection of conjugated nanoparticles (in vivo) into the tail vein of the mouse.

The depletion kinetics of simulated circulating tumor cells (CTCs) that were labeled in vitro and in vivo were similarly assessed. The in vitro labeled cancer cells were cultured with a 20:80 ratio mixture of GNT-FOL and MNP-ATF particles and then injected into the tail vein of the nude mice. The in vivo labeled cancer cells were formed by first injecting unlabeled cancer cells into the tail vein of the nude mice, followed by an injection of 10 μL of PBS in which a 20:80 ratio mixture of GNT-FOL and MNP-ATF particles was suspended. The labeled cancer cells were monitored in an abdominal vessel of the mice using the PAFC with laser pulses of 639 nm and 900 nm transmitted to the vicinity of the abdominal vessel via laser fiber at laser fluences of 80 mJ/cm$^2$ and 20 mJ/cm$^2$ respectively. FIG. 40 summarizes the results of the PA detection of the in vitro and in vivo labeled CTCs.

After intravenous injection of $10^5$ cancer cells labeled with the nanoparticles in vitro, flashes of photoacoustic signals at both 639 and 900 nm with dominant amplitude at 900 nm were observed immediately after injection, corresponding to the detection of labeled CTCs. The frequency of detected PA signals subsequently declined and disappeared 60-90 minutes after the initial injection of the in vitro labeled CTCs. After the initial injection of the nanoparticles in the in vivo labeling case, photoacoustic signals at both 639 and 900 nm gradually increased in frequency within 8-10 min to approximately the same detection frequency observed from cells labeled in vitro. The subsequent decline in detection frequency of the in vivo labeled CTCs followed a similar pattern of decline as the clearance of the in vitro labeled CTCs. Infrequent PA signals associated with the 900 nm pulse only or the 639 nm pulse only were detected, which may be associated with the targeting of infrequently-occurring CTCs that express only one of the selected biomarkers targeted by the nanoparticle conjugates. The blood surrounding the circulating CTCs produced weak background signals with consistent and comparable amplitudes at both laser pulse wavelengths, and no PA signals with consistent amplitudes consistently above the background signal of the blood was detected other than the CTC detection signals, indicating a negligible background signal originating from unbound circulating nanoparticles.

The results of this experiment indicated that conjugated magnetic nanoparticles and gold nanotubes, particularly in combination, may be used to label circulating tumor cells with high specificity and efficiency, rendering the labeled CTCs amenable to in vivo detection using photoacoustic detection methods.

Example 22. Magnet-Induced Amplification and Visualization of Labeled CD44+ Circulating Tumor Cells Targeted by MNPs To assess the in vivo detection of circulating tumor cells (CTCs) originating from a primary tumor using the in vivo photoacoustic flow cytometry (PAFC) methods described above in combination with cell labeling using conjugated nanoparticles and magnet-induced signal amplification, the following experiments were conducted.

Tumors were induced in nude mice (nu/nu) by inoculating breast cancer xenografts consisting of $5 \times 10^6$ MDA-MB-231 cells subcutaneously into the mice. At 2, 3, and 4 weeks after initial tumor development, a 20:80 ratio mixture of conjugated MNPs and CNTs (described previously in Example 21) was injected into the tail vein of the mice. After allowing 20 minutes for clearing the majority of unbound injected nanoparticles, photoacoustic detection of the labeled CTCs circulating in an abdominal vessel and in an ear vessel was performed using the PAFC device and methods described in Example 21. The results of these measurements are summarized in Table 4.

TABLE 4

Circulating Tumor Cells Detected After Inoculation of Nude Mice With Cancer Xenografts

| | Rate of CTCs Detected (cells/min) | | |
|---|---|---|---|
| Week | Ear Vessel | Abdominal Vessel | Ear:Abdominal CTC Ratio |
| 2 | 0.9 ± 0.3 | 6 ± 2.1 | 0.15 |
| 3 | 7.2 ± 0.3 | 26 ± 0.3 | 0.27 |
| 4 | 15.1 ± 2.7 | 47 ± 6.4 | 0.32 |

Figure 41:
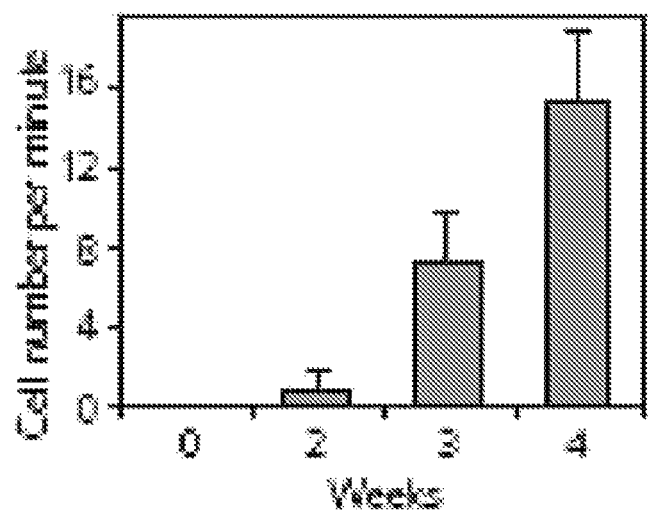
FIG. 41 is a summary of the PA signal rates from circulating tumor cells in a mouse abdominal vein measured at 2, 3, and 4 weeks of tumor development. The circulating tumor cells were labeled in vivo using conjugated magnetic nanoparticles and gold nanotubes.
Figure 42:
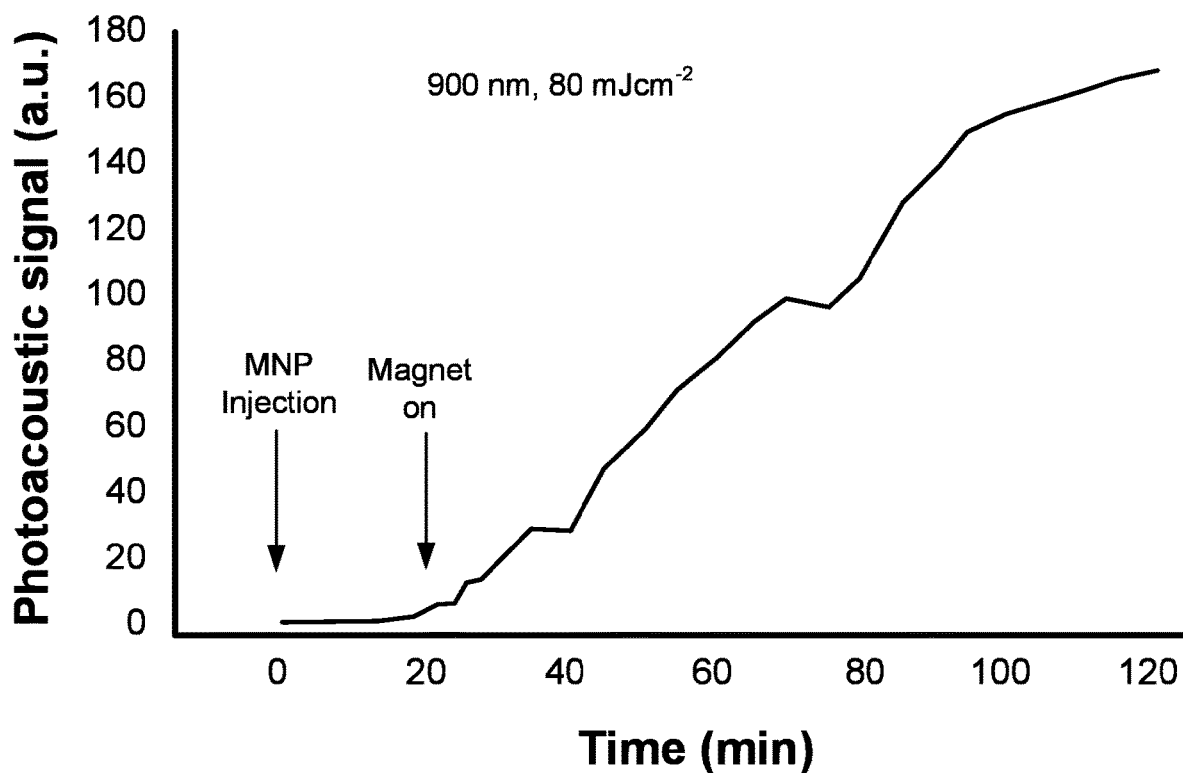
FIG. 42 is a summary of the PA signal rates from circulating tumor cells in an abdominal vein after one week of tumor development. The circulating tumor cells were labeled with magnetic nanoparticles in vivo and an external magnetic field was applied near the area of interest in the abdominal vein 20 minutes after initial injection of conjugated magnetic nanoparticles.
Figure 43:
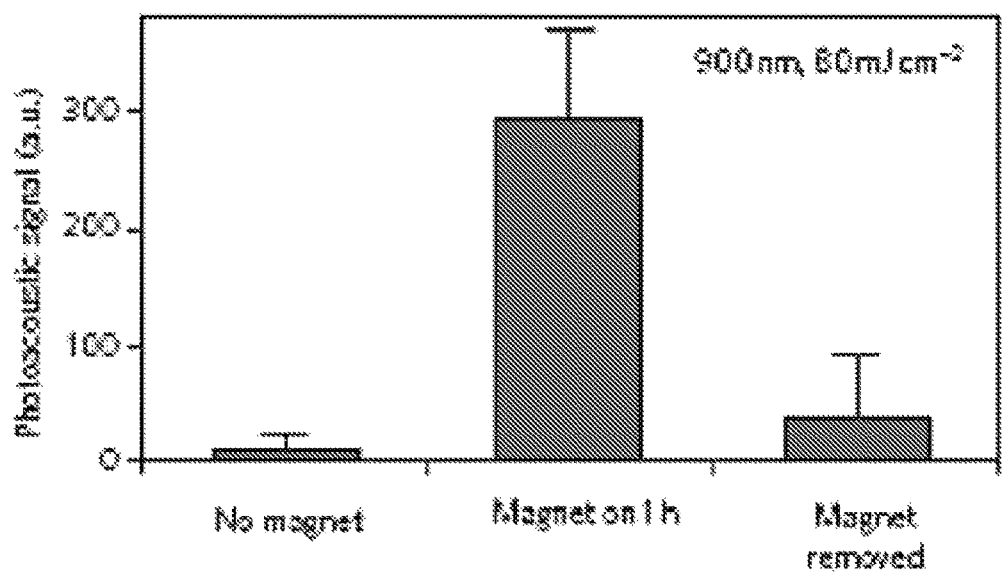
FIG. 43 is a summary of the PA signal rates from circulating tumor cells in an abdominal vein after two weeks of tumor development. The circulating tumor cells were labeled with magnetic nanoparticles in vivo. PA signals were measured before the application of a magnetic field, one hour after the initial application of an external magnetic field, and after the removal of the magnetic field.

As shown in Table 4, the ratio of the CTC detection rate in the mouse ear vessel to the CTC detection rate in the abdominal vessels increased from 2 weeks to 4 weeks. The CTC detection rate in the mouse ear vein, summarized in FIG. 41, was roughly correlated with the stage of the primary tumor progression and vessel sizes. Attaching a magnet similar to the magnet described in Example 21 in the vicinity of the abdominal blood vessel 20 min after the injection of conjugated nanoparticle into the mice at week 1 of tumor development changed the character of the photoacoustic signal from infrequent flashes of signals to a continuous increase of photoacoustic signals, as summarized in FIG. 42. Similar patterns were observed after 2 to 4 weeks of tumor development. As shown in FIG. 43, the signal amplitude in the abdominal vessels of mice at week 2 of tumor development increased 88-fold within one hour of the application of an external magnetic field. Removal of the magnet led to the release of the trapped CTCs bound to nanoparticles, resulting in a decrease in the PA signal amplitudes. This partial decrease in PA signal amplitude may be due to the remaining CTCs left adhered to the vessel wall.

The results of this experiment indicated that duplex molecular targeting of CTCs with functionalized nanoparticles followed by CTC capture and detection using dual magnetic-photoacoustic flow cytometry technology may be feasible for the detection of CTCs circulating in the bloodstream, in vivo, in real time.

Example 23. Magnetic Manipulation and Detection of Blood Cells Using an Extracorporeal Shunt To assess the efficacy of in vivo detection of circulating blood cells in an extracorporeal shunt using the in vivo photoacoustic flow cytometry (PAFC) methods described above, in combination with cell labeling using conjugated nanoparticles and magnet-induced signal amplification, the following experiments were conducted.

Figure 45:
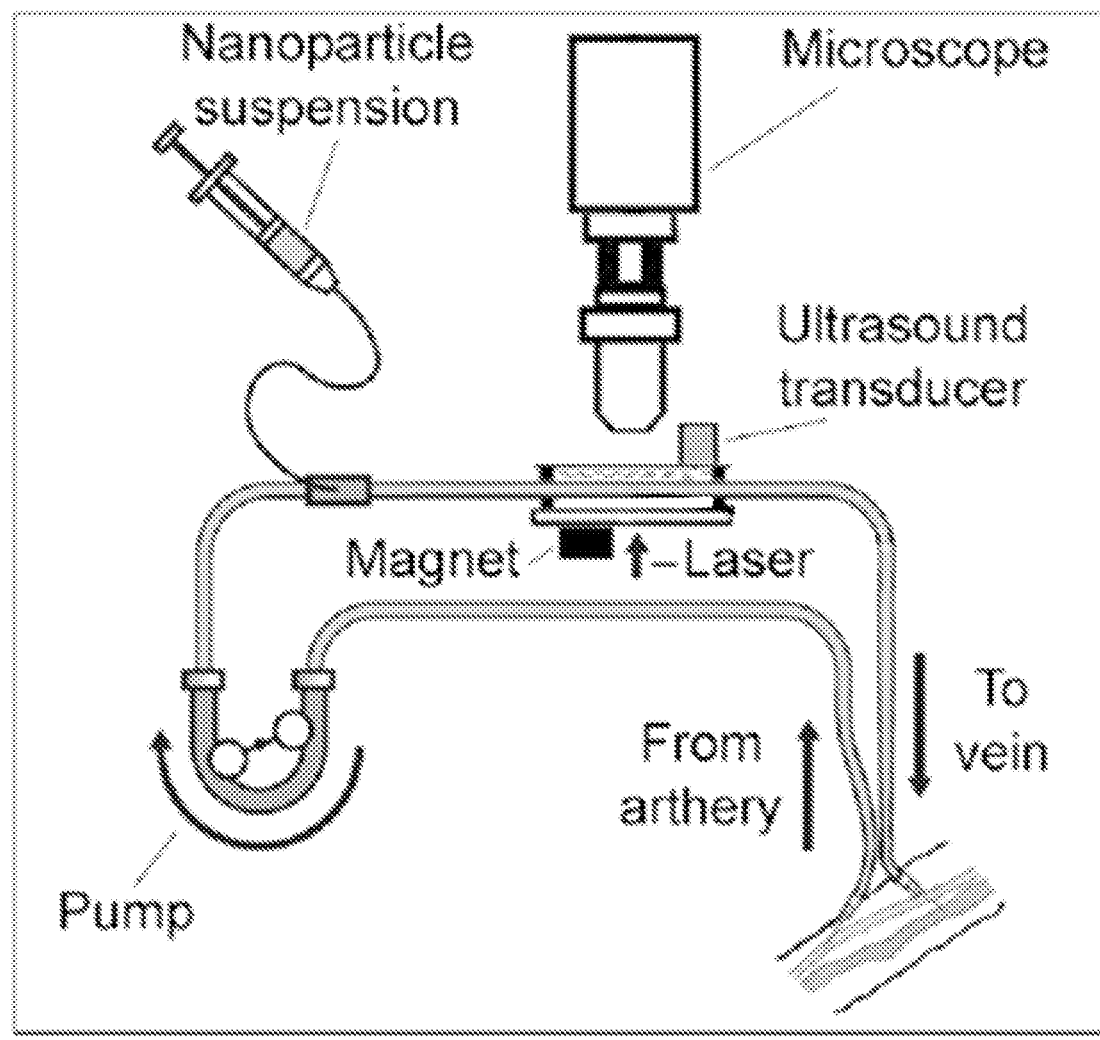
FIG. 45 is a schematic diagram of an extracorporeal shunt.

An extracorporeal shunt, illustrated schematically in FIG. 45, was used to label, magnetically manipulate, and detect circulating tumor cells from a white rat. Catheters were inserted into a large artery and a jugular vein of the rat. Blood from the rat entered the extracorporeal shunt through the arterial catheter and exited the shunt through the jugular catheter. Functionalized magnetic 10-nm nanoparticles were injected into the shunt upstream of the detection point near the magnet and laser and ultrasound transducer. The distances between injection site and detection points may be varied by change of tube length in order to enhance the binding of the functionalized magnetic nanoparticles to the circulating tumor cells. The magnetically labeled in-flow tumor cells were captured by the magnetic field produced by the magnet. Laser irradiation of the detection area near the magnet generated photoacoustic signals which were detected with the ultrasound transducer attached to the tube. The photoacoustic amplitude signals were found to be correlated with concentration of the magnetically captured circulating tumor cells (not shown).

Conventional transmission imaging in the detection area provided information used to control the position of the laser beam, magnet, and ultrasound transducer. Using the high speed/high resolution imaging mode of the optical system also provided visualization of individual moving cells at the single cell level.

The results of this experiment demonstrated that the extracorporeal shunt provided photoacoustic continuous monitoring of shunted blood flow in an external tube, and the efficient capture of magnetically labeled abnormal circulating objects (e.g., tumor cells, bacteria, toxin, or drug) targeted by the magnetic nanoparticles within the extracorporeal flow. In addition, the magnetic capture of both magnetically-labeled abnormal objects and unbound magnetic nanoparticles prevented their further introduction into the systematic circulation of the rat.

Example 24. A Prototype Theranostic Platform was Used to Detect and Destroy Unlabeled Bacterial Cells In Vitro To assess the capability of a prototype PA/PT theranostic system for detecting and killing unlabeled S. aureus bacteria in vitro, the following experiments were conducted. A PAFC system similar to the system described in Example 2 was used as a prototype theranostic platform to detect S. aureus cells of the UAMS-1 strain described in Example 4.

The bacteria were suspended in phosphate-buffered saline solution at a concentration of $10^8$ cells/mL and subjected to spectrophotometric analysis using a fiber spectrophotometer (USB4000, Ocean Optics Inc., USA) at wavelengths ranging from about 400 nm to about 900 nm.

The bacteria cells were suspended in phosphate-buffered saline solution at a concentration of $10^6$ CFU/mL for PT analysis. The bacterial suspension was subjected to PT spectroscopic methods similar to those described in Example 6 for unlabeled melanoma cells. The suspended bacteria cells situated within a 1-cm optical pathway were pulsed at pulse wavelengths ranging from about 600 nm to about 900 nm, and at fluences of 1.8 J/cm$^2$ and 4.5 J/cm$^2$.

Figure 47:
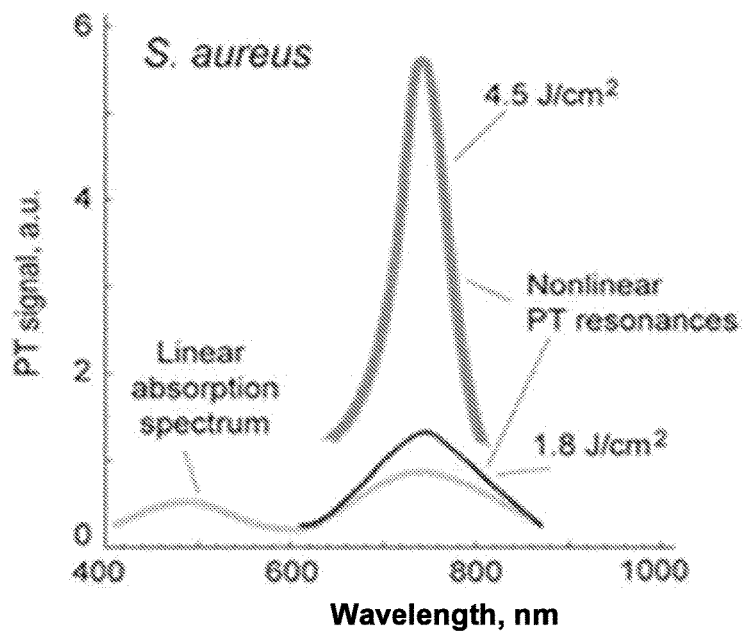
FIG. 47 is a graph summarizing the absorption and PT spectra of label-free S. aureus.

The results of the spectrophotometric analysis and PA spectroscopy of the bacterial suspensions are summarized in FIG. 47. The photoabsorbance spectra exhibited two absorption peaks near 462 nm and 741 nm, possibly associated with carotenoids. PT spectroscopy at low laser energy fluence (1.8 J/cm$^2$) confirmed the 741 nm peak. The average standard deviation in PT data for each wavelength at automated laser spectral scanning was 21%. Laser-induced nanobubbles produced by the laser pulses delivered at higher energy fluence (4.8 J/cm$^2$) induced PA signals that were about 10-fold higher than the PA signals produced by the lower energy fluence pulses, accompanied by spectral narrowing of the absorption band.

Figure 48A:
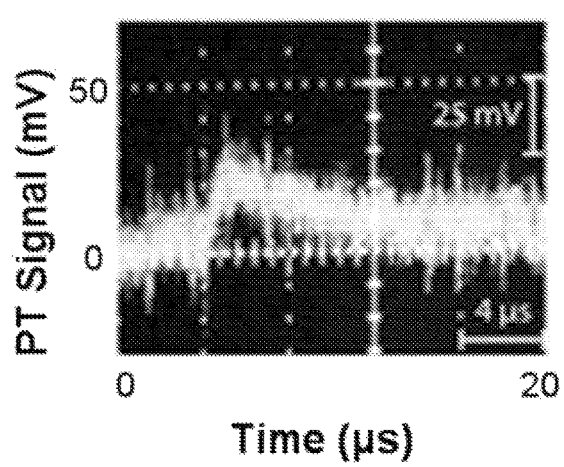
FIG. 48A is an oscilloscope trace of a linear PT signal induced by a low-energy laser pulse.
Figure 48B:
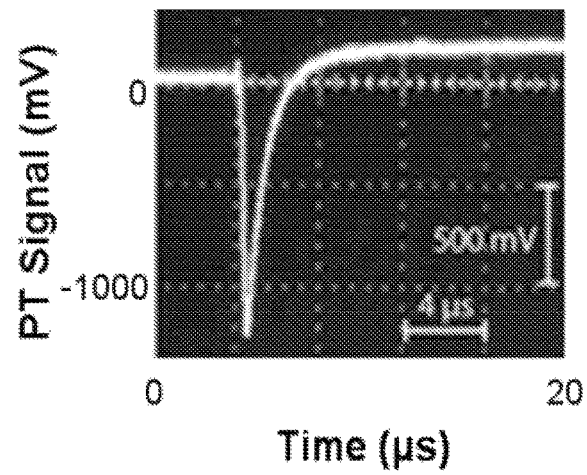
FIG. 48B is an oscilloscope trace of a non-linear PT signal induced by a high-energy laser pulse.

The intrinsic photothermal (PT) properties of individual S. aureus cells were assessed further by analyzing individual PT and PA signals measured by the prototype theranostic system. FIG. 48A and FIG. 48B are images of the oscilloscope traces of PT signals induced by a laser pulse delivered at a pulse wavelength of 740 nm and low energy fluence (0.9 J/cm$^2$) and high energy fluence (1.8 J/cm$^2$). The linear PT signal illustrated in FIG. 48A was characterized by a fast-rising unipolar positive peak associated with rapid (picosecond-nanosecond scale) heating and a slower (microsecond scale) tail corresponding to cooling of the bacterial cell. Lased-induced nanobubbles around the bacteria cell overheated by the high energy fluence were characterized by a nonlinear negative peak likely resulting from scattering and refraction of the probe beam. Subsequent optical imaging (not shown) of the bacterial cells indicated that the cells subjected to low energy fluence pulses remained intact, and the cells subjected to the high energy fluence pulses experienced significant photodamage.

The low laser energy fluence was sufficient for the non-invasive detection of a single bacterium in the irradiated volume, and the high-energy fluence induced to cell death as confirmed by specific changes in the PT signal shape and the cell architecture of the bacterium.

The results of this experiment confirmed that the prototype theranostic system is capable of detecting and killing individual unlabeled S. aureus cells in vitro at two wavelengths of laser pulse corresponding to the peak absorptions of the S. aureus.

Example 25. A Prototype Theranostic Platform was Used to Detect Unlabeled Bacterial Cells In Vivo To assess the effectiveness of identifying circulating CBCs in vivo, the mouse ear model described in Example 2 was used to detect unlabeled circulating bacterial cells (CBCs), in this case the unlabeled S. aureus cells described in Example 4.

A 20 μL aliquot of unlabeled S. aureus cells suspended at a concentration of $10^4$ CFU/mL was injected into a blood vessel in the ear of a mouse to simulate a localized bacterial infection. The prototype theranostic platform described in Example 24 was used to detect the resulting CBCs using the mouse ear model. For comparison, similar measurements were performed prior to the injection of the bacterial suspension. For the measurements in these experiments, a laser pulse wavelength of 741 nm and an energy fluence of 1 J/cm$^2$ were used to induce photoacoustic (PA) signals from the bacterial cells.

FIG. 49A is an oscilloscope trace of a PA signal produced by an unlabeled bacteria cell in response to a laser pulse as detected by the prototype theranostic system. FIG. 49B is an oscilloscope trace of the background PA signals (control) measured in response to a laser pulse in the absence of a bacteria cell. Relative to the background PA signals, the PA signals produced by the unlabeled bacteria cell were significantly higher in magnitude. The ratio of PA signal strength relative to background PA signals ranged from about 3 to about 6.

To further demonstrate the detection of unlabeled CBCs in vivo, circulating unlabeled bacterial cells were detected using the mouse abdominal vessel model described previously in Example 7. Photoacoustic measurements were performed in a 300-μm abdominal blood vessel of the mouse using the prototype theranostic system at the same laser pulse wavelength and fluence used previously in this experiment. After obtaining measurements prior to the introduction of the bacterial suspension as a baseline, a 20 μL suspension of unlabeled S. aureus cells at a concentration of $10^4$ CFU/mL was injected into the tail vessel of a mouse while continuing to perform the photoacoustic measurements.

The results of the PA signals obtained from the mouse abdominal vessel are summarized in FIG. 50. The label-free PA detection of blood-borne S. aureus cells in the mouse abdominal vessel model proved elusive due to the PA signal noise introduced by the blood background.

The results of this experiment demonstrated that unlabeled CBCs may be detected in vivo at high concentrations. At lower concentrations, the PA signals produced by the CBCs may be challenging to differentiate from the blood background PA signals.

Example 26. PA Detection of Labeled S. aureus Cells Targeted by Functionalized Gold Nanoparticles was Demonstrated In Vitro To assess the in vitro PA detection of S. aureus cells targeted by compounds functionalized with bacteria-targeted antibodies, the following experiment was conducted.

Figure 51:
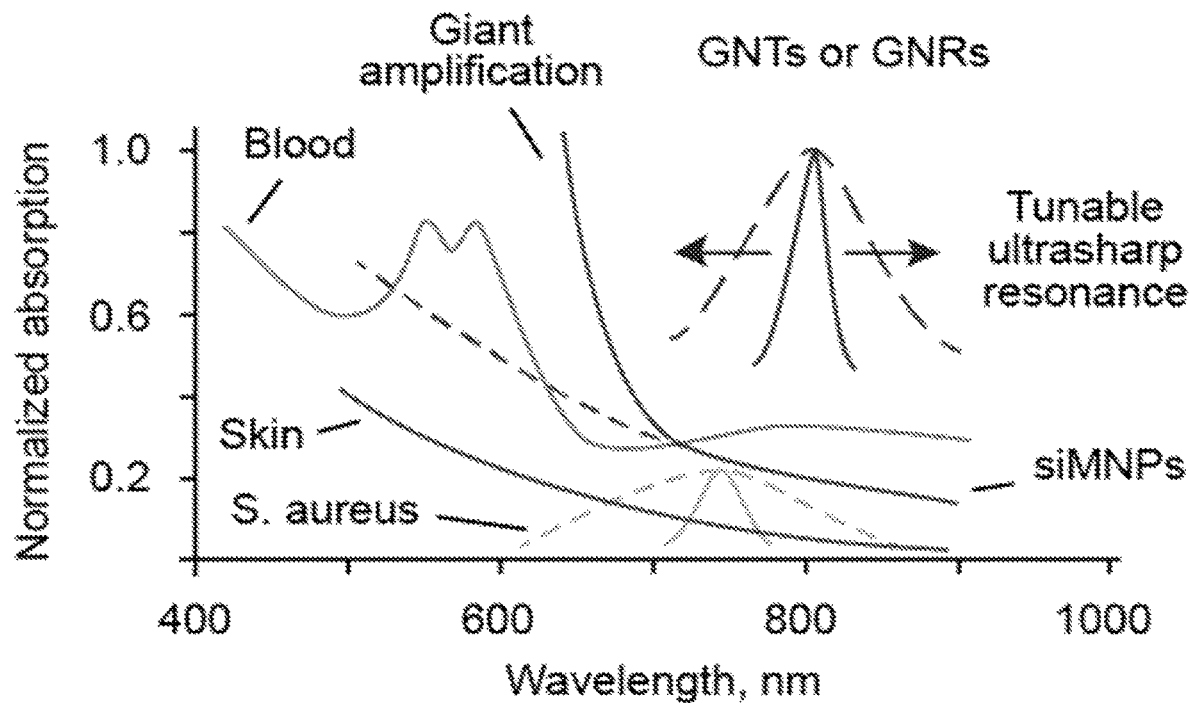
FIG. 51 is a graph summarizing the spectrum of absorption of light by various nanoparticles at wavelengths ranging from about 400 nm to about 1000 nm.

The theranostic platform was used to detect bacterial cells in vitro at the level of a single bacterial cell, as described previously in Example 24. The bacteria cells used were S. aureus cells of the UAMS-1 strain described previously in Example 4. To facilitate multiplexing, spectrally tunable golden carbon nanotubes (GNTs) and gold nanorods (GNRs), as well as silica-coated magnetic nanoparticles (siMNPs) were used to label the bacteria cells. FIG. 51 is a graph summarizing the spectrum of absorption of light at wavelengths ranging from about 400 nm to about 1000 nm. Dashed and solid lines indicate averaged linear and nonlinear PA spectra, respectively.

To increase the specificity of labeling, the nanoparticles were functionalized by conjugation to antibodies specific for S. aureus protein A (anti-Spa) and/or lipoprotein (anti-Lpp), both of which are highly expressed in S. aureus and absent in mammalian cells. GNTs were conjugated with an Ig fraction of anti-Spa antibodies. GNRs with maximal adsorption at 900 nm ($GNR^{900}$) were bioconjugated with anti-Spa antibodies and GNRs with maximal adsorption at 690 nm ($GNR^{690}$) were bioconjugated with anti-Lpp antibodies. A portion of the nanoparticles were additionally conjugated with Fluorescein Isothiocyanate (FITC). The FITC-conjugated Ig fraction of anti-Spa and Phycoelythrin (PE)-conjugated anti-Lpp antibodies were additionally purchased for verification by fluorescence imaging taking into account the excitation of 490 nm and emission of 525 nm for FITC and the excitation of 488 and 565 nm and emission of 578 nm for PE.

Bacteria were incubated with nonconjugated nanoparticles at 37° C. for 30 and 60 minutes, and were incubated for an additional 30 minutes with functionalized NPs at 37° C. to ensure thorough specific binding of the nanoparticles to the bacteria. The resultant bacterium-nanoparticle complexes were washed three times in PBS by centrifugation (5,000 rpm; 3-5 min). Both conjugated and non-conjugated cells were typically incubated at the relation of 1,000-10,000 NPs per one bacterium. In selected tests with anti-Spa-GNTs and anti-Spa-GNRs proportions ranged from 10 NPs to 100,000 NPs per one bacterium. The attachment of NPs to bacterial cells was verified using three techniques: (1) comparing PT signals from individual labeled and unlabeled cells at wavelengths coinciding with maximum absorption of nanoparticles; (2) imaging with atomic force microscopy (AFM); and (3) fluorescent imaging when nanoparticles were additionally labeled with fluorescent dyes.

Figure 52:
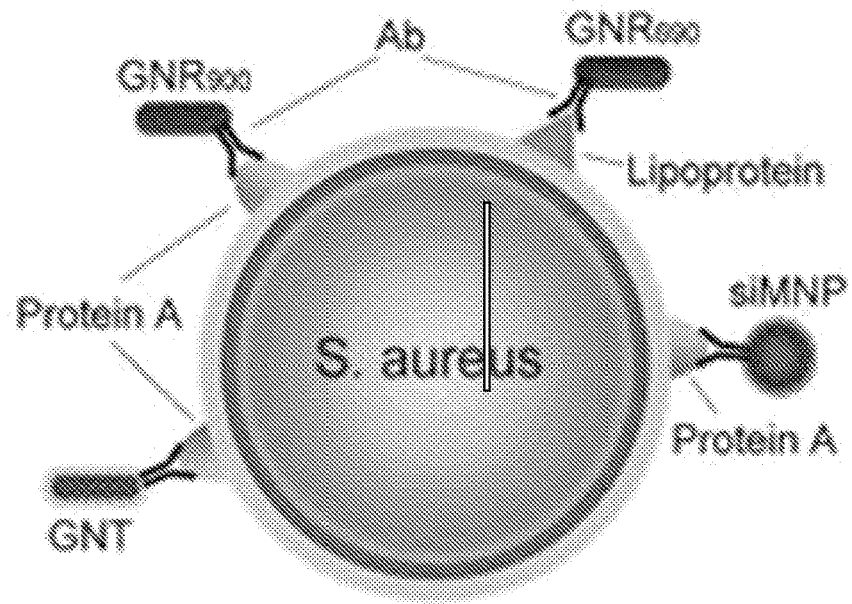
FIG. 52 is a schematic diagram illustrating the multiplex targeting of S. aureus surface proteins by nanoparticles functionalized with bacteria-specific antibodies.
Figure 53:
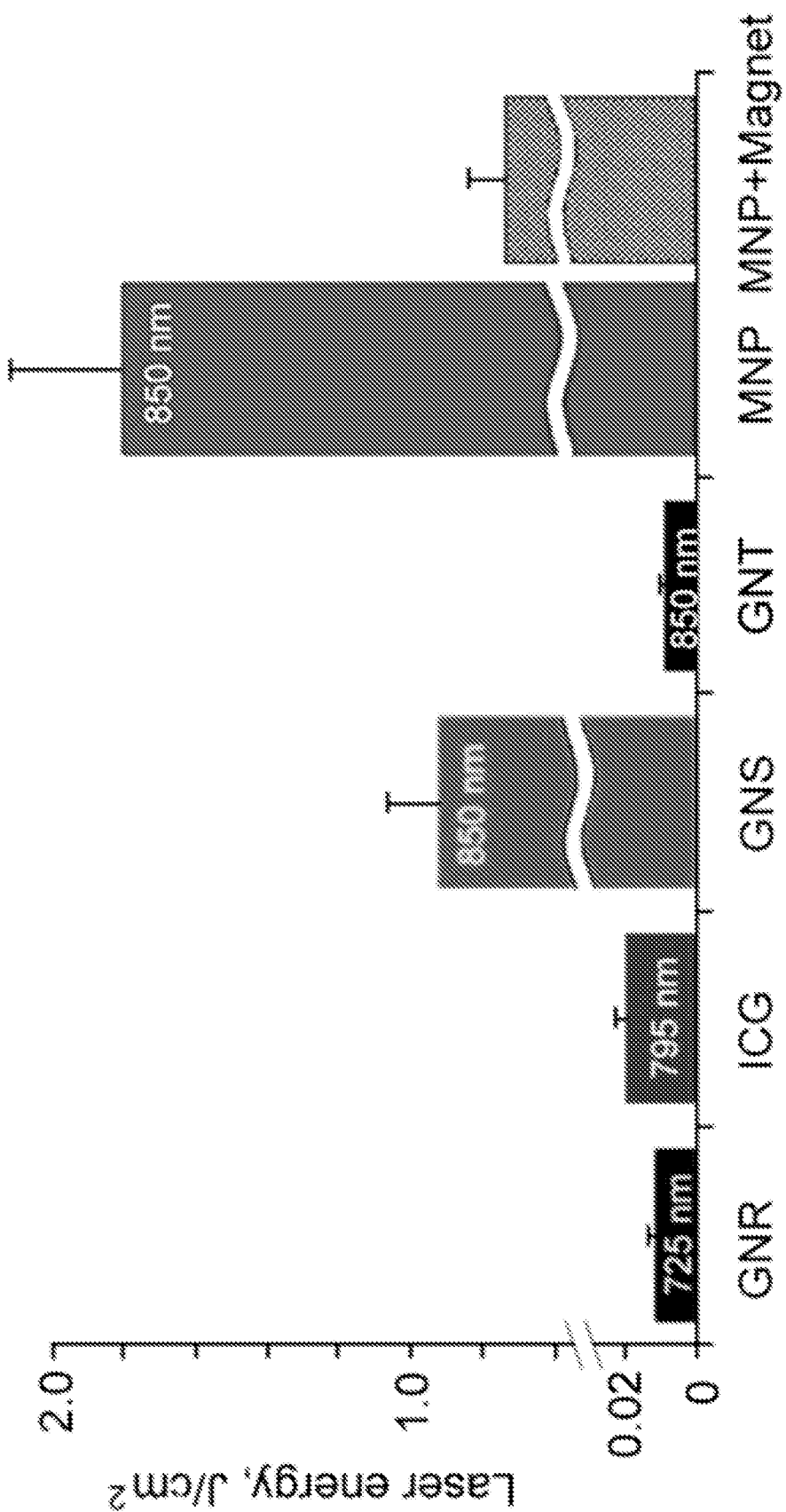
FIG. 53 summarizes levels of laser energy fluences that produce detectable PT signals from S. aureus cells labeled with non-conjugated nanoparticles and dye (ICG).

FIG. 52 illustrates the multiplex targeting S. aureus surface biomarker protein A (Spa) and lipoprotein (Lpp) by siMNPs, GNRs and GNTs functionalized with either anti-Spa or anti-Lpp antibodies. FIG. 53 summarizes typical levels of laser energy fluence producing detectable PT signals from S. aureus cells labeled with non-conjugated nanoparticles and dye (ICG).

Fluorescent imaging of bacteria labeled with nanoparticle-antibody-fluorescent dye conjugates (FITC and PE; 30 min, 37° C.) indicated that 82.5% of bacteria were detectable with the anti-Spa antibody (termed anti-Spa), 81.2% with the anti-Lpp antibody (termed anti-Lpp), and 89.7% with both antibodies, confirming the increased targeting efficiency obtained with multiple antibodies. The nanoparticle-labeled bacteria were detected using PA/PT microscopy/cytometry at laser pulse wavelengths corresponding to the maximum absorption wavelengths of the nanoparticles; 30- to 50-fold PA signal increases were observed due to the addition of the nanoparticle labels. FIG. 53 is a summary of representative levels of laser energy fluence that produced detectable PT signals from S. aureus cells labeled with non-conjugated NPs (GNTs, GNRs, GNSs, and MNPs) and dye (ICG).

Targeting efficiency of anti-Spa antibodies to S. aureus in PBS was 96.3% (±4.23%) on the basis of the light microscopy image analyses. The number of GNTs bound to S. aureus, on the basis of the image analyses at multiple sections of the GNT-targeted cells, varied from 50 to 400 per cell (about 100 GNTs per cell on average) depending on incubation time and concentration of bacteria and GNTs.

Labeled and unlabeled bacteria were detected using the prototype theranostic system described in Example 24 and a method similar to the method of Example 10. The comparison of PA/PT signals from unlabeled control bacteria and bacteria labeled with anti-Spa conjugated to GNR, anti-Lpp conjugated GNR, or a combination of the two GNRs confirmed targeting efficiencies of 91.1%, 89.0% and 96.4% respectively. Compared to fluorescent tags, the increased nanoparticle targeting efficiency is likely due to the higher PT/PA contrast, which requires an average of 1,000 GNRs per cell. Decreasing the number of antibody-conjugated GNRs per cell to 100 still provided detectable signals, at least in vitro, without a decrease in targeting efficiency. Even at 10 GNRs per cell, detectable signals were obtained, although targeting efficiency decreased to less than 60%. Similar efficiency was observed with antibody conjugated GNTs (92.4% with 100 GNT per cell). Nonspecific binding in all cases was in the range of 5-8%.

The labeling efficiency of S. aureus (1 h, 37° C.) in static condition in vitro obtained with fluorescent and PA techniques is summarized in Table 5.

TABLE 5

Labeling efficiency (%) of S. aureus (1 h, 37° C.) in static condition in vitro obtained with fluorescent and PA (in brackets) techniques

| | Labeling Efficiency of Antibodies (Nanoparticles) | | |
|---|---|---|---|
| Samples | Anti-LPP($GNR^{900}$) | Anti-Spa($GNR^{690}$) | Anti-LPP($GNR^{900}$) + Anti-Spa($GNR^{690}$) |
| Bacteria in PBS | 81.2 ± 1.9% (91.1 ± 3.1%) | 82.5 ± 2.4% (89.0 ± 2.8%) | 89.7 ± 2.9% (96.4 ± 3.2%) |
| Bacteria in mouse blood | 67.7 ± 1.8% | 72.1 ± 2.0% | 79 ± 2.6% |
| Mouse blood with no bacteria (control) | 8 ± 1.3% | 6 ± 1.2% | 10 ± 1.6% |

The results of this experiment demonstrated that CBCs could be efficiently labeled with functionalized nanotubes, nanorods, or nanoparticles. The results of this experiment demonstrated that functionalized nanoparticles may be used to label bacteria with acceptable efficiency at levels that may be detected by PA.

Example 27. PA Detection of CBCs Targeted by Functionalized Gold Nanoparticles was Demonstrated In Vivo To demonstrate the in vivo detection of circulating bacterial cells (CBCs) targeted by functionalized gold nanoparticles, the following experiment was conducted. The mouse ear model described in Example 2 was used to detect labeled CBCs similar to those described in Example 26. The detection of the labeled CBCs used the PA/PT theranostic system described in Example 20.

Figure 54A:
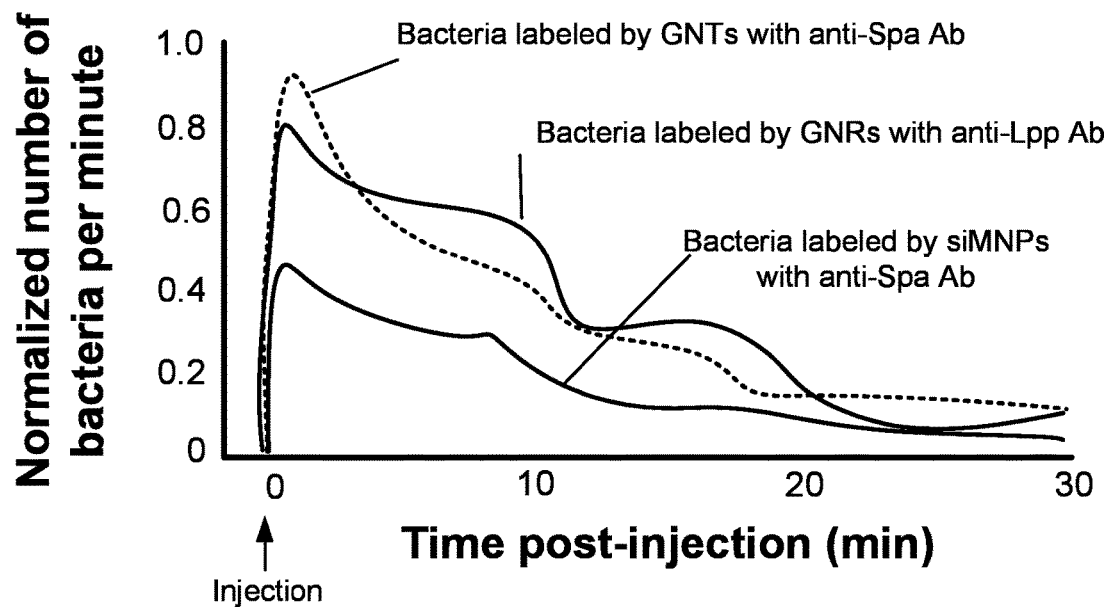
FIG. 54A is a summary of the detection of pre-labeled bacteria for 30 minutes after injection into a mouse tail vein.

S. aureus cells were pre-labeled with anti-Spa conjugated GNTs and/or anti-Lpp conjugated GNRs as described previously in Example 26. Labeled bacterial cells ($10^5$) were introduced by tail vein injection into mice, with PA signals monitored via a 50-μm blood vessel in the ear using the prototype theranostic system described in Example 25. For these experiments, laser pulses with wavelengths of 671 nm and 820 nm and a pulse energy fluence of 0.1 J/cm² was used to elicit the PA signals from the labeled bacteria cells. The time courses of the detection of the injected bacteria are summarized in FIG. 54A. After injection of the labeled bacteria cells, PA signals associated with the labeled bacteria cells were detected within the first minute, reached a maximum within 3 minutes, and gradually declined over the next 20 minutes.

To assess the efficacy of in vivo labeling and detection of bacteria cells using the prototype theranostic device, the following experiment was conducted. Bacteria cells were labeled in vivo by injecting $10^5$ unlabeled S. aureus cells followed by injecting $10^9$ of an antibody-conjugated nanoparticle cocktail consisting of GNRs[690] with antibodies and GNRs[900] with anti-Spa antibodies in a 50%:50% proportion in 20 µL of phosphate-buffered saline. PA monitoring of the mouse ear vessel was performed prior to and following the injections as before. The average standard deviation for each time point in FIG. 54A was 18%.

Figure 54B:
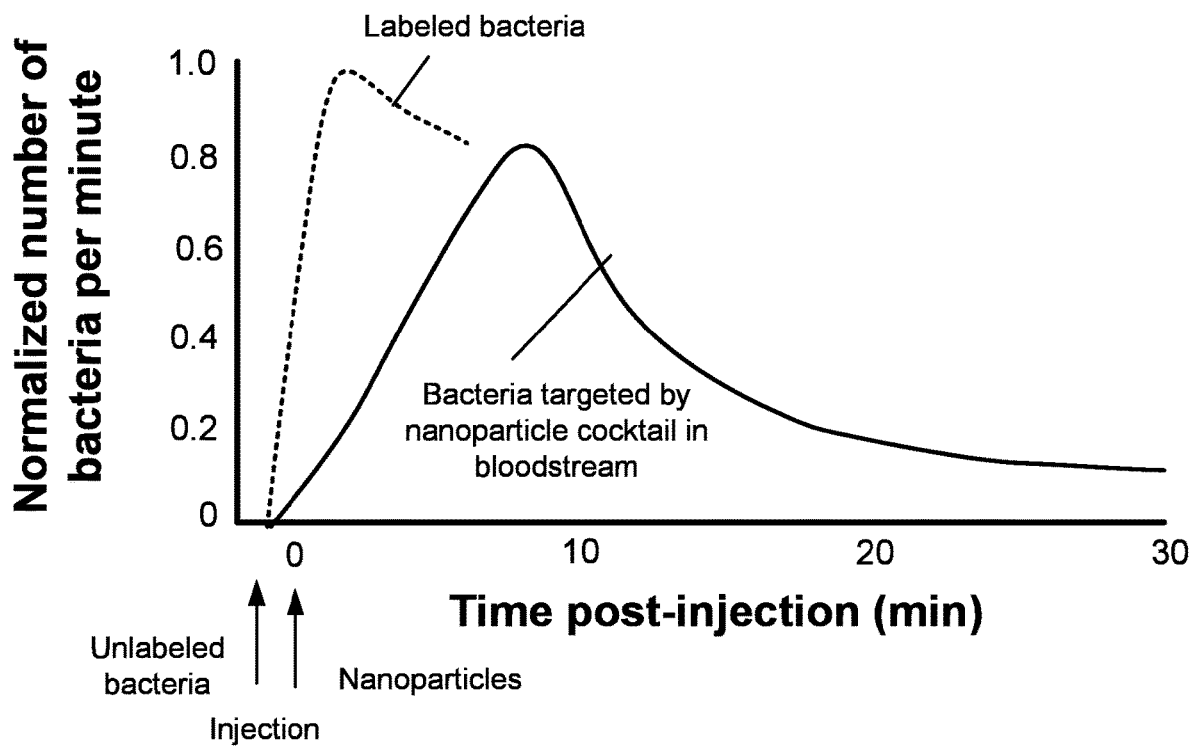
FIG. 54B is a summary of the detection of bacteria that were labeled in vivo.

FIG. 54B is a summary of the PA signals detected from the CBCs labeled in vivo. The inset graph shows typical PA signal traces and the dashed line indicates the detected PA signals observed when the same cocktail was used to label *S. aureus* cells in vitro prior to injection. The average standard deviation for each time point in FIG. 54B was 18%. No PA signals were detected immediately after injection, but an increase in both PA signal number and amplitude was observed during the 10 minute period after injection of nanoparticles, as seen in FIG. 54B. After reaching its maximum, there was a gradual decrease in signal intensity, with a clearance time comparable to that observed with in vitro labeled bacteria as summarized in FIG. 54A. No PA signals were detected when the functionalized nanoparticles were injected alone at a concentration $\leq 10^9$ (data not shown). These data suggest successful in vivo targeting of *S. aureus* cells circulating in the bloodstream approximately 10 min after antibody-conjugated nanoparticle injection without any signal interferences from unbound nanoparticles, which were below background noise.

The results of this experiment demonstrated the targeting and detecting of CBCs that were labeled in vivo using functionalized nanoparticles.

Example 28. PA Detection of Silica Coated Magnetic Nanoparticles (siMNP) was Demonstrated In Vitro To assess the efficacy of in vitro PA detection of silica-coated magnetic nanoparticles, the following experiments were conducted.

Silica-coated iron oxide magnetic nanoparticles (siMNPs) were suspended in solution on a slide and PA and PT signals produced by the siMNPs under various conditions were detected. The majority of siMNPs contained either one MNP core or two or more MNP cores (MNP clusters) consisting of 30-nm magnetite ($Fe_3O_4$) nanoparticles similar in composition to the nanoparticles described in Example 19. The siMNPs consisted of the MNP core coated with a silica coating. The thickness of the silica coating was about 10 nm on average for the siMNP with a single MNP core.

Figure 55A:
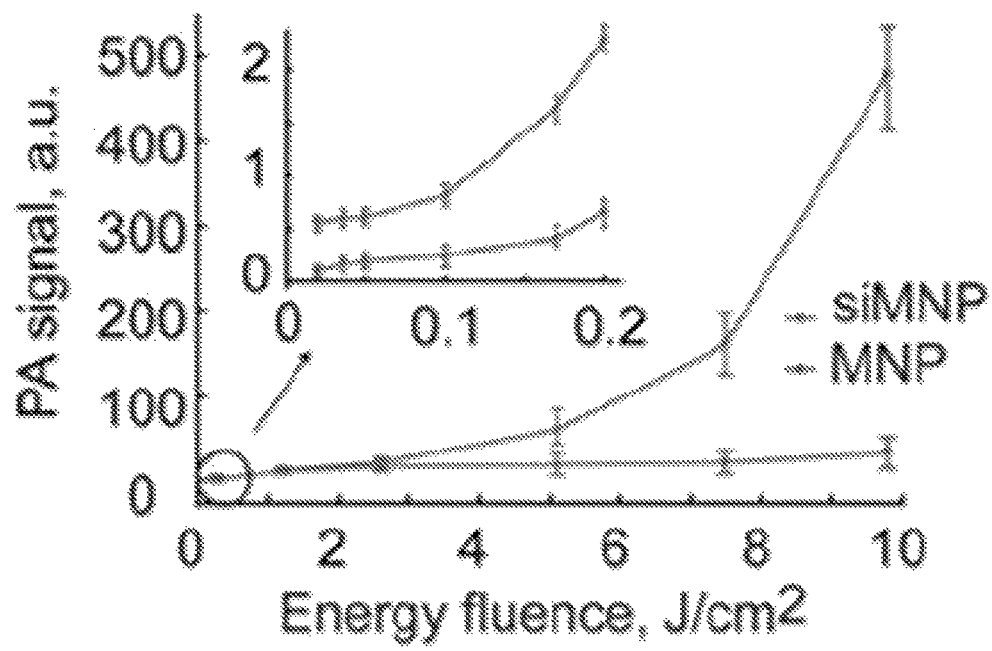
FIG. 55A is a summary of the PA signals produced by magnetic nanoparticles (MNPs) and silica-coated magnetic nanoparticles (siMNPs) in response to laser pulses with varying energy fluences.

The prototype theranostic device described in Example 24 was used to detect the PA signals produced by the unbound magnetic nanoparticles in vitro. Laser pulses were delivered to the unbound siMNPs as well as siMNPs lacking the silica coating (MNPs) at a pulse wavelength of 640 nm, a pulse rate of 10 Hz, and a pulse energy fluence ranging from 20 mJ/cm$^2$ to 10 mJ/cm$^2$. FIG. 55A summarizes the PA signal strength resulting from exposure of the siMNPs and MNPs to laser pulses of different pulse energy fluences. The siMNPs exhibited a nonlinear PA signal amplification compared to the MNPs. At low laser energy (i.e., in linear mode), siMNPs demonstrated 1.8 to 2.5-fold increased PA signals compared to MNPs alone (see inset graph). At higher laser energy, a 20 to 35-fold nonlinear PA/PT signal amplification was observed, a phenomenon referred to as giant amplification.

Figure 55B:
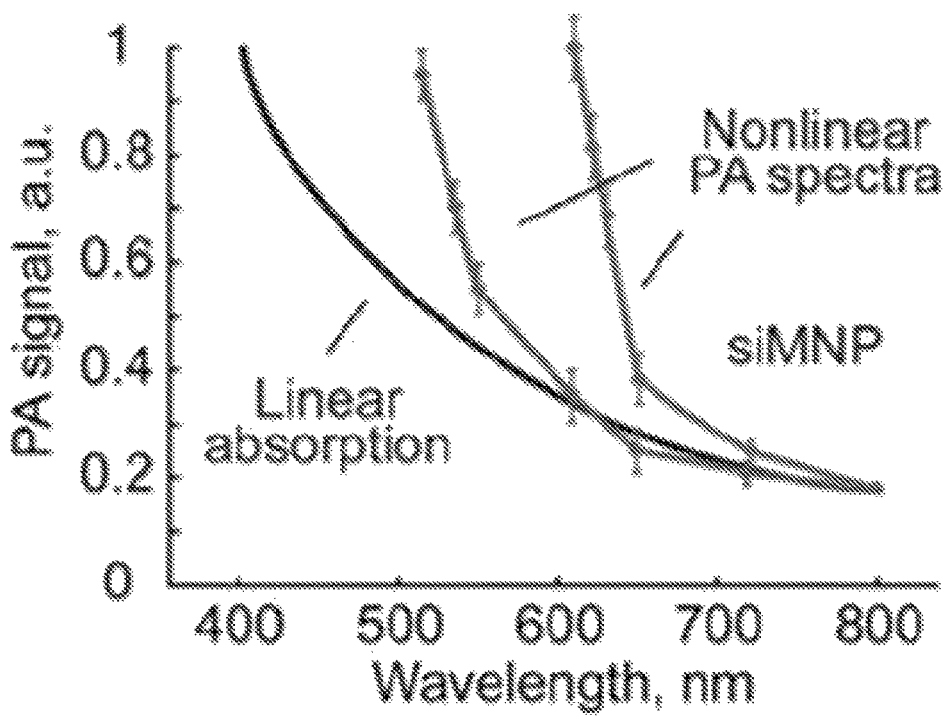
FIG. 55B is a summary of the PA signals produced by silica-coated magnetic nanoparticles (siMNPs) in response to laser pulses with varying wavelengths.

The siMNPs were exposed to lasers pulses with energy fluences of 0.3 and 5 J/cm$^2$ and pulse wavelengths ranging from 400 nm to 800 nm to assess the spectral response of the siMNPs. FIG. 55B summarizes the nonlinear PA spectra of siMNPs at 0.3 and 5 J/cm$^2$ energy fluences as compared to the linear absorption spectrum measured using PA spectroscopic methods similar to those described in Example 6. In FIG. 55B, both PA spectra were normalized on absorption spectra at 800 nm, and the error bars represent the standard deviations in five measurements. The non-linear amplification of the PA signals associated with the siMNPs persisted throughout the range of pulse wavelengths tested.

Figure 56A:
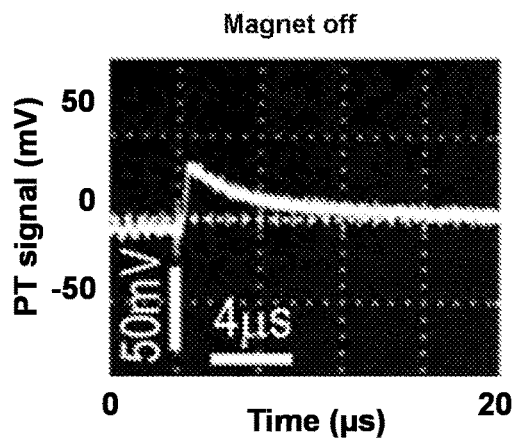
FIG. 56A is an oscilloscope trace of a PT signal produced by an bacteria cell labeled with a non-conjugated siMNP with no magnetic field applied.
Figure 56B:
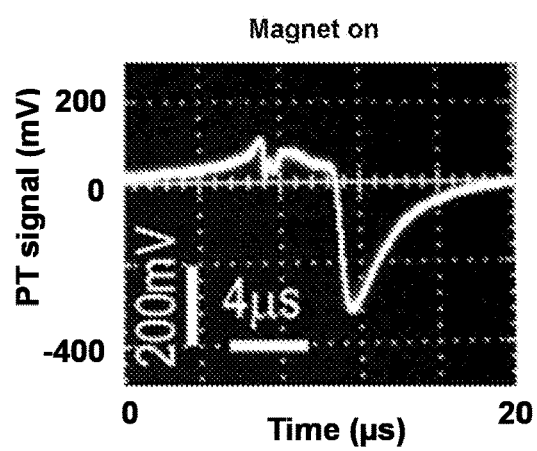
FIG. 56B is an oscilloscope trace of a PT signal produced by bacteria cells labeled with a non-conjugated siMNP and clustered in the presence of an applied magnetic field.

*E. aurelius* bacteria cells were labeled with the nonconjugated 30-nm siMNPs using methods similar to those described in Example 26. The bacteria cells were suspended and placed on a slide. The effects of clustering siMNPs in the presence of a magnetic field on PA signal strength was assessed by detecting the PA signal produced by the siMNP-labeled bacteria cells in vitro in the presence and absence of a magnetic field. A cylindrical Neodymium-Iron-Boron (NdFeB) magnet with Ni—Cu—Ni coating, 3.2 mm in diameter and 9.5 mm long with a surface field strength of 0.39 Tesla provided a local permanent magnetic field to the siMNPs. FIG. 56A and FIG. 56B are images of the oscilloscope traces of the PT signals obtained from the siMNP-labeled bacteria cells in vitro before and after the 3-minute application of the magnetic field, respectively. The magnet-induced clustering of the siMNPs provided a nonlinear PT and PA signal increase due to the enhanced nanobubble formation around strongly-absorbing siMNP clusters.

The results of this experiment demonstrated the PA/PT detection of siMNPs in vitro.

Example 29. Magnetic Amplification of Bacteria Labeled by Functionalized siMNPs was Demonstrated In Vivo To demonstrate the in vivo PA/PT signal amplification of bacteria labeled with functionalized magnetic nanoparticles, the following experiment was conducted. The siMNPs similar to those described in Example 28 were functionalized with anti-Spa antibodies using methods similar to those described in Example 26.

The bacteria were labeled in vitro with the functionalized siMNPs using methods similar to those described in Example 28. The pre-labeled bacteria cells were then injected into a rat tail vein and monitored using the rat mesentery model described previously in Example 3. The prototype theranostic device described in Example 24 was used to obtain PA signals from the rat mesentery vessel using a pulse wavelength of 639 nm and a pulse energy fluence of 0.1 J/cm$^2$. A magnet similar to the magnet described in Example 28 was used to produce a localized magnetic field within the mesentery vessel while continuously monitoring for PA signals associated with the labeled bacteria. The distances between the magnet and examined vessels ranged from 10-20 µm for mesenteric vessels.

Figure 57A:
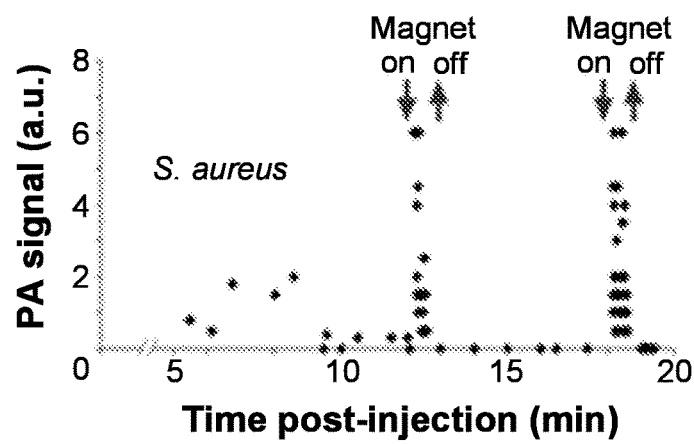
FIG. 57A is a summary of the PA signals produced by bacterial cells pre-labeled in vitro with functionalized siMNPs with two discrete applications of a magnetic field.

FIG. 57A is a summary of the PA signals detected after the injection of the pre-labeled bacteria cells, as well as before and after the application of a local magnetic field for two one-minute periods. The inset graphs illustrate typical PA signal traces. After the pre-labeled were introduced by tail vein injection in rat, only rare PA signals were observed. However, when a magnet was applied initially to the mesentery vein, a significant increase in both the amplitude and rate of PA signals was immediately observed. Removal of the magnet led to a short-term increase in signal rate, likely due to the release of trapped bacteria, followed by the disappearance of detectable signals. Subsequent attachment and removal of the magnet again led to similar phenomena.

In addition, the bacteria were labeled with the functionalized 30-nm siMNPs in vivo using methods similar to those described in Example 27 and detected using the mouse ear model described in Example 2. The unlabeled bacteria were introduced into the bloodstream via tail vein injection followed by the introduction of antibody conjugated siMNPs, also via tail vein injection. A magnetic field was applied using the magnet situated at a distance ranging from 50 to 100 µm from the ear vessels.

Figure 57B:
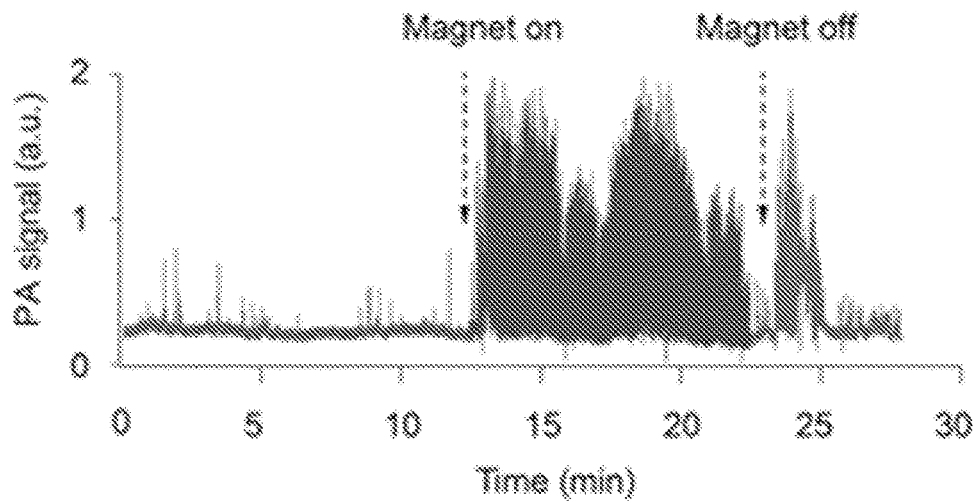
FIG. 57B is a summary of the PA signals produced by bacterial cells labeled in vivo with functionalized siMNPs a three-minute application of a magnetic field.

FIG. 57B shows in vivo real-time monitoring of PA signals produced by the bacteria labeled in vivo before, during, and after magnetic field exposure in a mouse ear using a laser with a 671 nm wavelength and energy fluence of 0.1 J/cm$^2$. The magnet attachment led to a 10 to 15-fold amplification of PA signals. Slight fluctuations in PA signal amplitude and rate suggests a dynamic balance of bacteria near the magnet, with some proportion of trapped bacteria being randomly removed by shear forces. In general, the combination of PA signal amplification with antibody conjugated siMNPs and magnetic trapping of siMNP-labeled bacteria resulted in greater than 100-fold enhancement of sensitivity.

The results of this experiment demonstrated the PA signal amplification of bacteria labeled through targeted siMNPs in vivo.

Example 30. The Monitoring of Bacteria Extravasations and Dissemination was Demonstrated In Vivo To assess the extravasations and dissemination of bacteria in vivo, the following experiment was conducted. The mouse ear model described in Example 2 and the PA/PT theranostic device described in Example 24 were used to evaluate the amount of bacteria leaving the vessels and entering the surrounding tissue. FITC and anti-Spa conjugated siMNPs similar to those described in Example 29 were used to target and detect the bacteria. In this case, the bacteria used were S. aureus, as described in Example 24. A laser with a wavelength of 639 nm and an energy fluence of 0.1 J/cm$^2$ was used in this experiment.

The bacteria cells were introduced and labeled via sequential tail vein injections of the unlabeled cells and functionalized siMNPs as described in Example 29. The mouse ear vessel was scanned using the prototype theranostic device to implement in vivo monitoring of bacterial extravasation from a mouse ear vein. Scanning of microvessels using a focused laser beam with a diameter of 10 µm (PA mapping) revealed rare (1-3 per one mm) stationary PA signals preferentially in small venules. In mouse ear vessels, the maximum signal number was reached 5-8 minutes after administration of bacteria and lasted for several hours with only a slight decrease in signal number. While this decrease may reflect the release of bacteria and their re-introduction back into the bloodstream, PA signals were also observed in the immediate vicinity (100-500 µm) of the vessels. This observation suggested extravasation of bacteria into adjacent tissues. Extravasation was confirmed by the examination of tissue samples obtained one hour after injection of bacteria labeled with FITC and 30-nm anti-Spa conjugated siMNPs. Fluorescent imaging of tibial bone, as well as liver and kidney tissues ex vivo revealed strong PA signals generated from fluorescent spots, thus confirming the presence of S. aureus cells in these tissues.

The results of this experiment demonstrated the extravasation and dissemination of bacteria into adjacent tissues.

Example 31. The PA Detection Sensitivity of Labeled Bacteria was Demonstrated In Vitro and In Vivo To demonstrate the PA detection sensitivity of labeled bacteria, the following experiment was conducted.

The PA/PT theranostic system of Example 20 was used to detect siMNP, GNP, and GNR labeled bacteria, as described in Examples 22 and 24, in vitro and in vivo. In this case, the bacteria used were S. aureus, as described in Example 20.

To verify labeling efficiency in the complex environment of blood circulation, stabilized blood samples (10 µL) from donor mice and rats were spiked with $10^4$ bacterial cells resuspended in 1 µL of PBS. Unlabeled S. aureus, bacteria labeled with antibodies alone, bacteria labeled with non-conjugated GNTs, MNPs, and GNRs, or bacteria targeted by functionalized anti-Spa-GNTs, anti-Spa-MNPs, anti-Spa-GNRs$^{900}$ and anti-Lpp-GNRs$^{690}$ as well as by cocktail of nanoparticles (anti-Spa-GNRs$^{900}$+anti-Lpp-GNRs$^{690}$ in equal proportions) were used. High-resolution transmission digital microscope (TDM) imaging was used to image bacteria in thin slide while additional labeling bacteria with FITC was applied to identify bacteria in thick slide with fluorescent microscopy.

Direct labeling in blood was achieved when cocktail of nanoparticles ($10^9$ anti-Spa-GNRs$^{900}$ in 1 µL of PBS+$10^9$ of anti-lipoprotein-GNRs$^{690}$ in 1 µL of PBS) and bacteria ($10^5$ bacteria in 5 µL of PBS) were added to the 100-µL of intact blood and incubated at 37° C. for 30 minutes in incubator with shaker.

To estimate PA threshold sensitivity, mouse blood was spiked ex vivo with unlabeled and labeled bacteria at different concentrations (about 5, 30, and 100 cells per volume analyzed) and subjected to PA imaging on microscope slides. Even at maximum absorption near 740 nm, unlabeled bacteria did not provide detectable signals in these blood samples. Strong signals were observed only with nanoparticle-labeled bacteria as confirmed by optical imaging. By changing the laser beam size and blood sample thickness, the detection limit at a signal-to-noise ratio of 2 was estimated to be one bacterial cell with a beam diameter of 50 µm and thickness of 0.25 mm for anti-Spa conjugated siMNPs and 0.4 mm for the antibody conjugated GNT/GNR cocktail.

Comparison of PA signal rate in vivo for 5 hours after the injection of a small number of bacteria (about 100) into the rat circulation with a total volume of about 25 mL, followed by immediate blood sampling to determine viable bacterial count, demonstrated a sensitivity threshold of 0.5 CFU/mL.

The results of this experiment demonstrated the sensitivity of the detection of nanoparticle-labeled bacteria.

Example 32. Real-Time PA Monitoring of Targeted PT Therapy of CBCs was Demonstrated In Vivo To demonstrate the real-time PA monitoring of targeted PT therapy of CBCs, the following experiment was conducted. The theranostic device described in Example 24 was used to detect and destroy labeled circulating S. aureus bacteria cells (CBCs) described in Examples 26 and 29 using the mouse ear model of Example 2.

To determine an appropriate laser pulse energy fluence for the destruction of labeled bacterial cells, the viability of labeled bacteria in vitro after exposure to a single laser pulse was assessed using PT signal analysis and conventional bacteriological assays. Threshold photodamage as a function of laser fluence leading to 50% cell death was 0.39±0.16 J/cm$^2$ at 900 nm for anti-Spa conjugated GNRs, 0.19±0.11 J/cm$^2$ at 671 nm for anti-Lpp conjugated GNRs, 0.51±0.19 J/cm$^2$ at 671 nm for anti-Spa conjugated siMNPs, and 0.1±0.04 J/cm$^2$ at 900 nm for anti-Spa conjugated GNTs.

The bacteria cells were introduced by tail injection into the mouse tail vein and labeled in vivo by subsequent injection using anti-Spa-conjugated siMNPs. Three experimental groups of mice were subjected to three different treatments: no laser irradiation (control), PA diagnosis at low laser energy fluence (50 mJ/cm$^2$) at 671 nm, and PT therapy by 1-h laser exposure of a 300-µm abdominal blood vessel with laser fluence of 0.8 mJ/cm$^2$ at 850 nm and a pulse rate of 10 Hz.

Figure 58A:
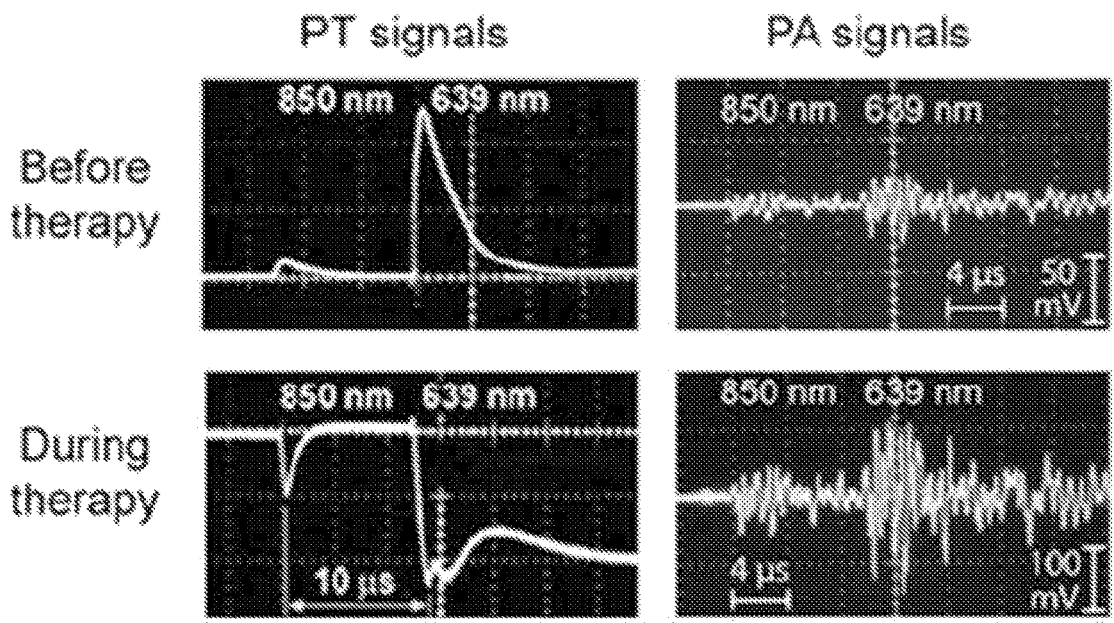
FIG. 58A shows oscilloscope traces of the PA and PT signals produced by pre-labeled bacterial cells before and during the implementation of PT therapy to eradicate the bacteria cells.

FIG. 58A shows two-color (639 and 850 nm) monitoring of PT and PA linear and nonlinear signals from CBCs labeled with anti-Spa-conjugated siMNPs and in vivo real-time monitoring of the efficacy of PT nanotherapy of targeted CBCs for the mice in the PT therapy group. The detection of non-linear PA signals, such as the PA signals shown in the lower right-hand graph, indicated the ongoing destruction of the labeled bacterial cells.

Figure 58B:
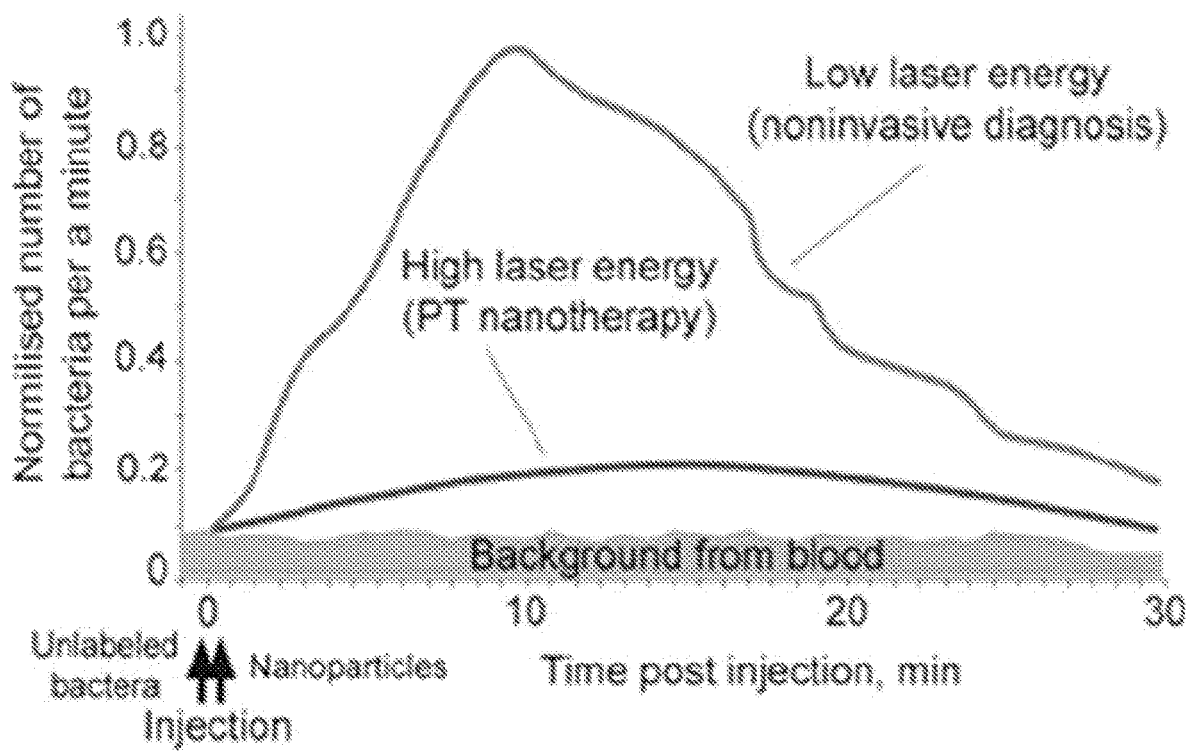
FIG. 58B is a summary of the bacteria detected per minute for bacteria cells labeled in vivo and subjected to either non-destructive PA detection of the bacteria cells or destructive PA therapy to destroy the bacteria cells.

FIG. 58B is a summary of the PA signals detected per minute during a 30-minute post-injection period. The PT therapy group had a significantly reduced number of detected bacterial cells compared to the PA diagnosis group, indicating the destruction of the bacterial cells by the PA therapy. The average standard deviation in PA data for each time point at automated data collection was 19%.

Figure 58C:
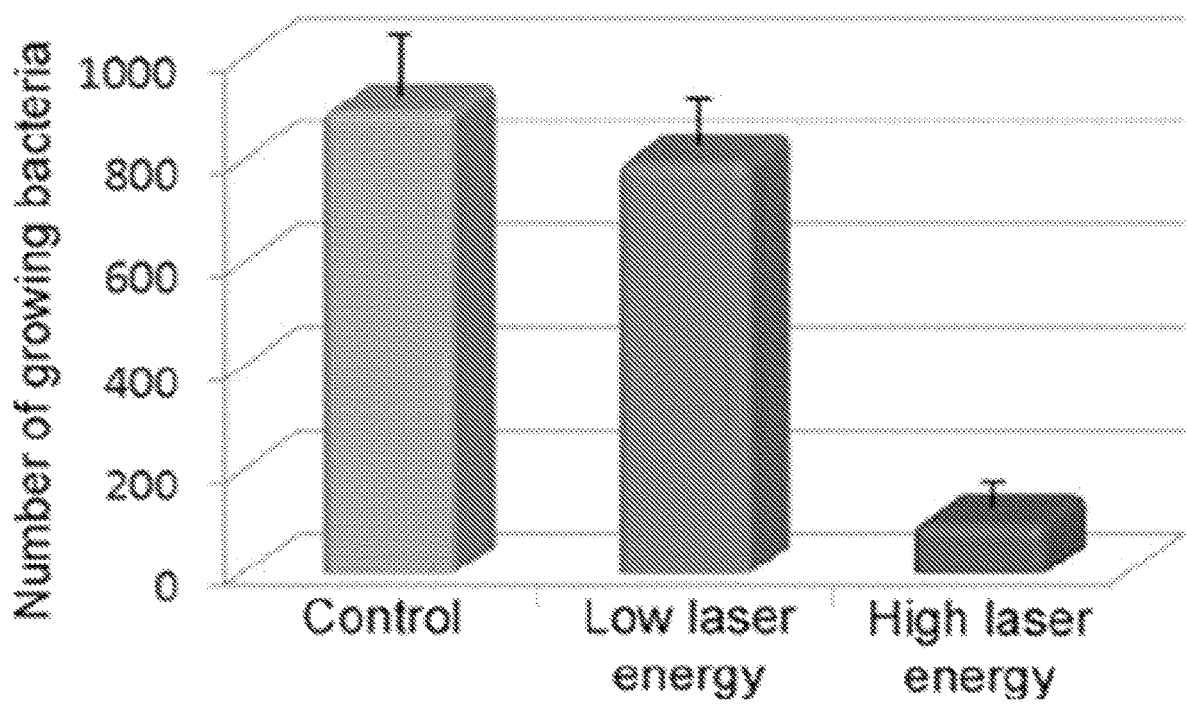
FIG. 58C is a summary of the viable bacteria count in tissue samples obtained from mice subjected to no laser exposure (control), PA monitoring of bacteria, and PA therapy to destroy the bacteria.

To confirm the therapeutic effect of PA therapy, mice from all groups were euthanized and the blood examined for the presence of viable bacteria. The number of viable bacteria in blood samples was determined by plate count as a function of laser irradiation. FIG. 58C summarizes the results of the bacterial plate counts for the three experimental groups. Blood from the control and PA diagnostic groups showed comparable bacterial growth, while the number of bacteria in blood from the PT therapeutic group was reduced 10 to 12 fold.

Figure 59A:
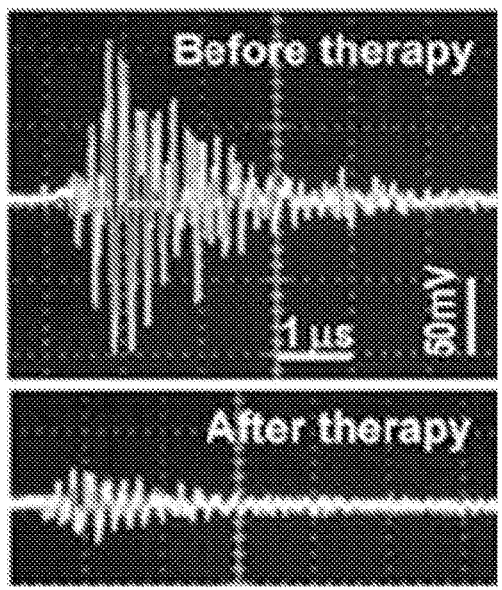
FIG. 59A shows oscilloscope traces of the PA signals produced by labeled bacterial cells before and after the implementation of PT therapy to eradicate the bacteria cells in the blood vessel of a mouse.
Figure 59B:
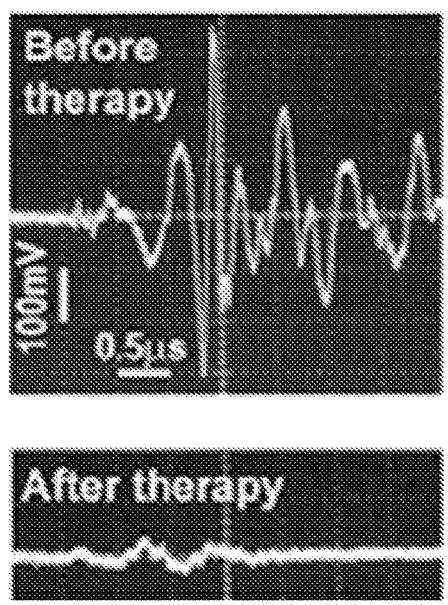
FIG. 59B shows oscilloscope traces of the PA signals produced by labeled bacterial cells before and after the implementation of PT therapy to eradicate the bacteria cells in the liver of a mouse.
Figure 60:
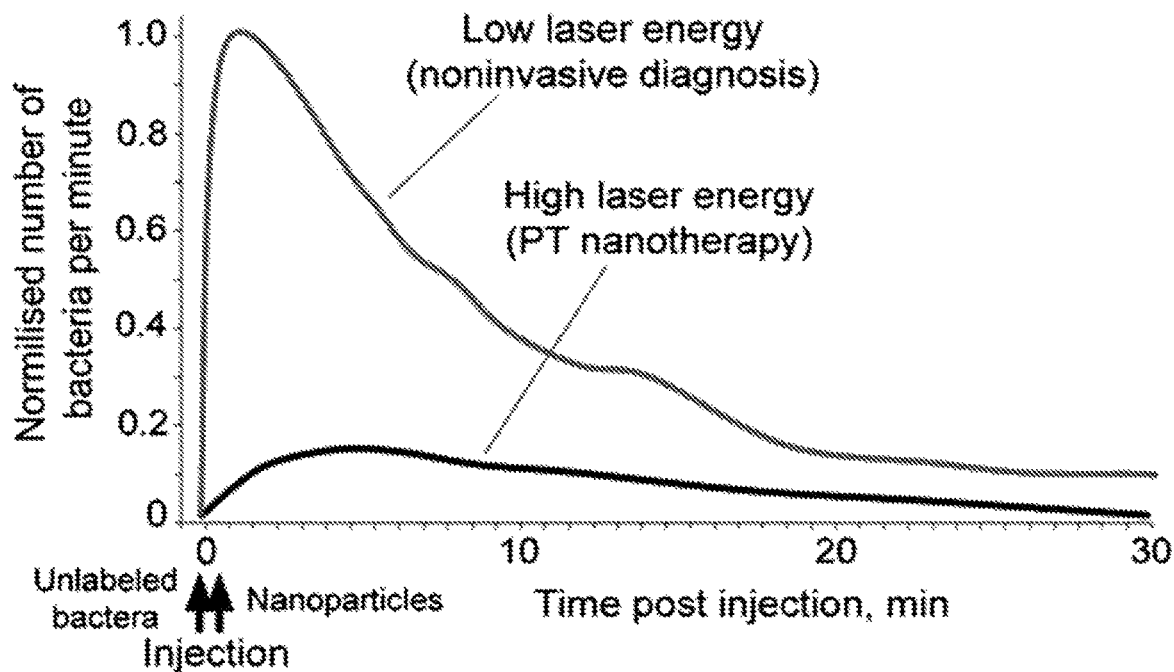
FIG. 60 is a graph illustrating the diagnosis and targeted eradication of S. aureus in blood with real-time monitoring of therapeutic efficacy.
Figure 61:
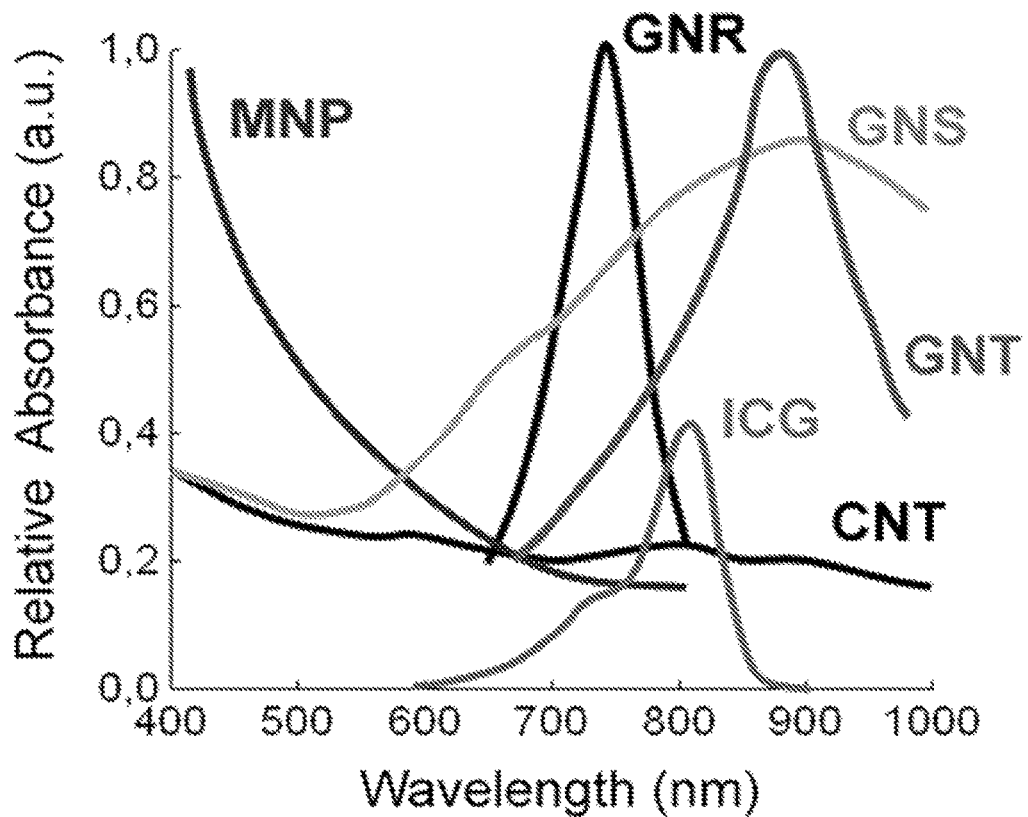
FIG. 61 is an absorbance spectrum for a variety of nanoparticles.

A similar theranostic procedure was used to assess the elimination of bacteria from primary and secondary sites of localized infection in vivo. *S. aureus* cells were pre-labeled in vitro with anti-Spa conjugated GNTs and locally injected at a concentration of 10$^4$ into the ear of a mouse. The labeled bacteria cells produced strong PA signals, as illustrated on the top graph of FIG. 59A. These strong PA signals completely disappeared after PA therapy using laser pulses of 850 nm and energy fluence of 0.8 J/cm$^2$. A secondary infection site in the liver, shown in FIG. 59B, exhibited a similar pattern of high-amplitude PA signal levels that reverted to the background level of uninfected tissue after PA therapy. The targeted PT purging of an infected area in mouse ear may be monitored and controlled by comparing the PA signals produced before, during, and after PT therapy. FIG. 60 is a graph summarizing the PA signals detected during the in vivo eradication of *S. aureus* previously labeled in vitro with real-time monitoring of therapeutic efficacy.

Example 33. Real-Time PA Monitoring of Targeted PT Therapy of CBCs was Demonstrated Using an Extracorporeal Device To assess the implementation of targeted PT therapy using an extracorporeal device, the following experiments were conducted.

An extracorporeal device, illustrated schematically in FIG. 45, was used to implement in vivo PA detection, molecular targeting, and PT purging of infected blood. Catheters were placed in a large artery or vein (e.g., jugular) to create a bypass. The siMNPs, conjugated with anti-Spa antibodies, were injected into the bypass tube. The distance between the injection site and detection points may be adjusted by changing the tube length. Cells labeled in flow were captured by the magnet. Laser irradiation of the area near the magnet generated PA signals, which were detected with an ultrasound transducer attached to the tube. Simultaneously, laser irradiation at higher energy implemented PT killing of targeted bacteria. Conventional transmission imaging made it possible to simultaneously control the positions of the laser beam, magnet, and transducer. High-speed imaging also allowed visualization of individual moving cells at the single-cell level.

The results of this experiment demonstrated the feasibility of using an extracorporeal (bypass) schematic to provide continuous PA monitoring of blood flow in external tubes, and to permit efficient capture of abnormal objects (e.g., bacteria or its toxins targeted by MNPs directly in the extracorporeal flow). Magnetic capture of both abnormal objects and unbound magnetic nanoparticles prevents them from being transported further in the systemic circulation.

It should be understood from the foregoing that, while particular aspects have been illustrated and described, various modifications can be made thereto without departing from the spirit and scope of the invention as will be apparent to those skilled in the art. Such changes and modifications are within the scope and teachings of this invention as defined in the claims appended hereto.

What is claimed is:

1. A method for in vivo integrated photoacoustic and photothermal nano-theranostics of a plurality of circulating target objects in blood, lymph, and other vessels of a living organism, comprising:
   generating at least one series of consecutive diagnostic laser pulses with low energy;
   delivering the laser pulses to the plurality of circulating target objects;
   detecting one or more of laser-induced photoacoustic, photothermal, fluorescence, Raman, high speed transmission, or scattering light signals from the plurality of circulating target objects using ultrasound transducers or photodiodes;
   analyzing the detected signals to determine at least one characteristic of the plurality of circulating target objects; and
   triggering, using the detected signals, a therapeutic laser pulse of high energy at the same or a different wavelength to produce laser-induced photothermal nanobubbles destroying the plurality of circulating target objects.

2. The method of claim 1, the method further comprising monitoring a frequency of detection of the photoacoustic, photothermal, fluorescence, Raman, high speed transmission, or scattering light signals to control the efficacy of photothermal destruction of the plurality of circulating target objects using the frequency of detection.

3. The method of claim 1, wherein the method provides early diagnosis and treatment of metastasis, infection, viruses, clots, thrombosis, plaques, malaria, inflammations, immunodeficiency disorders, or biofilm-associated *S. aureus* bone infection including antibiotic-resistant strains.

4. The method of claim 1, wherein photoacoustic signals emitted by the plurality of circulating target objects result from single photon absorption, two photon absorption, multi-photon absorption, Coherent Anti-Stokes Raman Scattering (CARS), and/or combinations thereof.

5. The method of claim 1, wherein the at least one characteristic of the plurality of circulating target objects is a type, concentration, target speed, total circulating blood or lymph volume, and/or combinations thereof.

6. The method of claim 5, wherein the target speed is determined by a width of the detected signal, a time delay between two detected signals produced by a single target measured at two locations of two distinct laser pulses applied to a known separation distance, or a frequency shift of a signal.

7. The method of claim 5, wherein the total circulating blood or lymph volume is determined using a degree of dilution of one or more absorbing dyes, or blood cells extracted from the organism, labeled using the absorbing dyes, and reintroduced to the organism.

8. The method of claim 1, wherein the plurality of circulating target objects are one or more of normal, apoptotic and necrotic white blood cells, neutrophils, lymphocytes, aggregated red blood cells, infected cells, inflamed cells, stem cells, dendritic cells, platelets, metastatic melanoma cells, leukemia, breast cancer, prostate cancer, ovarian cancer, testicular cancer, fungal cells, protozoa, microorganisms, pathogens, animal cells, plant cells, leukocytes activated by various antigens during an inflammatory reaction, red blood cells in lymphatic vessels, and/or combinations thereof.

9. The method of claim 1, wherein the plurality of circulating target objects possess intrinsic cell-specific markers selected from the group consisting of hemoglobin (Hb), HbH, HbO, metHb, HbCN, HbS, HbCO, HbChr, myoglobins, hemozoin, bilirubin, catalase, porphyrins, flavins, and/or combinations thereof.

10. The method of claim 1, wherein the method uses a label-free approach at NIR wavelengths near 740 nm for non-toxic and noninvasive diagnosis and killing of skin infections including individual unlabeled S. aureus cells with a laser wavelength corresponding to a peak absorption of the S. aureus cells.

11. The method of claim 1, wherein the plurality of circulating target objects are in mammals, reptiles, birds, amphibians, fish, plants, fungi, mollusks, insects, arachnids, annelids, arthropods, roundworms, and flatworms.

12. The method of claim 1, wherein the plurality of circulating target objects are contrast agents selected from the group consisting of indocyanine green dye, melanin, fluorescein isothiocyanate (FITC) dye, evans blue dye, lymphazurin dye, trypan blue dye, methylene blue dye, propidium iodide, Annexin, Oregon Green, C3, Cy5, Cy7, Neutral Red dye, phenol red dye, AlexaFluor dye, Texas red dye, dendrimers, aquasomes, lipopolyplexes, nanoemulsions, perfluorocarbon, polymeric nanoparticles, microbubbles, and/or combinations thereof.

13. The method of claim 1, wherein one or more microbubbles are loaded with contrast dyes or nanoparticles or are conjugated with PEG-coated gold nanoshells leading to laser-induced overheating and microbubble formation.

14. The method of claim 1, wherein the plurality of circulating target objects are labeled by contrast agents that are functionalized with a targeting agent comprising antibodies, proteins, folates, ligands for specific cell receptors, peptides, vitamins, wheat germ agglutinin, and/or combinations thereof.

15. The method of claim 14, wherein the ligands are specific to folate, epithelial cell adhesion molecule (Ep-CAM), Hep-2PAR, CD44, epidermal growth factor receptor (EGFR); PCA, receptors of cancer cells, stem cells, chitin receptors of yeasts, specific to blood or lymphatic cell, endothelial markers, polysaccharide and siderophore receptors of bacteria, or antibody specific for proteins highly expressed in bacteria but absent in mammalian cells.

16. A theranostic device for detection and treatment of a plurality of circulating target objects in blood, lymph, and other vessels of a living organism, the theranostic device comprising:
   a laser for generating one or more laser pulses with low light energy and therapeutic pulses of high light energy;
   an optical module consisting of optical parametric oscillators, optical crystals, etalons, filters, Bragg reflector, and/or Raman shifters;
   one or more ultrasound transducers or photodiodes having one or more amplifiers for receiving laser-induced photoacoustic, photothermal, fluorescence, high speed transmission, Raman, or light scattering signals from the plurality of circulating target objects;
   a data recording system consisting of a boxcar device, a video camera to record a display of an oscilloscope electrically connected to the one or more ultrasound transducers or photodiodes, or a high-speed analog-to-digital board; and
   a computer with stored data analysis software configured to:
      analyze signal patterns of the detected signals;
      trigger, using the detected signals, therapeutic pulses of high light energy to produce nanobubbles destroying the plurality of circulating target objects irrespective of their drug resistance status; and
      monitor a frequency of detection of the photoacoustic, photothermal, fluorescence, Raman, or scattering signals induced by the low energy laser pulses to control the efficacy of photothermal-based destruction of the plurality of circulating target objects using the frequency of detection.

17. The device of claim 16, wherein the laser is a diode pulse laser or modulated continuous radiation in the X-ray spectrum (1-10A), visible-infrared range (0.4 um-20 um), the terahertz spectra (20-1000 um) or the microwave spectra (0.5 mm-3 cm) having a pulse width ranging between 0.1 ps to about 1000 ns; a wavelength ranging between about 600 nm to about 2500 nm, a pulse rate ranging between 1 Hz and 500,000 Hz, and a pulse energy ranging been 0.1 mJ/cm$^2$ and about 10 J/cm$^2$.

18. The device of claim 16, wherein the one or more ultrasound transducers are unfocused transducers; focused cylindrical transducers with focal lengths between about 2 mm and about 500 mm; resonance transducers, transducer with a ring geometry and combinations thereof.

19. The theranostic device of claim 16, the theranostic device further comprising a magnet having a hole through which the laser pulses and/or radiation are delivered, wherein the magnet is in close proximity to an area of interest having flowing target objects that are intrinsically magnetic or are labeled with conjugated magnetic nanoparticles that are clustered alone or with labeled cells under application of a magnetic field.

20. The theranostic device of claim 16, the theranostic device further comprising a customized lens condenser or a fiber having miniature cylindrical optics to create circular or linear beam shapes and deliver radiation to the plurality of circulating target objects.

21. The theranostic device of claim 16, wherein the one or more ultrasound transducers or photodiodes and the laser have a confocal configuration.

22. The theranostic device of claim 16, further comprising an acoustically transparent liquid between a skin and a receiving surface of the one or more ultrasound transducers that transmits laser pulses in the visible and NIR spectra with minimal scattering.

* * * * *